United States Patent [19]
Huang

[11] Patent Number: 5,811,304
[45] Date of Patent: Sep. 22, 1998

[54] NUCLEIC ACID MOLECULES ENCODING RETINOBLASTOMA PROTEIN-INTERACTING ZINC FINGER PROTEINS

[75] Inventor: Shi Huang, San Diego, Calif.

[73] Assignee: La Jolla Cancer Research Foundation, La Jolla, Calif.

[21] Appl. No.: 459,568

[22] Filed: Jun. 2, 1995

Related U.S. Application Data

[63] Continuation of Ser. No. 399,411, Mar. 6, 1995, which is a continuation-in-part of Ser. No. 292,683, Aug. 18, 1994, abandoned.

[51] Int. Cl.$^6$ .............................. C07H 21/02; C12N 5/06; C12N 15/00

[52] U.S. Cl. .................... 435/325; 435/69.1; 435/172.3; 435/410; 435/243; 435/320.1; 435/375; 435/377; 536/23.1; 536/23.5; 935/22; 935/23; 935/24; 935/34; 935/66; 935/70; 935/71

[58] Field of Search .................................. 536/23.1, 23.4, 536/23.5, 24.33; 435/240.2, 252.3, 320.1, 69.1, 172.3, 243, 375, 377, 410, 325; 514/44; 935/22, 23, 24, 34, 66, 90, 71

[56] References Cited

PUBLICATIONS

Bourne et al., "The GTPase superfamily: conserved structure and molecular mechanism." *Nature*, 349:117–127 (1991).

Boyd et al., "A region in the C–terminus of adenovirus ⅖ E1a protein is required for association with a cellular phosphoprotein and important for the negative modulation of T24–ras mediated transformation, tumorigenesis and metastasis." *EMBO. J.* 12:469–478 (1993).

Van Cherington et al., "Separation of simian virus 40 large T antigen transforming and orgin–binding functions from the ability to block differentiation." *Mol. Cell. Biol.*, 8:1380–1384 (1988).

DeCaprio et al., "SV40 large tumor antigen forms a specific complex with the product of the retinoblastoma susceptibility gene." *Cell*, 54: 275–283 (1988).

Defeo–Jones et al., "Cloning of cDNAs for cellular proteins that bind to the retinoblastoma gene product." *Nature*, 352:251–254 (1993).

Dowdy et al., "Physical interaction of the retinoblastoma protein with human D cyclins." *Cell* 73:499–511 (1993).

Durfee et al., "The retinoblastoma protein associates with the protein phosphatase type 1 catalytic subunit." *Genes Dev.*, 7:555–569 (1993).

Dyson et al., "Adenovirus E1A makes two distinct contacts with the retinoblastoma protein." *J. Virol.*, 66:4606–4611 (1992).

Ewen et al., "Functional interactions of the retinoblastoma protein with mammalian D–type cyclins." *Cell*, 73:487–497 (1993).

Ford et al., "Nuclear protein with sequence homology to translation initiation factor eIF–4A." *Nature*, 332:736–738 (1988).

Harlow et al., "Association of adenovirus early region 1A proteins with cellular polypeptides." *Mol. Cell. Biol.*, 6:1579–1589 (1986).

Hirling et al., "RNA helicase activity associated with the human p68 protein." *Nature*, 339:562–564 (1989).

Hu et al., "The regions of the retinoblastoma protein needed for binding to adenovirus E1A or SV40 large T antigen are common sites for mutations." *EMBO J.*, 9:1147–1155 (1990).

Huang et al., "Two distinct and frequently mutated regions of retinoblastoma protein are required for binding to SV40 T antigen." *EMBO J.*, 9:1815–1822 (1990).

Huang et al., "A cellular protein that competes with SV40 T antigen for binding to the retinoblastoma gene product." *Nature*, 350:160–162 (1991).

Huang et al., "The retinoblastoma protein region required for interaction with the E2F transcription factor includes the T/E1A binding and carboxy–terminal sequences." *DNA Cell Biol.*, 11:539–548 (1992).

Kaelin, Jr. et al., "Definition of the minimal simian virus 40 large T Antigen and adenovirus E1A–binding domain in the retinoblastoma gene product." *Mol. Cell. Biol.*, 10:3761–3769 (1990).

Keller and Maniatis, "Identification and characterization of a novel repressor of β–interferon gene expression." *Genes Dev.*, 5:868–879 (1991).

Kimelman et al., "E1a regions of the human adenoviruses and of the highly oncogenic simian adenovirus 7 are closely related." *J. Virol.*, 53:399–409 (1985).

M. Kozak, "An analysis of 5' noncoding sequences from 699 vertebrate messenger RNAs." *Nucl. Acids Res.* 15:8125–8148 (1987).

Krieg and Melton, "Functional messenger RNAs are produced by SP6 in vitro transcription of cloned cDNAs." *Nucl. Acids Res.*, 12:7057–7070 (1984).

Lane and Hoeffler, "SV40 large T shares an antigenic determinant with a cellular protein of molecular weight 68,000." *Nature*, 288:167–170 (1980).

Lillie et al., "Functional domains of adenovirus type 5 E1a proteins." *Cell*, 50:1091–1100 (1987).

Ludlow et al., "SV40 large T antigen binds preferentially to an under phosphorylated member of the retinoblastoma susceptibility gene product family." *Cell*, 56:57–65 (1989).

Mihara et al., "Cell cycle–dependent regulation of phosphorylation of the human retinoblastoma gene product." *Science*, 246:1300–1303 (1989).

E. Moran, "A region of SV40 large T antigen can substitute for a transforming domain of the adenovirus E1A products." *Nature*, 334:168–170 (1988).

(List continued on next page.)

*Primary Examiner*—Brian R. Stanton
*Attorney, Agent, or Firm*—Campbell & Flores LLP

[57] ABSTRACT

The present invention provides a nucleic acid molecule encoding a mammalian retinoblastoma protein-interacting zinc finger (RIZ) protein, which binds retinoblastoma protein. In addition, the invention provides methods for reducing the growth of a tumor cell by introducing a nucleic acid molecule encoding a RIZ into the tumor cell.

10 Claims, 21 Drawing Sheets

OTHER PUBLICATIONS

Moran and Matthews, "Multiple functional domains in the adenovirus E1A gene." *Cell*, 48:177–178 (1987).

J.R. Nevins, "E2F: a link between the Rb tumor suppressor protein and viral oncoproteins." *Science*, 258:424–429 (1992).

Pawson and Gish, "SH2 and SH3 domains: from structure to function." *Cell* 71:359–362 (1992).

Qin et al., "Identification of a growth suppression domain within the retinoblastoma gene product." *Genes Dev.*, 6:953–964 (1992).

Quinlan et al., "Growth factor induction by the adenovirus type 5 E1A 12S protein is required for immortilization of primary epithelial cells." *Mol. Cell. Biol.*, 8:3191–3203 (1988).

Quinlan and Douglas, "Immortilization of primary epithelial cells requires first–and second–exon functions of adenovirus type 5 12s." *J. Virol.*, 66:2020–2030 (1992).

Ren et al., "Identification of a ten–amino acid proline–rich SH3 binding site." *Science*, 259:1157–1161 (1993).

Saraste et al., "The P–loop—a common mofit in ATP–and GTP–binding proteins." *Trends. Biochem. Sci.*, 15:430–434 (1990).

Scheffner et al., "RNA unwinding activity of SV40 large T antigen." *Cell* 57:955–963 (1989).

Smith and Ziff, "The amino–terminal region of the adenovirus serotype 5 E1a protein performs two separate functions when expressed in primary baby rat kidney cells." *Mol. Cell. Biol.*, 8:3882–3890 (1988).

Subramanian et al., "Enhanced ras oncogene mediated cell transformation and tumorigenesis by adenovirus 2 mutants lacking the C–terminal region of E1a protein." *Oncogene*, 4:415–420 (1989).

Templeton et al., "Nonfunctional mutants of the retinoblastoma protein are charcterized by defects in phosphorylation, viral oncoprotein association, and nuclear tethering." *Proc. Natl. Acad. Sci. USA*, 88:3033–3037 (1991).

Wang et al., "Identification of specific adenovirus E1A N–terminal residues critical to the binding of cellular proteins and the control of cell growth." *J. Virol.*, 67:476–488 (1993).

R.A. Weinberg, "Tumor suppressor genes." *Science*, 254:1138–1146 (1991).

Welch and Wang, "A C–terminal protein–binding domain in the retinoblastoma protein regulates nuclear c–Abl tyrosine kinase in the cell cycle." *Cell*, 75:779–790 (1993).

Whyte et al., "Association between an oncogene and an anti–oncogene: the adenovirus E1A proteins bind to the retinoblastoma gene product." *Nature* 334:124–129 (1988).

Whyte et al., "Cellular targets for transformation by the adenovirus E1A proteins." *Cell*, 56:67–75 (1989).

Walker et al., "Distantly related sequences in the α–and β–subunits of ATP synthase, myosin, kinases and other ATP–requiring enzymes and a cummon nucleotide binding fold." *Embo J.*, 1(8):945–951 (1982).

Chen et al., "Phosphorylation of the retinoblastoma gene product is modulated during the cell cycle and cellular differentiation." *Cell*, 58:1193–1198 (1989).

DeCaprio et al., "The product of the retinoblastoma susceptibility gene has properties of a cell cycle regulatory element." *Cell*, 58:1085–1095 (1989).

S. Huang, "Blimp–1 is the murine homolog of the human transcriptional repressor PRDI–BF1." *Cell*, 78:1 (1994).

Iggo and Lane, "Nuclear protein p68 is an RNA–dependent ATPase." *EMBO J.*, 8(6): 1827–1831 (1989).

Moran et al., "Identification of separate domains in the adenovirus E1A gene for immortilization activity and the activation of virus early genes." *Mol. and Cell. Biol.*, 6(10):3470–3480 (1986).

Buchkovich et al., "The retinoblastoma protein is phosphorylated during specific phases of the cell cycle." *Cell*, 58:1097–1105 (1989).

Chen et al., "Identification of a Human Homologue of Yeast Nuc2 Which Interacts with the Retinoblastoma Protein in a Specific Manner." *Cell Growth & Differ.* 6:199–210 (1995).

Bartholomew and Ihle, "Retroviral insertions 90 kilobases proximal to the Evi–1 myeloid transforming gene activate transcription from the normal promoter." *Mol. Cell. Biol.*, 11(4):1820–1828 (1991).

Morishita et al., "Expression of the Evi–1 zinc finger gene in 32Dc13 myeloid cells blocks granulocytic differentiation in response to granulocyte colony–stimulating factor." *Mol. Cell. Biol.*, 12(1):183–189 (1992).

Buyse et al., "The retinoblastoma protein binds to RIZ, a zinc–finger protein that shares an epitope with the adenovirus E1A protein." *Proc. Natl. Acad. Sci. USA*, 92:4467–4471 (1995).

Kreider et al., "Loss of erythopoietin responsiveness in erythroid progenitors due to expression of the Evi–1 myeloid–transforming gene." *Proc. Natl. Acad. Sci. USA*, 90:6454–6458 (1993).

Miyoshi et al., "t (8:21) breakpoints on chromosome 21 in acute myeloid leukemia are clustered within a limited region of a single gene, AMLI." *Proc. Natl. Acad. Sci. USA*, 88:10431–10434 (1991).

Nucifora et al., "Consistent intergenic splicing and production of multiple transcripts between AMLI at 21q22 and unrelated genes at 3q26 in (3;21) (q26;q22) translocations." *Proc. Natl. Acad. Sci. USA*, 91:4004–4008 (1994).

Morishita et al., "Unique expression of the human Evi–1 gene in an endometrial carcinoma cell line: sequence of cDNAs and structure of alternatively spliced transcripts." *Oncogene*, 5:963–971 (1990).

Lee et al., "Dual roles of the retinoblastoma protein in cell cycle regulation and neuron differentiation." *Genes & Development*, 8:2008–2021 (1994).

Garriga et al., "Migrations of the *caenorhabditis elegans* HSNs are regulated by egl–43, a gene encoding two zinc finger proteins." *Genes & Development*, 7:2097–2109 (1993).

Turner et al., "Blimp–1, a novel zinc finger–containing protein that can drive the maturation of B lymphocytes into immunoglobulin–secreting cells." *Cell*, 77:297–306 (1994).

Weinberg Robert A., "The retinoblastoma protein and cell cycle control." *Cell*, 81:323–330 (1995).

Moristita et al., "EVI–1 zinc finger protein works as a transcriptional activator via binding to a consensus sequence of GACAAGATAAGATAAN$_{1-28}$ CTCATCTTC." *Oncogene*, 10:1961–1967 (1995).

Mitani et al., "Generation of the AML1–EVI–1 fusion gene in the t(3;21) q26;q22) causes blastic crisis in chronic myelocytic leukemia." *EMBO J.*, 13(3):504–510 (1994).

Rechsteiner, Martin, "Regulation of enzyme levels by proteolysis: the role of pest regions." *Adv. Enzyme. Requl.*, 27:135–151 (1988).

Morishita et al., "Retroviral activation of a novel gene encoding a zinc finger protein in IL–3 dependent myeloid leukemia cell lines." *Cell*, 54:831–840 (1988).

Morishita et al., "The Evi–1 zinc finger myeloid transforming gene is normally expressed in the kidney and in developing oocytes." *Oncogene,* 5:1419–1423 (1990).

Perkins et al., "Patterns of Evi–1 expression in embryonic and adult tissues suggest that Evi–1 plays an important regulatory role in mouse development." *Development,* 111:479–487 (1991).

Orkin, S et al. (1995) Report and Recommendations of the Panel to Assess the NIH Investment; Research on Gene Therapy Mulligan, R.

Lehningera et al (1992). Principles of Biochemistry, Worth Publisher, pp. 951–953, 999.

```
RIZ          1125  CNVCESPFLSIKDLTKHLSVHAEEWPFKCEFCVQLFKVKTDLSEHRFLLHGVGNIFVCSVCKKEFAFLCNLQQHQRDLHPDEVCTH  1210
PRDI-BF1      543  CNVCAKTFGQLSNLKVHLRVHSGERPFKCQTCNKGFTQLAHLQKH-YLVHTGEKPHECQVCHKRFSSTSNLKTHLR-LHSGEKPYQ   626
CONSENSUS          CNVC...F.....L..HL.VH..E.PFKC..C...F.....L..H..L.H.......C.VC.K.F....NL..H.R.LH..E....
DNA-CONTACTS              *               *                *                *  *
```

FIG. 2C-1

```
RIZ           39  TRIGVWATKPILKGKKFGPFVGDKKKRSQVRNNV--YMWEVYYPNLGWMCIDATDPEKGNWLRYVNWACSGEEQNLFPL  115
PRDI-BF1      60  EVIGVMSKEYIPKGTRFGPLIGEIYTNDTVPKNANRKYFWRIYSRGELHHFIDGFNEEKSNWMRYVNPAHSPREQNLAAC  139
CONSENSUS         ..IGV......I.KG..FGP..G......V..N.....Y.W..Y........ID....EK.NW.RYVN.A..S..EQNL...

RIZ          116  EINRAIYYKTLKPIAPGEELLVWYNGEDNP  145
PRDI-BF1     140  QNGMNIYFYTIKPIPANQELLVWYCRDFAE  169
CONSENSUS         .....IY..T.KPI....ELLVWY......
```

```
          10         20         30         40         50         60         70         80         90        100        110        120
1234567890123456789012345678901234567890123456789012345678901234567890123456789012345678901234567890123456789012345678901234567890
ACAGATTAACGGCGGGGACATGAGCGGCGCCATGAGCGGACAGGGTTAAAGCTGAAGCGGAAACCAGCCAAACACTACAGCCGTCAGAGGATCTGGCTGATGGCAAAGCATCTGGAGAAACGTT       1320
 T  Q  I  N  R  R  H  E  A  G  L  K  R  K  P  S  Q  T  L  Q  P  S  E  D  L  A  D  G  K  A  S  G  E  N  V

GCTTCAAAAGATGATTCGAGTCTCCCAGTCCTTGGGCCAGACTGTCTGATCATGAATTCAGAGAAAGGCTTCCCAAGACACAATAAATTCTTCGTCGTAGAAGAGAATGGGGAAGTTAAA          1440
 A  S  K  D  D  S  S  P  P  S  L  G  P  D  C  L  I  M  N  S  E  K  A  S  Q  D  T  I  N  S  S  V  E  E  N  G  E  V  K

GAACTTCATCCGTGCAAATATTGTAAAAAGGTTTTTGGAACTCATATGAGACGGCATCCAGGTAGAGTTCACGAACGTCATCTGATTCCCAAAGGTGTACGGCGAAAAGGAGGC                1560
 E  L  H  P  C  K  Y  C  K  K  V  F  G  T  H  T  N  M  R  R  H  Q  R  R  V  H  E  R  H  L  I  P  K  G  V  R  R  K  G  G

CTTGAGAGCCCCAGCCTCCAGCAGCCCCCAGGCCCAGGACCCAGCTGTATGTACCAAGACAGAGAACAGTGTAGCAGGAAGCAGATGATGATGTGTACATCATGGACATTTCTAGC             1680
 L  E  E  P  Q  P  P  A  E  Q  A  Q  A  T  Q  N  V  Y  V  P  S  T  E  P  E  E  E  G  E  A  D  D  V  Y  I  M  D  I  S  S

AATATCTCTGAAAACTTAAATTACTATATTGATGGTAAATTCAAACTACTAGTAACTGTAAAATTCAAACAGATCCAAACAGTAGTGCTTGATGATTGAGATGGAGTCTGCAGATTTGTATGGTATAAATTGT       1800
 N  I  S  E  N  L  N  Y  Y  I  D  G  K  I  Q  T  N  N  T  S  N  C  D  V  I  E  M  E  S  A  S  A  D  L  Y  G  I  N  C

CTGCTCACTCCAGTTACAGTGGGAAATTACTCAAAATTCAAACAGACCACACAGGTCCCTGTAACAGAGATCTTCCTGCTCTTCTTTGCTTCCCCTCTTGTCCCTGCAGGGATTTCAGCAACTAAACTA           1920
 L  L  T  P  V  T  V  E  I  T  Q  N  I  K  T  T  Q  V  P  V  T  E  D  L  P  K  E  P  L  G  S  T  N  S  E  A  K  K  R  R

ACTGCGAGCCAGCCCACCTGACTGCCCAAATTAAGGCCGAAACAGACTCTGACCCCATGGTGCCCATCATGCAGGGATTCAGCAACTAAATAACTAACTGAAATAGCTAAATTAGGTCCTGTCTTGTTGTG        2040
 T  A  S  P  P  H  L  T  A  Q  I  K  A  E  T  D  S  D  P  M  V  P  S  C  S  L  P  L  S  I  S  I  T  E  A  V  S  F  H

AAAGAGAAAGTGTTTATTGTCATCAAAGCTCAAACTCTTCAAACATAAACTTCTTCCCCAGTTCTCCACAGTCCTGCCCTTTGAAGACTTTGGAAAGCCAAGTGATGGG                   2160
 K  E  K  S  V  Y  L  S  S  K  L  K  Q  L  L  Q  T  Q  D  D  K  L  T  P  P  A  G  I  S  A  T  E  I  A  K  L  G  P  V  C  V

TCTGCTCCTGCATCAATGTTGCCTGTGACTGGGCTGACTTCCAAAGGTAGGTTTAAGAGGCGGACCAGTCCTCCTCCCCAGTCCTCCACAGCATGGAGTTTGTGTGGGAGGAGATGAGAGAAACTGTGAGCCCTCCATGC    2280
 S  A  P  A  S  M  L  P  V  T  S  R  F  K  R  R  T  S  S  P  P  Q  H  S  P  A  L  R  D  F  G  K  P  S  D  G

AAAGCAGCAGACCGATGCGGGGCTGACTTCCAAAAATCCAAATTAGAAGTCACGAAGTCAGGAGTTGTGTTGGGAGAGATGAGAGAAACTGTGAGCCCTCCATGC                       2400
 K  A  A  W  T  D  A  G  L  T  S  K  K  K  S  K  L  E  S  H  S  D  S  P  A  W  S  L  S  G  R  D  E  R  E  T  V  S  P  P  C

TTTGATGAATATAAAATGTCTAAAGAGTGGACTAGTTCTGCTTTTAGCAGTGTGTGCAACCAGCAGCCACTGGATTATCCAGGATTGTCAAACAGAGAGGCTGAGGGTACAGGCAAG            2520
 F  D  E  Y  K  M  S  K  E  W  T  A  S  S  A  F  F  S  S  V  C  N  Q  Q  P  L  D  L  S  S  G  V  K  Q  K  A  E  G  G  T  G  K
```

```
             10         20         30         40         50         60         70         80         90        100        110        120
     1234567890123456789012345678901234567890123456789012345678901234567890123456789012345678901234567890123456789012345678901234567890
     ATAAAGACAAAAGATCCAGATGTTCGATTGGGCCTCAATCAGCATTACCCAAGCTTTAAACCACCTCCATTTCAGTACCATCACGTAACCCATGGGGATTGGTGTGACAGCCACAAAT       3960
      I  K  T  K  D  P  D  V  R  L  G  L  N  Q  H  Y  P  S  F  K  P  P  P  F  Q  Y  H  H  R  N  P  M  G  I  G  V  T  A  T  N
     TTCACTACACACAATATTCCACAGACTTTCACTACGCCATTCGCTGCTGCACAAAGTGTGCAGAGTTGCACAAACATATCCTGGCTTGTGCTTCTGCAAGT                         4080
      F  T  T  H  N  I  P  Q  T  F  T  T  A  I  R  C  T  K  C  C  G  K  G  V  D  N  M  P  E  L  H  K  H  I  L  A  C  A  S  A  S
     GACAAGAAGAGGTACACGCCTAAGAAAAACCCAGTCCTGAAATGGGCGTGCAACCCAAAATGGGCTGTGGTTTTAGATAACTCTGGGAAAAATGCCTTCGACGAATGGGACAG             4200
      D  K  K  R  Y  T  P  K  K  N  P  V  P  L  K  Q  T  V  Q  P  K  N  G  V  V  V  L  D  N  S  G  K  N  A  F  R  R  M  G  Q
     CCCAAAAGGCTTAACTTTAGTGTTGAGCTCAGCAAAATGTCGTCAGAATAAGCTCAAATCTCACATTGCCCTTACTGTAATGCTAGACAGAAAGCAATTCAGATCAGAAAACAATCT          4320
      P  K  R  L  N  F  S  V  E  L  S  K  M  S  S  N  K  L  K  L  N  A  L  K  K  K  N  Q  L  V  Q  K  A  I  L  Q  K  N  K  S
     GCAAAGCAGAAGGCCGACTTGAAAAATGCTGTGAGTGTCATCCTCCCCAAAGTTCATTCATTGGAAGCTGTCACTTACATTGGAAGCTGTCACATTCAGCTGTCC                      4440
      A  K  Q  K  A  D  L  K  N  A  C  E  S  S  S  H  I  C  P  Y  C  N  R  E  F  T  Y  I  G  S  L  N  K  H  A  F  S  C  P
     AAAAACCCCTTTCTCCCCAAAAAAAGTTTCTCATTCATCTAAGAAAGGTGACACTCCTGCCAAGTAGTACAGTAACAGTAACTGACAAAAACAGTAACAGTAACACGCCGCCTTCAGCTGTCCC   4560
      K  K  P  L  S  P  P  K  K  K  V  S  H  S  S  K  K  G  G  H  S  S  P  A  S  S  S  D  K  N  S  N  H  R  R  R  T  A  D
     GCCGAGATTAAAATGCAAAGCCATGCAGAGTCAGGACACCAAGCCAGTCCAGGCCAGAGAACTCAGGAAACTCAGGGCCAAATAACTCAGGTCCTTCAGGTCCAAGCAGAACGTCAAGTTT      4680
      A  E  I  K  M  Q  S  M  Q  T  P  L  G  K  T  R  A  R  S  S  G  P  P  T  Q  V  P  L  P  S  S  F  R  S  K  Q  N  V  K  F
     GCAGCTTCGGTGAAATCAAAAGCCAAGCCTTCCTCTCTTTAAGGAACTCCAGCCGATAAGAACTCCAGTCCTCCAGAAGAGAGAAAGCAAATCACCACCTTGTTGAGGGGCCAAAAACTAAAGCTGTGGCCAAGAATCAT   4800
      A  A  S  V  K  S  K  K  P  S  S  L  R  N  S  S  P  I  R  M  A  K  I  T  H  V  E  G  K  K  P  K  A  V  A  K  N  H
     TCTGCTCAGCTTTCCAGCAAACATCGCGGAGCCTGCACGTGAGGGTACAGAAAAGCAAATCACACCTGTTTTACAAGCAAATCAAGGGGTTCAATATA                             4920
      S  A  Q  L  S  S  K  T  S  R  S  L  H  V  R  V  Q  K  S  K  A  V  L  Q  S  K  R  T  D  R  F  N  I
     AAATCTAGAGAGCGGAGTGGGGGCCAGTCACCCGAGCCTTCAGCTGACTTGAGTGAGAACAAGAGAGAGGACGGCAGCGCCAAGCAGGAGCTGAAGGACTTCAGC                      5040
      K  S  R  E  R  S  G  G  P  V  T  R  S  L  Q  L  A  A  A  D  L  S  E  N  K  R  E  D  G  S  A  K  Q  E  L  K  D  F  S
     TACAGCCTCCGCCTTGGCGTCCCGATGCTCTCTCCACCAGGCGCCCCAGTCACCAGGCAGTAGGAAGGTCAAAGTTCCAGGGACCATTCTTCAAAGAGTAG                          5160
      Y  S  L  R  L  A  S  R  C  S  P  P  A  A  P  Y  I  T  R  Q  F  Q  G  G  P  F  F  K  E  *
     ACACTCTGGCTGCTCCCTGACAG                                                                                                          5183
```

FIG. 9D

```
hRIZ      MQNITEEVA ATETLAEVPE HVLRGLPEEV RLFPSAVDKT RIGVWATKPI LKGKKFGPFV    60
rRIZ      MQNITEEVA ATETLAEVPE HVLRGLPEEV RLFPSAVDKT RIGVWATKPI LKGKKFGPFV    59
Consensus  M QN TE VA ATETLAEVPE HVLRGLPEEV RLFPSAVDKT RIGVWATKPI LKGKKFGPFV    60 hRIZ      GDKKKRSQVK NNVYMWEVYY PNLGWMCIDA TDPEKGNWLR YVNWACSGEE QNLFPLEINR   120
rRIZ      GDKKKRSQVR NNVYMWEVYY PNLGWMCIDA TDPEKGNWLR YVNWACSGEE QNLFPLEINR   119
Consensus GDKKKRSQV  NNVYMWEVYY PNLGWMCIDA TDPEKGNWLR YVNWACSGEE QNLFPLEINR   120 hRIZ      AIYYKTLKPI APGEELLVWY NGEDNPEIAA AIEEERASAR SKRSSPKSRK GKKKS ENKN   180
rRIZ      AIYYKTLKPI APGEELLVWY NGEDNPEIAA AIEEERASAR SKRSSPKSRR GKKKS ENKN   179
Consensus AIYYKTLKPI APGEELLVWY NGEDNPEIAA AIEEERASAR SKRSSPKSR  GKKKS ENKN   180 hRIZ      KGNKIQDIQL KMSE D  SA NMR SAEGPK EDEEN P ASA  EQPA L EV  ASQEV E A   240
rRIZ      KGIRTHPTQL KMSE ID  FA NMR SAEGPK EEDEH P ASA  EQPAFL EV  GNQDAVPQVA   239
Consensus KG     QL  K SE         NMR SAEGPK E  E  P  ASA  EQPA L EV   Q     A   240 hRIZ      TPAPA EPQP EFDERL AAA            CEVND EEEE EEEEEE EEE EE   EE DEGEEA MP   300
rRIZ      IFIPA EPQP EVDGKQ VTD            CEVND VEEE EEEEEE EEE EE   EE EDGVEEAD MP   295
Consensus    PA EPQP E D                    CEVND  E    E     EEE EE        G EEA MP   300 hRIZ      NENS KEPEI RC EKPEDLL EEPKTISEE T   LED CSEVTPA  MQIPRTK EEA NGDV ETFMF   360
rRIZ      NEES KEPEI RC EKPEDLL EEPQSMSNE A   RED SPQVTPP  PHIPR A REEA NGDVL ETFMF   355
Consensus NE S KEPEI RC EKPEDLL EEP              ED    VTP      PR    EEA NGDV  ETFMF   360
```

FIG. 10A

```
hRIZ        PCQHCERKF  TKQGLERHMH  IHISTNNHAF  KCKYCGK FG  TQINRRHER  RHE GLKR P    420
rRIZ        PCQHCERKF  TKQGLERHMH  IHISTDNHAF  KCKYCGK FG  TQINRRRHER RHE TGLKR P   415
Consensus   PCQHCERKF  TKQGLERHMH  IHIST NHAF  KCKYCGK FG  TQINRRHER  RHE GLKR P    420 hRIZ        S TLQ SED   ADGKA GENV  SKD SSPPS  LG DCLI NS  EK SQDTINS  S EENGEVK    480
rRIZ        SVTLQ SEDP  DDGK- -GENV  SKD SSPPQ  LG DCLI NS  EK SQEVINS  SF EENGEVK  473
Consensus   S TLQ SED   DGK   GENV  SKD SSPP   LG DCLI NS  EK SQ      NS S EENGEVK  480 hRIZ        ELHPCKYCKK  VFGTHTNMRR  HQRRVHERHL  IPKGVRRKGG  L F PQPPAE  QADA QNVYV   539
rRIZ        ELHPCKYCKK  VFGTHTNMRR  HQRRVHERHL  IPKGVRRKGG  L E PQPPAE  QAPPS QNVYV  533
Consensus   ELHPCKYCKK  VFGTHTNMRR  HQRRVHERHL  IPKGVRRKGG  L E PQPPAE  QA    QNVYV  540 hRIZ        PSTEPEEEGE  ADDVYIMDIS  SNISENLNYY  IDGKIQTNN   TSNCDVIEME  S SA LYGIN   599
rRIZ        PSTEPEEEGE  DDDVYIMDIS  SNISENLNYY  IDGKIQTNSS  TSNCDVIEME  S SA LYGID   593
Consensus   PSTEPEEEGE  DDVYIMDIS   SNISENLNYY  IDGKIQTN    TSNCDVIEME  S SA LYGI    600 hRIZ        CLLTPVTVEI  TQNIK TQVP  VT DL KEPL  QSTNSE KKR  RTASPP LPK  IK ET SD PM   659
rRIZ        CLLTPVTVEI  TQNIK TQVS  VT DL K SP  SSTNCE KKR  RTASPP LPK  IK ET SDSST   653
Consensus   CLLTPVTVEI  TQNIK TQV   VT D  K      STN E KKR  RTASPP LPK  IK ET SD      660 hRIZ        VPSCSLSLPL  SIST E VSF  HKEK VYLSS  KLKQLLQTQD  KLT PAG SA  EI KLGPVC    719
rRIZ        APSCSLSLPL  SIST E VSF  HKEK VYLSS  KLKQLLQTQD  KLT PAG SA  EI KLGPVC    713
Consensus   PSCSLSLPL   SIST E VSF  HKEK VYLSS  KLKQLLQTQD  KLT PAG SA  EI KLGPVC    720
```

FIG. 10B

```
hRIZ       VSAPASMLPV TSSRFKRRTS SPPSSPQHSP ALRDFGKP D GKAAWTDA L TSKK KLESH    779
rRIZ       ASAPASMLPV TSSRFKRRTS SPPSSPQHSP ALRDFGKP ND GKAAWTD VL TSKK KLESR   773
Consensus   SAPASMLPV TSSRFKRRTS SPPSSPQHSP ALRDFGKP  D GKAAWTD    L TSKK KLES  780 hRIZ       SDSPAWSLSG RDERET SPP  CFDEYK MSKE W ASS N FSSV CNQQPLDLSS GVKQK EGTG  839
rRIZ       SDSPAWSLSG RDERET SPP  CFDEYK ISKE W ASS I FSSV CNQQPLDLSS GVKQK EGTG  833
Consensus  SDSPAWSLSG RDERET SPP  CFDEYK  SKE W ASS   FSSV CNQQPLDLSS GVKQK EGTG  840 hRIZ       KTPV WESVL DLSVHKK  S  DSEGKEFKE S  H SV QP TC SA       KK KPTTCML QKVLLNEYNG  899
rRIZ       KTPV WESVL DLSVHKK  C  DSEGKEFKE N  H L AQP  -  AA      KK KPTTCML QKVLLNEYNG  889
Consensus  KTPV WESVL DLSVHKK  C  DSEGKEFKE    H    Q      A       KK KPTTCML QKVLLNEYNG  900 hRIZ       I LP ENPAD C TRSPSPCKS LEAQPDP LG P SCFPAPTV ES IP M  PS SP LQT FSLS   958
rRIZ       VSLP E TPE V TRSPSPCKS PDTQPDP LG P SSCSVPT  ES IP F M CPS SP LQT SLS   949
Consensus    LP   E     TRSPSPCKS     QPDP LG P S      PT ES             PS SP LQT  SLS   960 hRIZ       SGQLPPLL P T PSSPPPCP PVLTVATPPP PLLPTVPLPA PSS ASPH FC PSP SN TAQ  1018
rRIZ       SGQLPPLL P T PSSPPPCP PVLTVATPPP PLLPTVPL H PSS ASPQ CC PSP SN TAQ  1009
Consensus  SGQLPPLL P   PSSPPPCP PVLTVATPPP PLLPTVPL    PSS  ASP   C  PSP SN TAQ  1020 hRIZ       SPLPILSPTV SPSPSPIPPV EPLMSAASPG PPTLSSSSSS SSS SFS S SS SP PPP  1078
rRIZ       SPLPILSPTV SPSPSPIPPV EPLMSAASPG PPTLSSSSSS SSS FS S S S SF SP P -  1067
Consensus  SPLPILSPTV SPSPSPIPPV EPLMSAASPG PPTLSSSSSS SSS  S  S  S  S   SP P    1080
```

FIG. 10C

```
hRIZ         LSAISSVVSS GDNLEASLPM ISFKQEE EN EGLKPEEPQ SAAEQVVQ ETF KNF CN     1138
rRIZ         LSAVSSVVSS GDNLEASLPA VTFKQEE ES EGLKPVEEAP FACCQS VVQ ETFEKNF CN   1126
Consensus    LSA SSVVSS GDNLEASLP. .  FKQEE E.  EGLKP.EE.  .A. Q . VVQ . ETF. KNF. CN  1140 hRIZ         VCESPFLSIK DLTKHLSIHA EEWPFKCEFC VQLFKQKTDL SEHRFLLHGV GNIFVCSVCK    1198
rRIZ         VCESPFLSIK DLTKHLSJHA EEWPFKCEFC VQLFKQKTDL SEHRFLLHGV GNIFVCSVCK    1186
Consensus    VCESPFLSIK DLTKHLS HA EEWPFKCEFC VQLFK KTDL SEHRFLLHGV GNIFVCSVCK    1200 hRIZ         KEFAFLCNLQ QHQRDLHPDK VCTHHEFESG TLRPQNFTDP SKA VEHMCS LPEIPLETSK    1258
rRIZ         KEFAFLCNLQ QHQRDLHPDE VCTHHEFESG TLRPQNFTDP SKAVVEHMFS LPEEPLETSR    1246
Consensus    KEFAFLCNLQ QHQRDLHPD. VCTHHEFESG TLRPQNFTDP SKA. VEHM S LPE.PLETS.    1260 hRIZ         EEEGLNDSSE ELYTTIKIMA SGIKTKDPDV RLGLNQHYPS FKPPPFQYHH RNPMGIGVTA    1318
rRIZ         EEEHLNDSSE ELYTTIKIMA SGIKTKDPDV RLGLNQHYPS FKPPPFQYHH RNPMGIGVTA    1305
Consensus    EEE LNDSSE ELYTTIKIMA SGIKTKDPDV RLGLNQHYPS FKPPPFQYHH RNPMGIGVTA    1320 hRIZ         TNFTTHNIPQ TFTTAIRCTK CGKGVDNMPE LHKHILACAS ASDKKRYTPK KNPVPLKQTV    1378
rRIZ         TNFTTHNIPQ TFTTAIRCTK CGKGVDNMPE LHKHILACAS ASDKKRYTPK KNPVPLKQTV    1365
Consensus    TNFTTHNIPQ TFTTAIRCTK CGKGVDNMPE LHKHILACAS ASDKKRYTPK KNPVPLKQTV    1380 hRIZ         QPKNGVVVLD NSGKNAFRRM GQPKRLNFEV ELGKMSENKL KLNALKKKNQ LVQKAILQKN    1438
rRIZ         QPKNGVVVLD NSGKNAFRRM GQPKRLTFIV ELIKMSPNKL KLSALKKKNQ LVQKAILQKN    1425
Consensus    QPKNGVVVLD NSGKNAFRRM GQPKRL F V EL KMS NKL KL ALKKKNQ LVQKAILQKN    1440
```

FIG. 10D

```
hRIZ      KSAKQKADLK  NAQESSHIC  PYCNREFTYI  GSLNKHAAFS  CPKKPLSPHK  KVSHSSKKG  1498
rRIZ      RAAKQKADLR  DTSEPSSHIC  PYCHREFTYI  GSLNKHAAFS  CPKKPLSPSK  KVSHSSKKG  1485
Consensus  .AKQKADL.  ...E..SSHIC  PYC.REFTYI  GSLNKHAAFS  CPKKPLSP.K  KVSHSSKKG  1500 hRIZ      GHSSPASSDK  NSNSNHRRRT  ADEEIKMQSM  QIPLGKTRAR  SGGPTQVFLP  SSSFRSTQNV  1558
rRIZ      GHSSSSSSDR  NSSCHRRRT  ADEIEIKMQST  QNPLGKTRAR  SHGPTQASLP  SSSFRSQNV   1545
Consensus  GH.S...SSD.  NS.....  .RRRT  AD..EIKMQS.  Q.PLGKTRAR  S..G..  .LP  SSSFRS.QNV  1560 hRIZ      KFAASVKSKK  PSSSSLRNSS  PIRMAKITHV  EGKKPKAVAK  HSAQLSSKT  SRELHVRVQK   1618
rRIZ      KFAASVKSKK  PSSSSLRNSS  PIRMAKITHV  EGKKPKAVAK  SHSAQLSSKG  SRELHVRVQK   1605
Consensus  KFAASVKSKK  .SSSSLRNSS  PIRMAKITHV  EGKKPKAVAK  .HSAQLSSK.  SR.LHVRVQK   1620 hRIZ      SKAVIQSKFT  LASKRTDRF  NIKSRERSGG  PITRSLQLAA  AADLSENKRE  DSAKQELKD   1678
rRIZ      SKAVIQSKTA  LASKRTDRF  IVKSRERSGG  PITRSLQLAA  AADLSESFRE  DSSARHELKD   1665
Consensus  SKAV.QSK..  LASK.RTDRF  ..KSRERSGG  P.TRSLQLAA  AADLSE...RE  D.SA..ELKD  1680 hRIZ      FSYSLRLASR  CSPPAAFYIT  RQTRKVKAHA  AAQFQGPFHK  E           1719
rRIZ      FSYSLRLASR  CGSSTAFYIT  RQCRKVKAHA  ATRFQGPFHK  EX          1707
Consensus  FSYSLRLASR  C.......  A.YIT  RQ.RKVKA.A  A..FQGPF.K  E.       1722
```

FIG. 10E

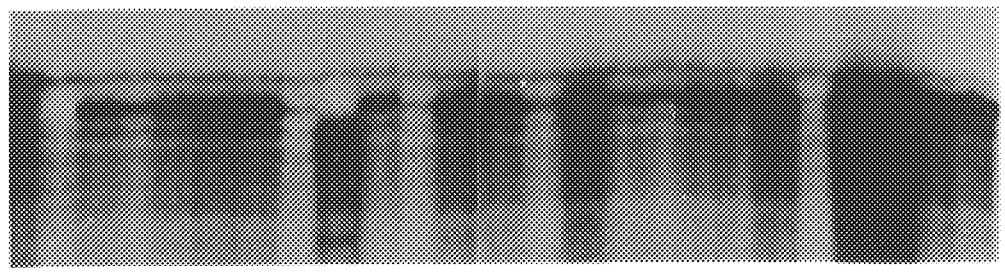
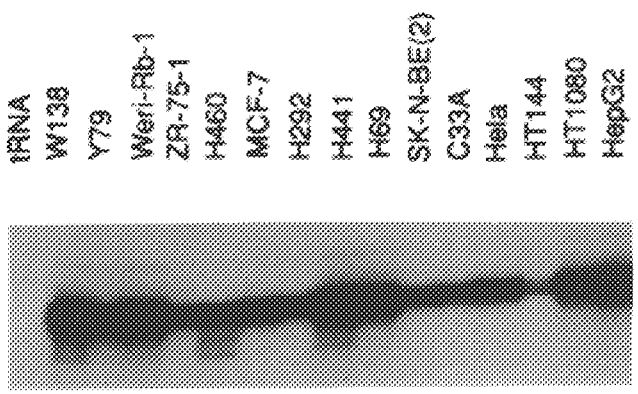
FIG. 12

NUCLEIC ACID MOLECULES ENCODING RETINOBLASTOMA PROTEIN-INTERACTING ZINC FINGER PROTEINS

This application is a continuation of U.S. Ser. No. 08/399,411, filed Mar. 6, 1995, which is a continuation-in-part of U.S. Ser. No. 08/292,683, filed Aug. 18, 1994, now abandoned, the entire contents of which are incorporated herein by reference.

This invention was made in part with government support under CA57496, awarded by the National Institutes of Health, and 5T30 CA30199, awarded by the Cancer Center Core. The United States government has certain rights in this invention.

BACKGROUND OF THE INVENTION

1. Field of the Invention

This invention relates to the field of molecular biology and, in particular, to nucleic acid molecules encoding an Rb-interacting zinc finger protein.

2. Background Information

The retinoblastoma Rb protein is known to play a key role in controlling normal cell proliferation and differentiation. The ability of a cell to divide requires the cell to pass through the various phases of the cell cycle. Although Rb is believed to keep normal cells from dividing by maintaining them in a phase of the cell cycle known as $G_1$ or $G_0$, the precise mechanism underlying Rb function is unknown.

The role that Rb plays in controlling cell growth makes it an attractive target for promoting the growth of tissues that normally do not grow because of the action of Rb. For example, cardiac muscle tissue or nerves that have lost function due to cell death are not usually repaired by subsequent proliferation of the remaining live cells. Thus, a method to block the growth controlling function of Rb can be useful for inducing tissue repair in situations of cardiac or neural cell death.

Rb also is known as a tumor suppressor since the abnormal growth of a cancer cell can result from inactivation of Rb protein. Such inactivation can occur either due to a mutation or to inactivation of Rb protein subsequent to binding a viral oncoprotein, a product of an oncogenic tumor virus. A particular region in Rb called the Rb pocket appears to be critical for its growth controlling function since Rb inactivation by mutation or by oncoprotein binding impacts this region.

The importance of the Rb pocket in the functioning of Rb and the understanding that viral oncoproteins can regulate Rb by binding the pocket suggest that there may be normal cellular proteins that can regulate the function of Rb by binding the pocket. The identification of such proteins will provide new approaches to regulate the control of cell proliferation mediated by Rb in diseases such as those that involve loss of cardiac or neural function or in the control of cancer. Thus, a need exists to identify proteins that can bind to and regulate Rb. The present invention satisfies this need and provides related advantages as well.

SUMMARY OF THE INVENTION

The present invention provides substantially purified mammalian Rb-interacting zinc finger proteins (RIZ), including for example, human RIZ and rat RIZ. In addition, the invention provides active fragments of a RIZ such as the sequences EIRCEEKPEDL (SEQ ID NO: 6) and EIRCDEKPEDL (SEQ ID NO: 91), which bind Rb. The invention also provides antibodies that can specifically bind to a RIZ or a mutant RIZ The invention further provides nucleic acid molecules encoding mammalian RIZ and active fragments thereof, vectors containing the nucleic acid molecules and host cells containing the vectors. In addition, the invention provides nucleotide sequences that can specifically hybridize to a nucleic acid molecule encoding a RIZ or a mutant nucleic acid molecule encoding a RIZ.

The invention also provides a screening assay useful for identifying agents that can effectively alter the association of a RIZ with a second molecule such as Rb or can effectively alter the activity of a RIZ. By altering the association of a RIZ with a second molecule or altering the activity of a RIZ, an effective agent can modulate a function of a cell such as cell proliferation.

The invention further provides methods for promoting the growth of a cell such as a neural cell or cardiac muscle cell by contacting the cell with an effective agent. For example, cell growth can be promoted by introducing into a cell an effective agent such as an expression vector having an expression control sequence operably linked to a nucleotide sequence encoding an active fragment of a RIZ.

The invention also provides methods of detecting a RIZ in a sample by detecting the presence of the RIZ protein or of a nucleic acid molecule encoding the RIZ. Such methods can be used to diagnose a pathology characterized by an increased or decreased level of expression of a RIZ in a cell or by expression of a mutant RIZ. Such a method also can be used to diagnose a pathology characterized by a mutant nucleic acid molecule encoding a RIZ.

The invention further provides methods useful for isolating Rb tumor suppressor protein or a mutant Rb from a sample. For example, Rb can be isolated from a sample by affinity chromatography using a RIZ or a RIZ active fragment such as the sequences EIRCEEKPEDL (SEQ ID NO: 6) or EIRCDEKPEDL (SEQ ID NO: 91).

BRIEF DESCRIPTION OF THE FIGURES

Figure 1A-1:
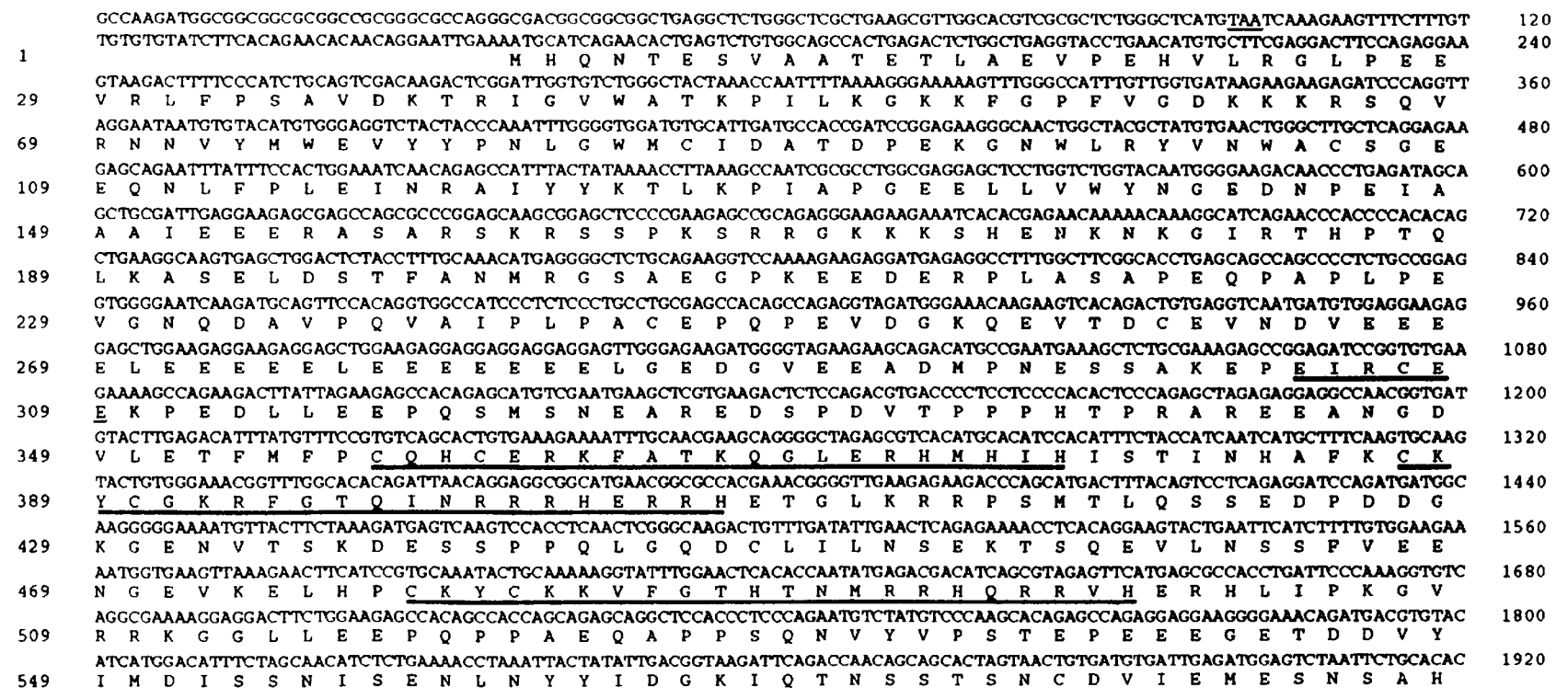
Figure 1A-2:
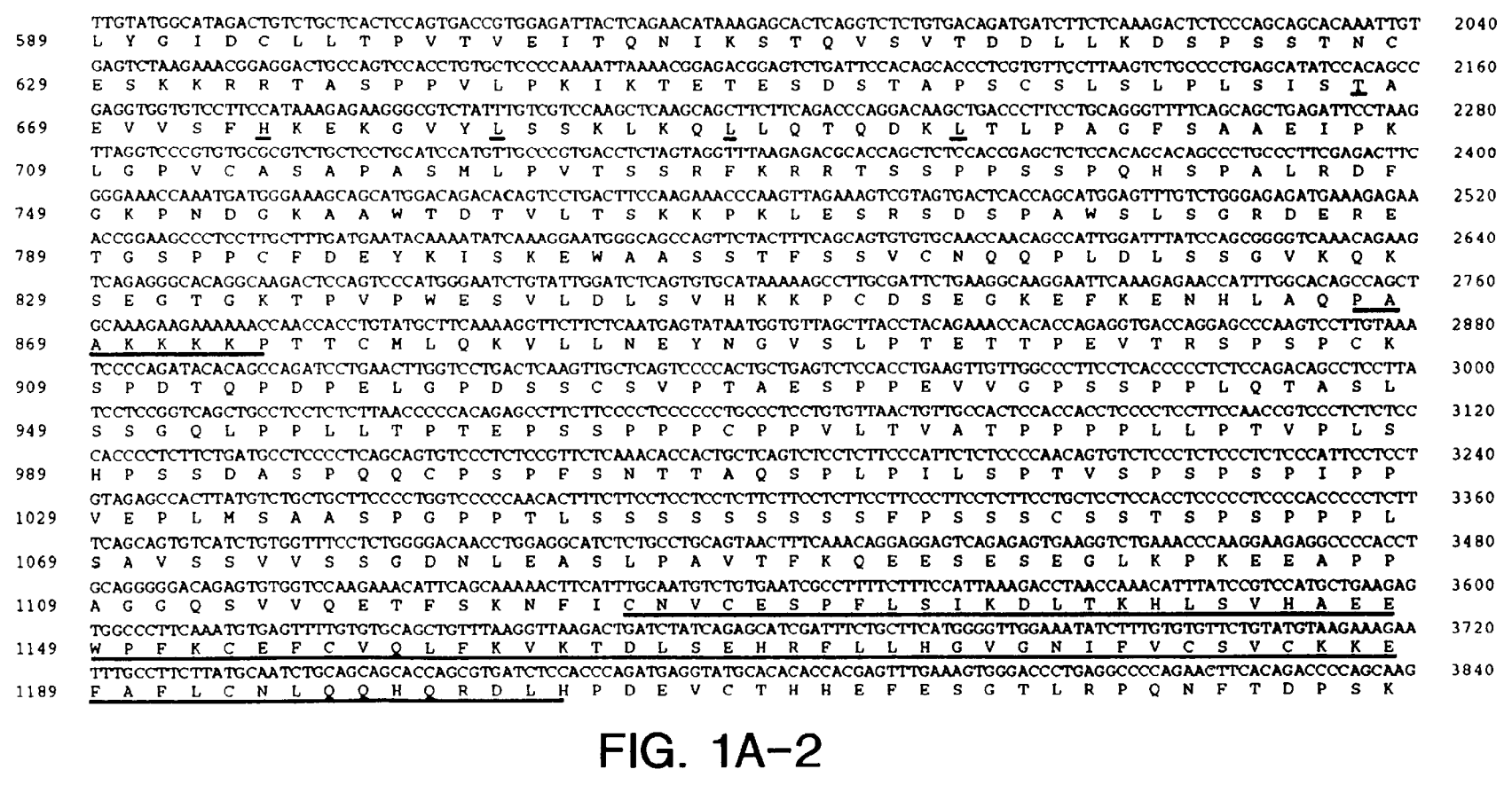
Figure 1A-3:
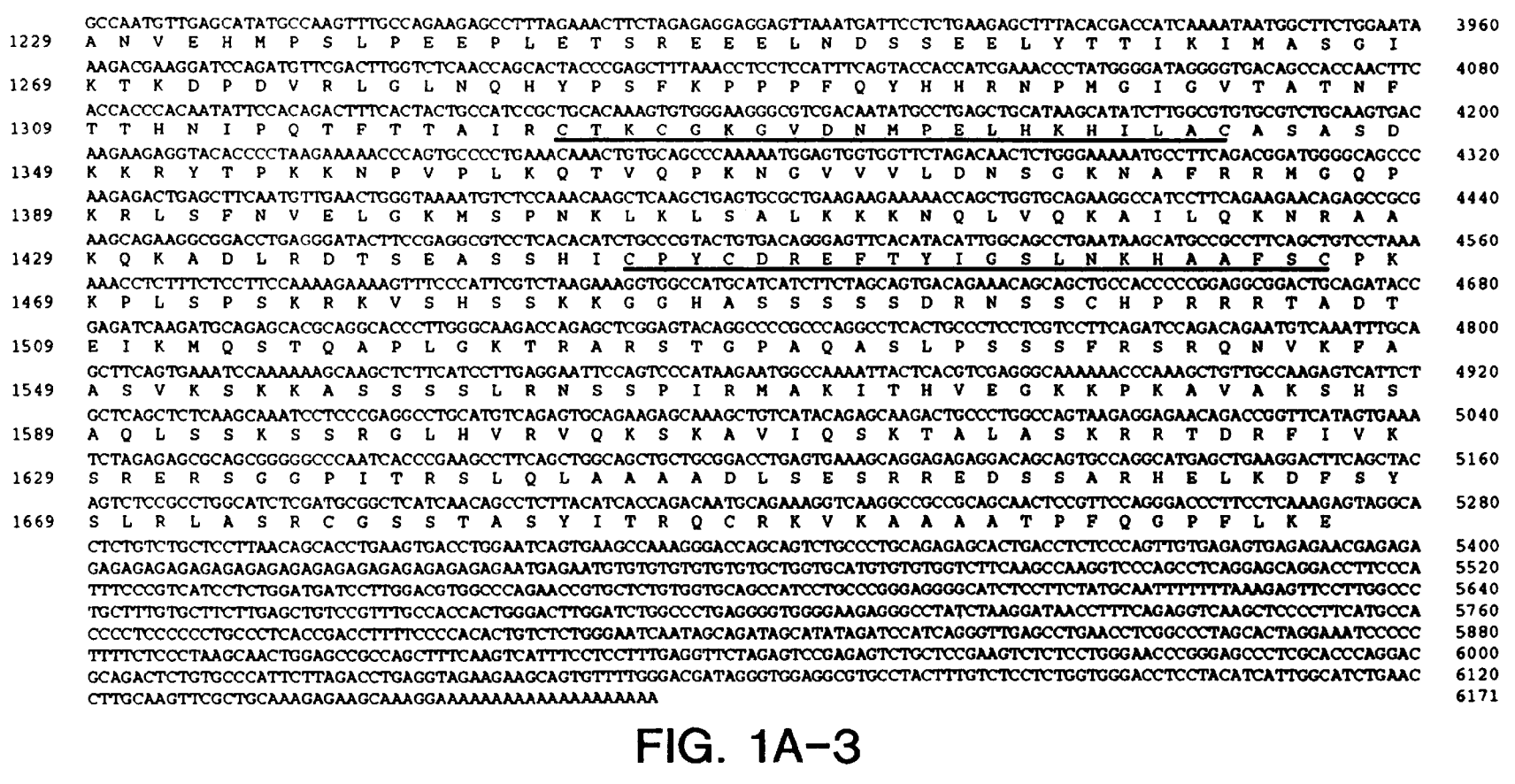

FIG. 1 shows the cDNA sequence (SEQ ID NO: 1) and the deduced amino acid (a.a.) sequence of full-sized rat RIZ protein (SEQ ID NO: 2). Numbers at right indicate nucleotide position; numbers at left indicate amino acid position. The following features are underlined: an upstream in-frame stop codon (nucleotide position 110-112), a cr2 core motif (a.a position 304-309), 8 zinc fingers (a.a. positions 357-377, 478-499, 387-407, 1125-1303 (finger 4–6), 1323-1343 and 1445-1466), putative leucine zipper (a.a. position 667-695)) and a putative nuclear localization signal (a.a. positions 867-874). Single letter amino acid symbols are used.

FIGS. 2A to 2C show homologies between rat RIZ and various other proteins. Single letter amino acid symbols are used. Numbers indicate amino acid positions in relation to the complete protein.

FIG. 2A compares RIZ amino acid sequences with various E1A sequences. E1A sequences of the different strains of adenoviruses are from Kimelman et al., *J. Vir.*, 53:399–409 (1985), Moran and Mathews, *Cell*, 48:177–178 (1987), and Ishino et al., *Vir.*, 165:95–102 (1988). Identical or closely related residues are boxed. Single letter amino acid symbols are used. Sequence domains, RIZ CR1 (SEQ ID NO: 79) Ad2E1A cr1 (SEQ ID NO: 44), Ad5 cr1 (SEQ ID NO: 45), Ad7 cr1 (SEQ ID NO: 46), Ad12 cr1 (SEQ ID NO: 47), EA7 cr1 (SEQ ID NO: 48), Ad40 cr1 (SEQ ID NO: 49), RIZ cr2 (SEQ ID NO: 65), Ad2E1A cr2 (SEQ ID NO: 66), Ad5 cr2 (SEQ ID NO: 67), Ad7 cr2 (SEQ ID NO: 68), Ad12 cr2 (SEQ ID NO: 69), EA7 cr2 (SEQ ID NO: 70), Ad40 cr2 (SEQ ID NO: 71), RIZ ce1 (SEQ ID NO: 72), Ad2E1A ce1 (SEQ ID NO: 73), Ad5 ce1 (SEQ ID NO: 74), Ad7 ce1 (SEQ ID NO: 75), Ad12 ce1 (SEQ ID NO: 76), EA7 ce1 (SEQ ID NO: 77) and Ad40 ce1 (SEQ ID NO: 78) are shown.

FIG. 2B shows RIZ putative SH3 and SH3-binding domains. FIG. 2B, panel a: Sequence comparison of RIZ (SEQ ID NO: 80) with other known SH3 domain-containing proteins (Lowenstein et al., Cell, 70:431–442 (1992)). Identical or closely related. residues are boxed and the phosphate-binding loop in RIZ (a.a. position 744-763) is underlined. Sequences from GRB2 N-terminus (SEQ ID NO: 50), GRB2 C-terminus (SEQ ID NO: 51), P85 (SEQ ID NO: 52), v-abl (SEQ ID NO: 53), c-src (SEQ ID NO: 54), GAP (SEQ ID NO: 55), PLC (SEQ ID NO: 56) and v-crk (SEQ ID NO: 57) are shown. FIG. 2B, panel b: A RIZ putative SH3-binding motif compared with SH3 motifs from known SH3-binding proteins (Ren et al., Science 259:1157–1161 (1993)). Identical or closely related residues are boxed. Sequences from RIZ (SEQ ID NO: 81), with a.a. positions 977-990 and 1020-1044 underlined, Formin (SEQ ID NO: 58), 3BP1 (SEQ ID NO: 59), 3BP2 (SEQ ID NO: 60) and m4mAChR (SEQ ID NO: 61) are shown.

FIG. 2C shows homology between RIZ and PRDI-BF1 proteins (Keller and Maniatis, Genes Devel., 5:868–879 (1991)). FIG. 2C, panel a: Alignment of RIZ zinc fingers 4 to 6 (SEQ ID NO: 82) with PRDI-BF1 zinc fingers 1 to 3 (SEQ ID NO: 62). A consensus sequence is shown with nonidentical residues indicated by dots. Potential DNA contact residues are marked by stars (Pavletich and Pabo, Science, 252:809–817 (1991)). FIG. 2C, panel b: Amino terminal homology between RIZ (a.a. position 39-115; SEQ ID NO: 83 a.a. position 116-145: SEQ ID NO: 84) and PRDI-BF1 (a.a. position 60-139: SEQ ID NO: 63 and a.a. position 140-169: SEQ ID NO: 64)). A consensus sequence is shown with nonidentical residues indicated by dots.

FIG. 5A: Purified glutationine S-transferase fusion protein containing a C-terminal RIZ fragment (a.a. position 245-573) was tested for binding to $^{35}$S-labeled Rb wild-type (wt-Rb) and to various deletion mutants (lanes 2–5) as shown in FIG. 5B Wild-type (wt) full length Rb (A9), Cys to Phe mutation of full length Rb (H209), Rb deletion mutants from amino acid positions 515-619 (NM), 585-697 (PP) and 804-928 (B3) are shown.

FIG. 5B: Schematic map of Rb wild-type (wt-Rb) and Rb deletion mutants. The two sub-domains of the Rb pocket are represented by black boxes. Mutants that bind a glutathionine S-transferase (GST) RIZ (a.a. position 245-573) are indicated by a "+" sign. p56 Rb: 56 kD fragment of Rb from a.a. position 379-928.

FIG. 7A: SDS-PAGE (10% acrylamide) and Coomassie blue staining of GST; GSTZ13: GST-RIZ (a.a. position 245-573 containing zinc fingers 1–3); and GSTZ46: GST-RIZ (a.a. position 1114-1260 containing zinc fingers 4 to 6). KD indicates the migration of molecular weight markers.

FIG. 7B: Binding of $^{32}$P-labeled rat genomic DNA to GST, GSTZ13 and GSTZ46 in the presence of zinc ions.

FIG. 7C: As in FIG. 6B, except zinc ions were not added.

FIG. 8A: SDS-PAGE (10% acrylamide) and Coomassie blue staining of purified GST-G: GST-RIZ (760-949: RIZ GTPase domain fused C-terminal to glutathionine S-transferase).

FIG. 8B: $^{32}$P-GTP binding by GST (lane 1) and GST-G (lanes 2–6). Binding conducted in the absence or presence (lanes 3–6) of excess unlabeled nucleotides as indicated.

FIG. 9 shows the nucleotide sequence (SEQ ID NO: 3) and deduced amino acid sequence (SEQ ID NO: 4) of full-length human RIZ. Single letter amino acid symbols are used. Numbers at right indicate the nucleotide position.

FIG. 10 compares the complete human RIZ amino acid sequence (indicated as hRIZ; SEQ ID NO: 4) with the complete rat RIZ amino acid sequence (indicated as rRIZ; SEQ ID NO: 2). A consensus sequence is shown. Single letter amino acid symbols are used. Amino acids that are identical in hRIZ and rRIZ are shown as a ".".

FIG. 11A presents a northern blot of adult mRNA probed with $^{32}$P-labeled rat RIZ (1.9 Kb fragment representing a.a. position 245-883). Att-20 is a mouse pituitary cell line.

FIG. 11B presents an RNase protection experiment using RNA from a 16 day fetal rat (E16) and from an adult rat probed with $^{32}$P-labeled rat RIZ (representing a.a. position 463-574).

FIG. 12 presents an RNase protection experiment using mRNA from various human cell lines and from a rat cell line (indicated as GC). The 321 base pair marker (321 b) indicates protection of $^{32}$P-labeled rat RIZ (a.a. position 457-579) while the 130 base pair marker (130 b) indicates protection of Actin.

DETAILED DESCRIPTION OF THE INVENTION

Figure 3:
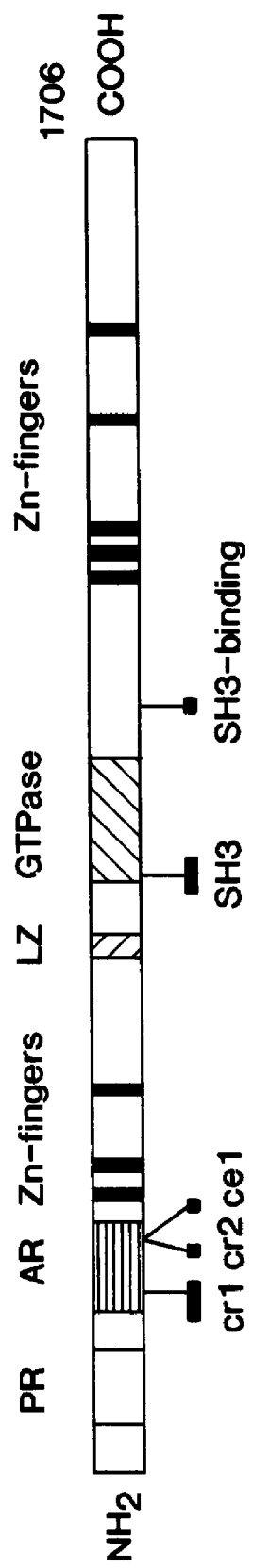
FIG. 3: Schematic representation of RIZ domain structure. PR: domain homologous to PRDI-BF1; AR: acidic region or E1A-related region; LZ: leucine-zipper; cr1 and cr2: conserved regions 1 and 2; ce1: common epitope 1. Zinc (Zn—) fingers, GTPase and SH3 and SH3-binding domains also are shown.

The present invention provides a novel mammalian Rb-interacting zinc finger protein, designated RIZ. RIZ is a nuclear phosphoprotein that acts as a cell differentiation factor. RIZ can modulate a function of a cell by binding to retinoblastoma (Rb) protein, which is involved in regulating cell proliferation.

Rb is a nuclear phosphoprotein of 110 kiloDaltons (kD) that can bind DNA and is expressed in all tissue types examined thus far. The complete absence of Rb function is associated with the development of childhood retinoblastoma. In addition, Rb is mutated in a variety of cancer types, including various carcinomas and sarcomas, indicating a role indicating a role for Rb in oncogenesis. Expression of exogenous Rb in various types of tumor cells suppresses the tumor phenotype (for review, see Lee et. al., *J. Cell Biochem.* 38:213–227 (1988)).

The function of Rb at the biochemical level in a cell is poorly understood. Rb is present in phosphorylated and unphosphorylated forms in the cell. The phosphorylation status of Rb oscillates during the cell cycle with the hypophosphorylated form correlating with the maintenance of the cell in $G_1$ phase of the cell cycle. Thus, the state of phosphorylation plays an important role in Rb function.

Rb protein binds to several DNA tumor viral oncoproteins, including the adenoviral E1A protein, the SV40 large T antigen and the E7 protein of the human papilloma virus (DeCaprio et al., *Cell* 54:275–283 (1988); Whyte et al., *Cell* 56:67–75 (1989); Dyson et al., *Science* 243:934–937 (1989)). The oncoproteins E1A and large T antigen bind to a similar region of Rb protein known as the Rb pocket, which is formed by two non-contiguous amino acid sequences in the protein (Hu et al., *EMBO J.* 9:1147–1155 (1990); Huang et al., *EMBO J.* 9:1815–1822 (1990); Kaelin et al., *Mol. Cell. Biol.* 10:3761–3769 (1990), each of which is incorporated herein by reference). The binding to Rb by these viral oncoproteins can alter normal Rb function.

As disclosed herein, RIZ is a normal cellular protein that binds to the Rb pocket. RIZ binding to Rb is unlike that of an oncoprotein since RIZ functions as a differentiation factor that helps to maintain cells in the $G_0$ or $G_1$ phases of the cell cycle. This is based on the fact that RIZ can bind to Rb in the cell, the latter being a known regulator of cell proliferation and differentiation, and that RIZ is structurally related to a known differentiation and transcription factor PRD1-BF1/Blimp-1 (Huang, *Cell:*78, 9 (1994)).

The ability to regulate cell growth has important implications for various human diseases or conditions. Cancer is an example of a disease that results from a breakdown in the ability of a cell to regulate its growth. In contrast, there are examples such as cardiac muscle cells and neural cells where the maintenance of cell growth control contributes to a sustained loss in organ or tissue function following a disease or injury that resulted in cell death. In these situations, the compromised tissue or organ fails to regenerate fully because the remaining live cells are incapable of undergoing proliferation to replace the lost function.

Heart disease provides an example where cardiac muscle cell death due to ischemia or other injury results in a loss of heart function. Generally, proliferation of the remaining live cardiac cells to regenerate the lost cardiac muscle function does not occur in adults. Although myocardial cell proliferation can occur during embryonic and neonatal development, this capacity to proliferate is lost soon after birth. In a similar manner, neural damage resulting from trauma or disease is not usually followed by regeneration of neural function because the remaining neural cells are maintained in the $G_1$ phase of the cell cycle. Transcriptional regulators such as Rb play an important role in controlling whether cells can enter the cell cycle and proliferate. In contrast, inactivation of Rb is involved in the unregulated growth of a cancer cell.

As disclosed herein, RIZ can bind to Rb and can regulate the ability of Rb to maintain cells in the $G_1$ phase of the cell cycle. Methods that affect the ability of Rb and RIZ to associate or that affect the activity of a RIZ can be used to modulate cell proliferation. RIZ can regulate the growth of normal adult cardiac muscle cells by preventing the cells from proliferating following cardiac muscle cell death. RIZ can function to maintain cells in $G_1$ by interacting with Rb through the cr2 domain of RIZ. In addition, the functional differentiation state of a cell, which involves maintenance of a cell in $G_1$, is affected, in part, through the action of other RIZ domains such as the PR domain, GTP binding domain and the zinc finger domains.

The present invention provides a substantially purified RIZ protein that binds to Rb. The invention provides, for example, human RIZ having substantially the amino acid sequence shown in FIG. 9 (SEQ ID NO: 4) and rat RIZ having substantially the amino acid sequence shown in FIG. 1 (SEQ ID NO: 2).

As used herein, the term "substantially the amino acid sequence" means a sequence that is similar to the disclosed amino acid sequence. For example, an amino acid sequence that is substantially similar to human RIZ (SEQ ID NO: 4) or to rat RIZ (SEQ ID NO: 2) can have one or more amino acid additions, deletions or substitutions that do not substantially alter the ability of the encoded protein to function like a RIZ. In view of this definition, it should be recognized, for example, that the rat RIZ sequence shown in FIG. 1 (SEQ ID NO: 2), which is 84% homologous to the human RIZ sequence has substantially the amino acid sequence of human RIZ (SEQ ID NO: 4). Similarly, the rat RIZ cr2 sequence EIRCEEKPEDL (SEQ ID NO: 6) is substantially the sequence of the human RIZ cr2 motif, EIRCDEKPEDL (SEQ ID NO: 91). The latter two sequences differ by a single conservative substitution of a Glu in the rat for an Asp in the human in the residue following the Cys.

As used herein, the term "substantially purified" means a protein that is in a form that is relatively free from contaminating lipids, proteins, nucleic acids or other cellular material normally associated with a protein in a cell. A substantially purified human RIZ protein can be obtained, for example, using well known biochemical methods of purification or by expressing a recombinant nucleic acid molecule encoding a RIZ such as the nucleic acid molecule shown as SEQ ID NO: 3. In addition, an amino acid sequence consisting of at least a portion of the amino acid sequence of SEQ ID NO: 4 can be chemically synthesized or can be produced by expressing a portion of the nucleotide sequence shown as SEQ ID NO: 3.

As used herein, the terms "protein" or "polypeptide" are used in the broadest sense to mean a sequence of amino acids that can be encoded by a cellular gene or by a recombinant nucleic acid sequence or can be chemically synthesized. In some cases, the term "polypeptide" is used in referring to a portion of an amino acid sequence encoding a full length protein. An active fragment of a RIZ is an example of such a polypeptide. A protein can be a complete, full length gene product, which can be a core protein having no amino acid modifications, or can be a post-translationally modified form of a protein such as a phosphoprotein, glycoprotein, proteoglycan, lipoprotein or nucleoprotein.

Figures 1, 2, 2A, 2B:
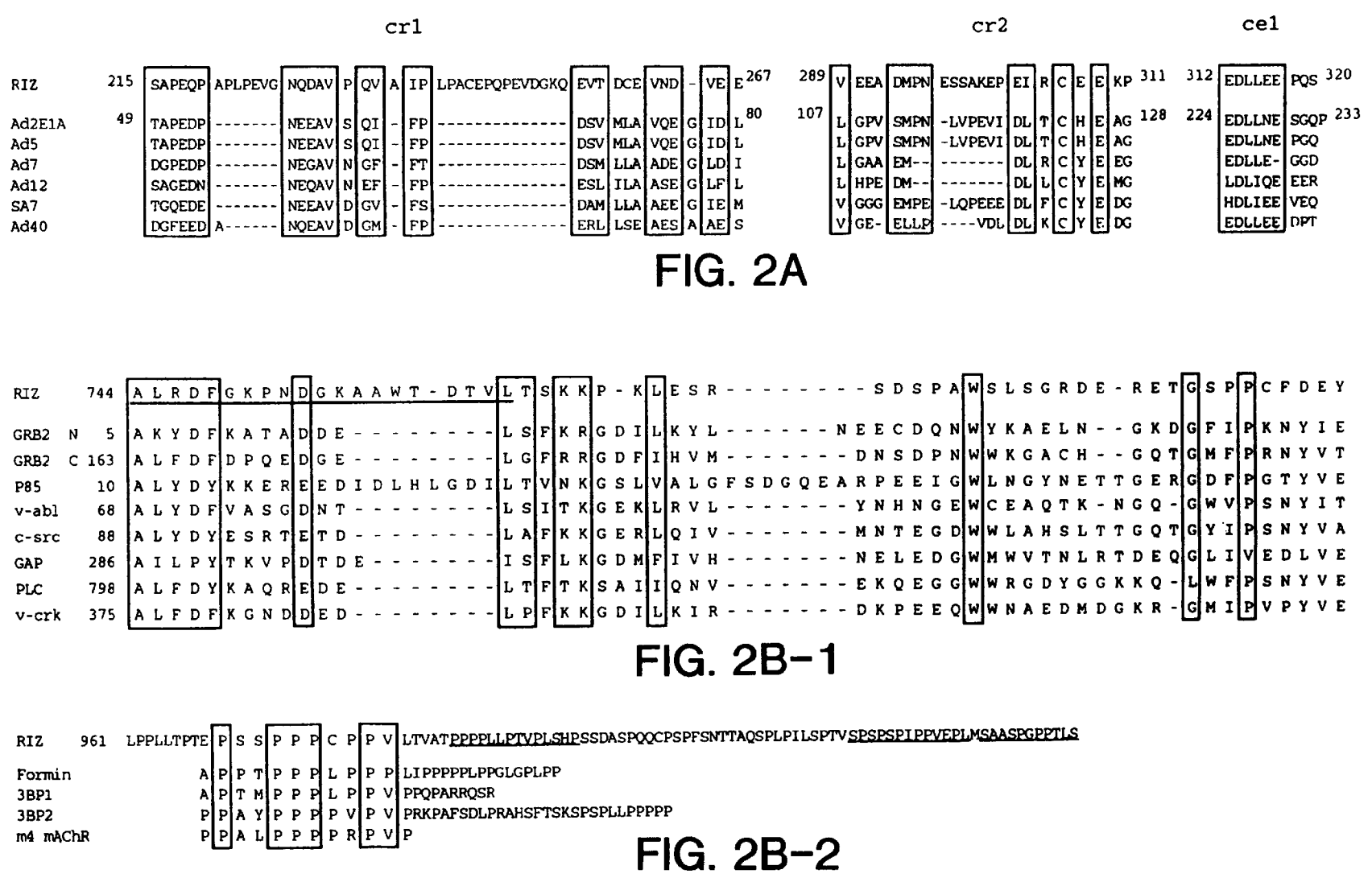

The full length rat RIZ protein contains 1706 amino acids and has a calculated molecular mass of 187,437 Daltons (FIG. 1; SEQ ID NO: 2). The rat RIZ contains a 6 residue E1A related motif (a.a. position 304-309) known as the cr2 core motif, which is related to the LXCXE (SEQ ID NO: 5)

core motif of E1A. Additional E1A related motifs in RIZ include the cr1 motif and a C-terminal motif designated "conserved epitope 1" (ce1) because of its antigenic relationship to a homologous motif in the C-terminus of E1A (see Example II). Rat RIZ also contains 8 zinc fingers, a putative GTPase domain, a putative leucine zipper and a putative nuclear localization signal (FIGS. 1 and 3).

All three E1A-related motifs in rat RIZ are located in an acidic region that consists of about 150 residues (AR; FIG. 3) and resembles a highly acidic region in the E1A 12S protein (Moran and Matthews, Cell, 48:177–178 (1987)). In both RIZ and E1A, the related motifs are arranged in the same order and the spacing between cr1 and cr2 is similar. However, the ce1 motif is located much closer to cr2 in RIZ than in E1A (see FIG. 2A)

The rat RIZ protein sequence contains known GTPase motifs (Table 1) organized in an orderly fashion and separated by consensus spacings (Bourne et al., Nature 349:117–127 (1991)). The G1 or Walker type-A motif (GX$_4$GKX$_7$(I/V); SEQ ID NO: 14), which represents the phosphate-binding loop (P-loop), occurs at a.a. position 749 in RIZ and identifies a guanine or adenine nucleotide-binding site (Walker et al., EMBO J. 1:945–951 (1982); Saraste et al., Trends Biochem. Sci. 15:430–434. (1990)). The sequence around residue 749 also is similar to the src homology 3 (SH3) domain conserved in many non-receptor tyrosine kinases and other proteins (FIG. 2B panel a); Pawson and Gish, Cell 71:359–362 (1992)). RIZ also contains a proline-rich region that has several potential SH3-binding motifs (FIG. 2B, panel b); Renet al., Science, 259:1157–1161 (1993)).

TABLE 1

Putative GTPase Domain in RIZ

| | G1 | G2 | G3 | G4 |
|---|---|---|---|---|
| Consensus | GXXXXGK$_T$$^S$ (22) | D(X)$_n$T (23) | DXXG (24) | TQ$^{NKXD}$ |
| RIZ | $^{749}$GKPNDGKA (85) | $^{785}$DERET (86) $^{796}$D (X)$_{12}$T (87) $^{821}$D (X)$_{11}$T (88) | $^{853}$DSEG (89) | $^{912}$TQPD (90) |
| FtsZ | $^{106}$GGTGTGAA (25) (27) | $^{122}$DLGILT (26) $^{158}$DSLIT (30) $^{212}$DVRT (28) | $^{180}$DAFG (29) $^{253}$DLSG | $^{295}$TSLD (31) |
| CDC42 | $^{10}$GDGAVGKT (32) | $^{32}$YVPT (33) | $^{57}$DTAG (34) | $^{115}$TQ1D (35) |
| DOG-SR2 | $^{419}$GVNGVGKS (36) | $^{455}$DT | $^{516}$DTAG (34) | $^{584}$TKFD (37) |
| EF-Tu | $^{13}$GHVDHGKT (38) | $^{50}$D (X)$_{10}$T (39) | $^{80}$DCPG (40) | $^{135}$NKCD (41) |
| Ha-Ras | $^{10}$GAGGVKS (42) | $^{33}$DPT (43) | $^{57}$DTAG (34) | $^{116}$NKCD (41) |

Comparison of the putative G1–G4 GTPase domains in the RIZ protein sequence with the conserved sequence motifs in the GTPase superfamily (single letter code and X is any residue, Bourne et al., 1991). For reference to the listed sequences (except RIZ and FtsZ) see Bourne et al; (1991). For reference to FtsZ, see Ray Chaudhuri and Park (1992)
*Number in parenthesis below each sequence indicates SEQ ID NO:.

Sequence homology shows that a mammalian RIZ protein contains eight zinc-finger motifs organized as two widely separated clusters in the N-terminal (fingers 1 to 3) and C-terminal (fingers 4 to 6) regions (FIG. 3). A search of the National Biomedical Research Foundation protein database revealed that the most significant homology for zinc fingers was for RIZ fingers 4 to 6, which are about 39% (33 out of 85) identical to fingers 1 to 3 of the human transcriptional repressor PRDI-BF1 (see FIG. 2C; Keller and Maniatis, supra, 1991). RIZ also contains a region of about 100 residues near the N-terminus that is designated "PR" because it is 42% homologous with a similar N-terminal region from PRDI-BF1 (see FIG. 2C) and Blimp-1 (Huang, supra, 1994).

Human RIZ was cloned from human cDNA and genomic DNA libraries using the rat RIZ cDNA as a hybridization probe. The human RIZ cDNA (SEQ ID NO: 3) encodes a polypeptide having 1719 amino acid residues (see FIG. 9 for a.a.; SEQ ID NO: 3). The human RIZ gene coding region is encoded by eight exons and is located on chromosome 1p36 (see Example VI).

Allelic variants of the human RIZ gene are disclosed herein. The RIZ E283 allele contains a Glu residue at a.a. position 283, while the RIZ D283 allele contains an Asp residue at a.a. position 283 (SEQ ID NO: 4). The basis for the amino acid difference is a single nucleotide change of T$_{849}$ in the RIZ D283 to an A$_{849}$ in RIZ E283. The RIZ D283 allele is estimated to occur two times more frequently in the human population than the RIZ E283 allele.

The deduced rat and human RIZ amino acid sequences are 84% homologous. Both the rat and human RIZ proteins have similar sequence motifs including cr1, cr2, ce1, zinc finger, SH3, SH2 and a nuclear localization signal. Both rat and human RIZ proteins are similar in size; rat RIZ contains 1706 amino acids and has a calculated molecular weight of 187,437 Daltons while human RIZ contains 1719 amino acids and has a calculated molecular weight of 188,894 Daltons. In addition, a rabbit antiserum produced against rat RIZ (see Example II) crossreacts with human RIZ.

RIZ is expressed primarily in the cell nucleus. RIZ mRNA is expressed primarily in cells of neuroendocrine origin and is expressed in greater amounts in the fetus than in the adult (see FIGS. 10 and 11). RIZ is expressed in rat cells as a 250 kD phosphoprotein.

Figure 9A:
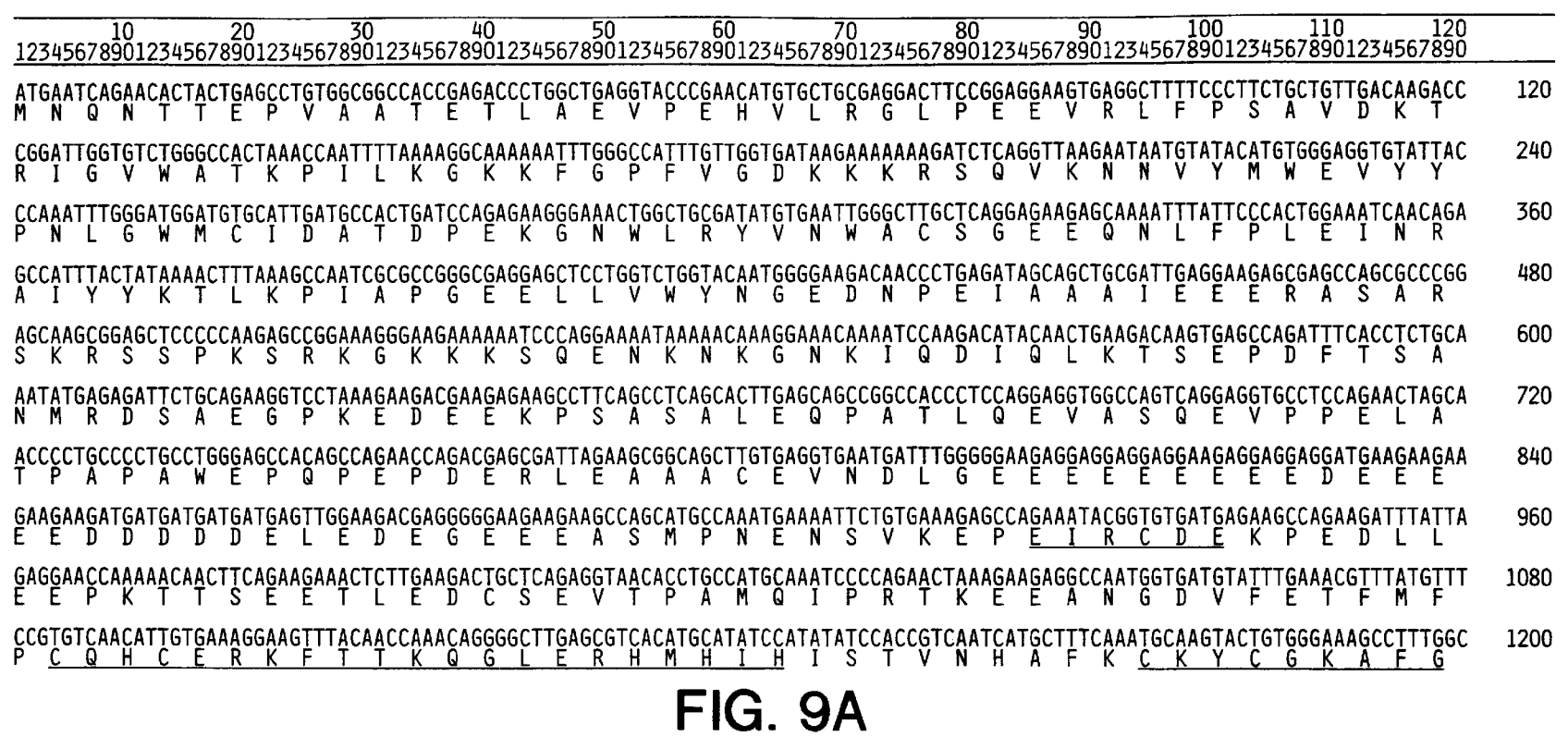
Figure 9C:
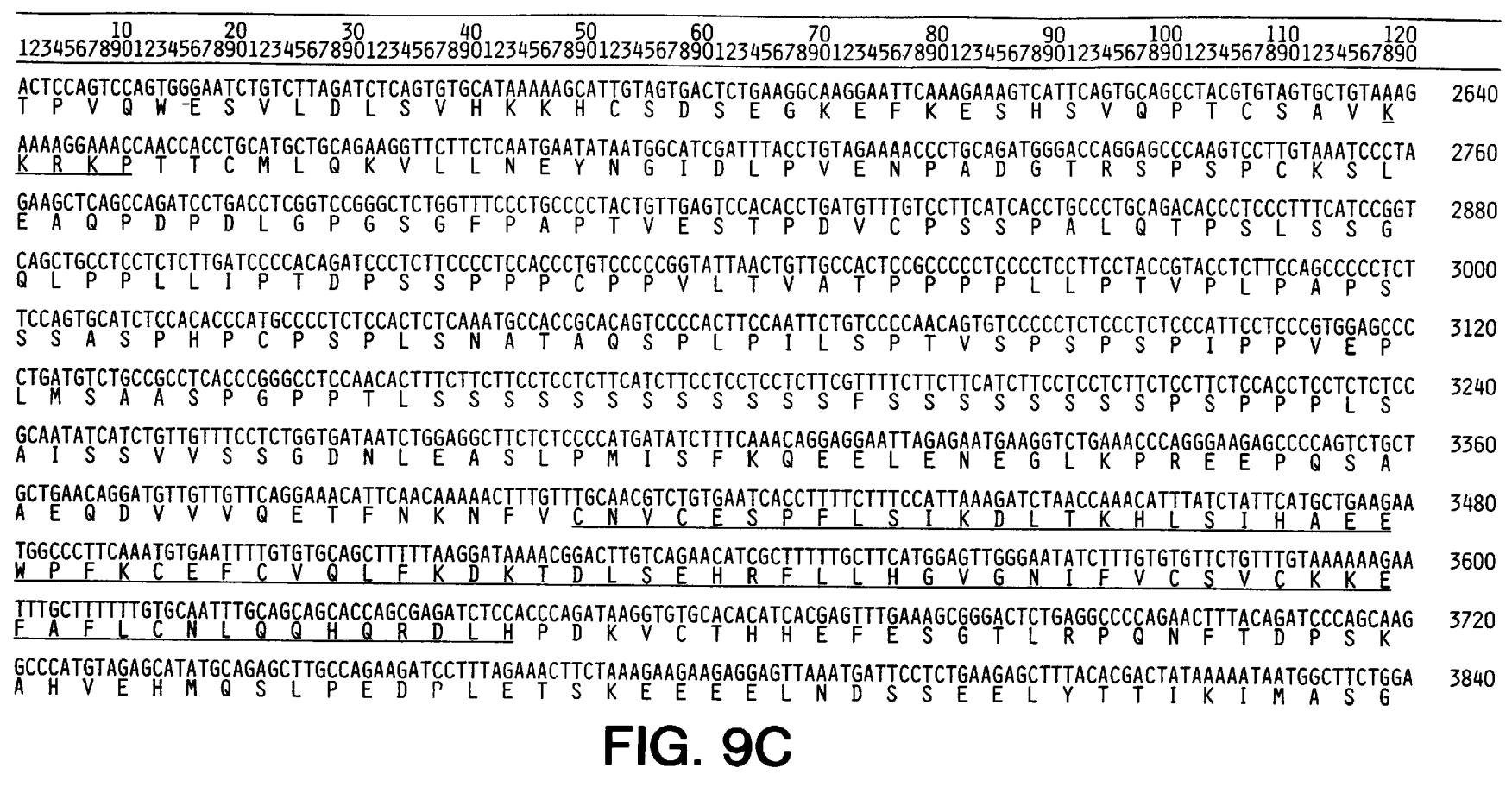

As used herein, the term "RIZ" means a protein having substantially the amino acid sequence of human RIZ as shown in FIG. 9 (SEQ ID NO: 4) or of rat RIZ as shown in FIG. 1 (SEQ ID NO: 2). The term "RIZ" is meant to include normal variants such as the allelic variants disclosed herein. Such normal variants can differ in amino acid sequence but share the same or similar functional activities such as binding to GTP, DNA or Rb (see Examples). A RIZ is referred to as a "normal RIZ" or a "wild-type RIZ", all of which are distinct from a mutant RIZ. In addition to the allelic variants, RIZ also can be a truncated RIZ protein encoded by a subset of the RIZ exons and that functions like a RIZ. Such a variant RIZ can be generated in the cell by alternative RNA splicing.

The term "RIZ" also includes peptide fragments of a RIZ, including active fragments of a RIZ. As used herein, the term "active fragment" means a peptide portion of a full length RIZ protein that has at least one activity that is characteristic of the corresponding full length protein. A peptide portion of a rat RIZ having the sequence EIRCEEKPEDL (SEQ ID NO: 6) or a peptide portion of a human RIZ having the sequence EIRCDEKPEDL (SEQ ID NO: 91) are examples of active fragments of a RIZ that can bind to Rb. Other RIZ activities that can be associated with an active fragment of a RIZ include the ability to bind DNA in a zinc ion-dependent manner, the ability to bind GTP or an anti-RIZ antibody, or the ability to act as a hapten or immunogen to obtain an anti-RIZ antibody.

The present invention provides an active fragment of a RIZ containing substantially the amino acid sequence of the RIZ cr2 motif, EIRCEEKPEDL (SEQ ID NO: 6), or EIRCDEKPEDL (SEQ ID NO: 91), where the cysteine residue is required when the activity of the fragment is Rb binding. The cr2 motifs of human RIZ or rat RIZ are examples of active fragments of a RIZ (see FIG. 10). Such active fragments can be produced by recombinant DNA methods, by peptide synthesis or by enzymatic cleavage of a RIZ protein. The present invention also provides a non-naturally occurring polypeptide having incorporated therein a RIZ cr2 core motif. Such a polypeptide can be produced using well known recombinant DNA methods.

A RIZ protein or a RIZ polypeptide containing the cr2 motif such as the amino acid sequences EIRCEEKPEDL (SEQ ID NO: 6) and EIRCDEKPEDL (SEQ ID NO: 91) can bind to Rb and, therefore, is useful for isolating Rb from a sample. Purified Rb can be used, for example, as a control target in a diagnostic test to detect whether a subject has a mutated Rb. Additionally, Rb can be used as a reagent to detect whether a sample has a RIZ which can bind to Rb or a mutant RIZ that fails to bind Rb. Mutations that affect the function of Rb and are diagnostic for cancer are well known in the art (see, for example, Lee et al., *In Tumor Suppressor Genes*, Chapter 11, Marcell Decker (1990).

To purify Rb, RIZ protein can be contacted with the Rb containing sample under suitable conditions, which allow formation of a RIZ-Rb complex. Suitable conditions for complex formation can be determined empirically and include, for example, an appropriate buffer concentration and pH and time and temperature of incubation that permit binding of the RIZ to Rb. The RIZ-Rb complex can be separated from unbound material in the sample and Rb can be dissociated from the complex and obtained in substantially purified form.

Substantially purified Rb can be obtained, for example, by using affinity chromatography, in which a RIZ is bound to a solid support, the sample is applied to the support to allow binding of Rb to the RIZ, the support is washed to remove unbound material and Rb is eluted from the support. Useful solid supports include, for example, agarose, Sepharose™ or plastic. RIZ can be attached to a solid support by direct chemical coupling or by an indirect means such as an affinity interaction with an anti-RIZ antibody bound to the support. Other indirect means for coupling a RIZ to a support include incorporating one entity of a known ligand/receptor pair into the RIZ, with the corresponding entity coupled directly to the support. For example, biotin can be coupled to RIZ and avidin can be coupled directly to a solid support to bind the RIZ to the support. Also, RIZ can be expressed as a fusion to glutationine S-transferase (see Example II) and the fusion protein can be bound to a glutathionine coupled support.

The present invention also provides a RIZ binding reagent. As used herein the phrase "RIZ binding reagent" means a chemical or biological molecule that specifically binds to a RIZ. As used herein with reference to a RIZ, the term "specifically binds" means that under a defined set of conditions, the RIZ binding reagent interacts with a RIZ but not with an unrelated molecule or with a mutant RIZ. Rb and anti-RIZ antibody are examples of a RIZ binding reagent.

The invention also provides a mutant RIZ binding reagent. As used herein, the phrase "mutant RIZ binding reagent" means a chemical or biological molecule that specifically binds to a mutant RIZ but not to a wild-type RIZ. In this case, the mutant RIZ binding reagent, under a defined set of conditions, interacts with the mutant RIZ but not with a wild-type RIZ.

Rb and an antibody specific for a RIZ are examples of reagents that can specifically bind to a RIZ. As used herein, the term "antibody" is used in its broadest sense to include polyclonal and monoclonal antibodies, as well as polypeptide fragments of antibodies that retain a specific binding activity for a specific antigen of at least about $1\times10^5 M^{-1}$. One skilled in the art would know that a fragment such as Fab, $F(ab')_2$, Fv and Fd fragments of an anti-RIZ antibody, for example, can retain specific binding activity for a RIZ and, thus, is included within the definition of an antibody. In addition, the term "antibody" as used herein includes naturally occurring antibodies as well as non-naturally occurring antibodies and fragments of antibodies that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

An antibody specific for a RIZ can be prepared using well known methods as described, for example, by Harlow and Lane, *Antibodies: A laboratory manual* (Cold Spring Harbor Laboratory Press, 1988), which is incorporated herein by reference. For example, RIZ protein or a portion of the RIZ protein can be used as an immunogen, which can be prepared from natural sources or produced recombinantly or, in the case of a portion of the RIZ protein, can be chemically synthesized. Non-immunogenic peptides of RIZ protein can be made immunogenic by coupling to a carrier molecule such as bovine serum albumin or keyhole limpet hemocyanin as described, for example, by Harlow and Lane, supra, 1988. In addition, a RIZ fusion protein can be expressed as described in Example II. Such a fusion protein can be readily purified and used as an immunogen (see Example II). These methods can be used to produce various anti-RIZ antibodies.

Polyclonal antibodies can be raised, for example, in rabbits or goats. In addition, monoclonal antibodies can be obtained using well known methods (see, for example, Reed et al., *Anal. Biochem.* 205:70–76 (1992)), which is incorporated herein by reference; see, also, Harlow and Lane, supra, 1988). For example, spleen cells from a RIZ immunized mouse can be fused to an appropriate myeloma cell line such as SP2/0 or P3x653.Ag8 myeloma cells to produce hybridoma cells. Cloned hybridoma cell lines can be screened using a labeled RIZ immunogen to identify clones that secrete monoclonal antibodies. Hybridomas that express antibodies having a desirable specificity and affinity can be isolated and utilized as a continuous source of antibodies. A dependable source of monoclonal antibodies is desirable, for example, for preparing diagnostic kits as described below.

An antibody specific for a mutant RIZ protein also can be prepared using the above methods by immunizing with either the full-length mutant RIZ protein or with a fragment of the protein containing the mutation. Methods to direct the immune response to the mutant sequence also are well known in the art and include, for example, use of particular adjuvants or pre-prior tolerization of the animal to the wild-type RIZ sequence. Such tolerization can be performed by immunizing the animal with the wild-type RIZ in conjunction with administration of anti-T cell antibodies or immunosuppressive drugs. A monoclonal antibody to the mutant sequence can be obtained by screening a population of hybridomas for those that express an antibody that binds the mutant RIZ sequence but not a wild-type RIZ sequence.

The invention also provides a substantially purified nucleic acid molecule, which encodes a RIZ such as a mammalian RIZ. For example, the invention provides substantially purified nucleic acid molecules having substantially the nucleotide sequences encoding human RIZ and rat RIZ as shown in FIG. 9 (SEQ ID NO: 3) and FIG. 1 (SEQ ID NO: 1), respectively.

As used herein, the term "substantially purified nucleic acid molecule" means a nucleic acid molecule that is in a form that is relatively free from contaminating lipids, proteins, nucleic acids or other cellular material normally associated with a nucleic acid molecule in a cell. A substantially purified nucleic acid molecule can be obtained, for example, by recombinant DNA methods as described herein (see, also, Sambrook et al., *Molecular Cloning: A laboratory manual* (Cold Spring Harbor Laboratory Press 1989), which is incorporated herein by reference) or can be chemically synthesized.

As used herein with reference to a RIZ, the term "substantially the nucleotide sequence" means, for example, the disclosed nucleotide sequence for human RIZ (SEQ ID NO: 3), as well as a similar sequence that contains, for example, different nucleotides than shown in SEQ ID NO: 3, but that, as a result of the degeneracy of the genetic code, encodes the same amino acid sequence as shown in SEQ ID NO: 4. In addition, the rat RIZ nucleotide sequence (SEQ ID NO: 1) is considered to be substantially similar to the nucleotide sequence encoding human RIZ (SEQ ID NO: 3). For convenience, the coding strand for a nucleic acid molecule encoding a RIZ is shown. It should be recognized, however, that the complementary strand also is encompassed within the disclosed nucleic acid molecules. Thus, unless otherwise indicated, reference herein to a nucleic acid molecule or to a nucleotide sequence is meant to include the complementary sequence.

A nucleic acid molecule of the invention can encode a variant RIZ such as the allelic RIZ variants disclosed herein as well as variants of a RIZ that contain only particular exons of the gene that can be produced in a cell by alternative RNA splicing. In addition, a nucleic acid molecule of the invention can encode a portion of a RIZ such as an active fragment of a RIZ containing the polypeptide EIRCEEKPEDL (SEQ ID NO: 6) and EIRCDEKPEDL (SEQ ID NO: 91), which bind to the Rb pocket.

The invention also provides a nucleotide sequence that specifically hybridizes to a portion of a nucleic acid molecule encoding a mammalian RIZ under relatively stringent hybridization conditions. As used herein with reference to a RIZ, the term "specifically hybridizes" means that under a defined set of hybridization conditions, the nucleotide sequence can interact with a RIZ encoding nucleic acid molecule but not with an unrelated nucleic acid molecule. A nucleotide sequence that specifically hybridizes to a RIZ can be complementary to a nucleotide sequence encoding a RIZ or can be a RIZ coding sequence or a portion thereof.

A nucleotide sequence that specifically hybridizes to a nucleic acid molecule encoding a RIZ or a mutant nucleic acid molecule encoding a RIZ should be at least ten nucleotides in length and can be prepared, for example, by restriction endonuclease digestion of a cloned nucleic acid molecule encoding a RIZ or by PCR amplification of a portion of the nucleic acid molecule shown in FIG. 1 (SEQ ID NO: 1) or FIG. 9 (SEQ ID NO: 3), or by chemical synthesis.

Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence. If desired, a hybridizing nucleotide sequence can be detectably labeled and used as a probe or can be used as a primer for PCR. Methods for detectably labeling a nucleotide sequence are well known in the art (see, for example, Sambrook et al., supra, 1989; see, also, Ausubel et al., *Current Protocols in Molecular Biology* vol. 2, chapter 10 (Greene Publ., NY 1989), which is incorporated herein by reference).

As used herein, the term "mutant nucleic acid encoding a RIZ" includes nucleic acid molecules having a mutation in an exon, thus encoding a mutant RIZ protein, as well as nucleic acid molecules having a mutation in a region of the RIZ gene other than the exons. A mutation in the RIZ gene occurring outside the exons can involve a regulatory element of the gene that modulates the expression of the RIZ in a cell. Such regulatory elements that can be mutated include, for example, the promoter, enhancer, ribosomal binding site or intron-exon splice junctions. The term "mutant RIZ" also includes peptides of a mutant RIZ, including active fragments of a mutant RIZ.

A mutation that occurs in a regulatory element of the RIZ gene can have a significant impact on the level of expression of a RIZ in a cell. In addition, a mutation in a RIZ exon that codes for a stop codon within the reading frame of the RIZ can produce a truncated RIZ that may be inactive, have an altered activity or be subject to rapid proteolysis in the cell. Similarly, a deletion involving a substantial portion of the gene encoding the RIZ can result in a loss of RIZ expression.

As used herein, the term "mutant RIZ" includes any RIZ having a mutation in a RIZ exon that results in the expression of a RIZ having a functional activity differing from that of a wild-type RIZ normally expressed by a cell. A change in a functional activity characteristic of a mutant RIZ can result from one or more amino acid additions, deletions or substitutions in the wild-type RIZ sequence. Such mutations can arise spontaneously or can be resident in the population and inherited from generation to generation as occurs, for example, with Rb. As disclosed herein, a mutant RIZ can have a change in the nucleotide at position 317 in human RIZ from a G to a C, which results in the expression of a Tyr residue instead of a Cys residue at a.a. position 106.

The present invention also provides a nucleotide sequence that specifically hybridizes to a mutant nucleic acid molecule encoding a RIZ under relatively stringent conditions but not to a wild-type RIZ. In this case, the hybridizing sequence should be complementary to a portion of the RIZ gene containing the mutation.

The expression of a particular RIZ allele can be reduced in a cancer cell due to a mutation in the RIZ gene. As disclosed herein, melanoma tumor cells fail to express mRNA encoding one of two RIZ gene alleles present in the cells (see Example VI). The unexpressed allele likely contains a mutation outside the RIZ coding sequence that affects RIZ expression. Detection of such mutations through the RIZ protein or the RIZ gene can be diagnostic of a pathology such as a cancer.

A mutant RIZ can be obtained, for example, by site directed mutagenesis of a nucleic acid molecule encoding a RIZ, then screening the mutagenized nucleic acid molecule to identify an encoded mutant RIZ. Mutations that affect a functional activity of a RIZ such as Rb binding, DNA binding or GTP binding can be detected by screening for mutants that have lost such activities. Expression in a cell of a mutant RIZ such as mutant human RIZ, which can bind Rb, for example, but lacks a RIZ activity, can alter the association of wild type RIZ with Rb and can affect a function of a cell such as the ability of the cell to proliferate.

The ability of a RIZ to be expressed in the nucleus together with its ability to bind DNA, Rb and GTP (see Example II and IV) and its homology with Blimp-1 (PRD1-BF1) differentiation factor indicates that RIZ can function as a transcriptional regulatory protein or cell differentiation factor. Thus, a function of a cell can be modulated by expressing a RIZ in a cell, where the expressed RIZ can bind to Rb and to DNA in the cell. As used herein, the term, "a function of a cell" means a cell activity, including, for example, proliferation and differentiation. As used herein, the term "modulate" means increase or decrease. As disclosed herein the function of a cell can be modulated due to an altered level of expression of a RIZ or expression of a mutant RIZ in a cell.

The present invention provides methods for modulating a function of a cell by expressing in the cell a DNA sequence encoding a RIZ or an active fragment of a RIZ that can bind to Rb. Such a DNA sequence can be expressed by introducing into a host cell an appropriate expression vector having gene regulatory elements operably linked with the RIZ encoding nucleotide sequence. The expression vector can provide constitutive expression of the polypeptide or, if desired, inducible expression. Expression vectors having the appropriate gene regulatory elements can be purchased from commercial sources or can be constructed using well known methods. For therapeutic purposes, cells can be transfected in tissue culture, then administered Lo a subject, or a viral vector can be used to introduce a RIZ encoding nucleic acid into a cell in a subject.

As disclosed herein, RIZ can regulate the growth of normal adult cardiac muscle cells and prevent proliferation of surviving cells following cardiac muscle cell death. RIZ can function to maintain cells in the $G_1$ phase of the cell cycle by interacting with Rb through the cr2 domain of RIZ. In addition, the functional differentiation state of a cell, which involves maintenance of a cell in the $G_1$ phase of the cell cycle can be affected through the action of other RIZ domains such as the GTP binding domain and the zinc finger domains.

The regeneration of cardiac muscle cells can be promoted in a subject with cardiac damage by directly decreasing the activity of a RIZ or by decreasing the activity of Rb that occurs subsequent to RIZ binding. The activity of a RIZ can be decreased in such cells by introducing into the cells an expression vector having an expression control sequence operatively linked to a nucleotide sequence encoding a mutant RIZ polypeptide or an active fragment that can bind to Rb but lacks the growth suppressing properties of RIZ. The sequences EIRCEEKPEDL (SEQ ID NO: 6) and EIRCDEKPEDL (SEQ ID NO: 91) are examples of such a peptide.

As used herein, the term "growth suppressing properties of RIZ" means the ability of RIZ to effect the differentiation and the maintenance of cells in $G_1$. In fact, the cell may be in an extended $G_1$ phase or an $G_0$ phase or may be blocked at the $G_0/G_1$ boundary. For convenience, any such cells are referred to as being maintained or suppressed in $G_1$. The growth suppressing or differentiating properties of a RIZ are mediated by regions of the molecule outside the cr2 domain or in conjunction with cr2 that is involved in binding to the Rb pocket.

Neurons, like myocardial cells, normally do not proliferate in the adult. RIZ is preferentially expressed in neural cells (see Example V), indicating a role for RIZ in mediating $G_1$ suppression and differentiation of these cells. The ability to induce proliferation in neural cells can be useful for healing after injury of neural tissue treating neurodegenerative diseases such as Parkinson's disease, Huntington's disease or Alzheimer's disease or paralysis or motor neuron disorders. Thus, the disclosed methods for decreasing the activity of a RIZ protein in a muscle cell similarly can provide a therapy for a neurodegenerative disease.

As disclosed herein, mutations in the nucleotide sequence encoding a RIZ can be involved in the development of cancer such as in melanoma. The frequency of RIZ heterozygosity in melanoma cells versus normal individuals indicates that inactivation of a single RIZ allele is not infrequently found in melanoma (see Example VI). In addition, two of six melanoma cell lines heterozygous for RIZ expressed mRNA for only a single RIZ allele. For such cells, the overall expression of RIZ protein was reduced to about half the level detectable in the other heterozygous RIZ expressing melanoma cell lines. These results indicate that tumor cells such as from a melanoma can be characterized by a reduced level of RIZ protein and, thus, a reduced level of RIZ function. This loss of heterozygosity at the RIZ locus and the reduced expression of the RIZ protein is consistent with other studies showing that loss of heterozygosity of distal chromosome 1p is a late event in melanoma tumor progression that confers a selective growth advantage to the tumor cells (Dracopoli et al., *Proc. Natl. Acad. Sci., USA* 86:4614–4618 (1989)).

The absence of any detectable mutations in the RIZ coding sequence in heterozygous RIZ melanoma cell lines that express only one RIZ allele and the absence of any gross defects in the region near to the RIZ gene indicates that the loss of RIZ expression is due to small mutation in a regulatory region of the gene.

The loss of heterozygosity at the RIZ locus in melanoma can be involved in the increased tumor cell growth associated with melanoma cells having mutations in distal chromosome 1 (Dracopoli et al., supra) and can be responsible for the increased risk of melanoma observed in survivors of heritable retinoblastoma, which occurs without homozygous inactivation of the Rb gene. Since the tumor suppressor function of Rb requires complexing of Rb with an Rb binding protein such as RIZ, a decreased level of Rb-RIZ complex in a tumor cell, resulting from a reduced expression of a RIZ allele, can result in a loss in Rb tumor suppressor activity in the cell.

Further support for the loss of RIZ function and the development of cancer can be provided by the disclosure that RIZ is a differentiation factor. As such, a mutant RIZ can affect the regulation of cell growth by binding to the Rb pocket, a site in the Rb molecule that is involved in regulating cell proliferation. Thus, the present invention provides methods for restoring normal cell growth to a cancer cell that has a mutated or missing RIZ allele by expressing a normal RIZ protein in the cell.

The disclosure that RIZ can modulate a function of a cell by binding to a second molecule such as Rb or a nucleic acid such as DNA or RNA provides a means to identify agents that can effectively alter the association of a RIZ with a second molecule in a cell and, as a result, modulate a function of a cell. Thus, the present invention provides a screening assay useful for identifying an effective agent, which can alter the association of a RIZ with a second molecule.

An effective agent that can decrease the association of a RIZ with a second molecule such as Rb or that can decrease the activity of a RIZ can be useful for releasing a cell from Rb-mediated $G_1$ arrest. Alternatively, an effective agent that increases the association of a RIZ with a second molecule such as Rb or DNA or increases the activity of a RIZ can be useful for reducing the unrestricted growth of a cancer cell by providing a stronger $G_1$ arrest signal in the cell.

A nucleotide sequence that can specifically bind to a RIZ can be detected by using methods well known in the art (see for example, El-Deiry et al., *Nat. Gen.* 1:45 (1992), which is incorporated herein by reference). Genomic DNA can be processed, for example, by sonication to produce uniform-sized fragments which can be screened for the ability to bind to a RIZ. Genomic DNA sequences that bind to a RIZ can be isolated using, for example, an anti-RIZ antibody and Protein A affinity chromatography. The isolated DNA sequences can be amplified by PCR, which can be facilitated by ligating the original genomic DNA fragments to "catch linkers" (El-Deiry et al., supra, 1992) suitable for annealing to PCR primers.

Random oligonucleotides consisting of at least about ten nucleotides and including "catch linkers" also can be screened to identify sequences that can bind a RIZ. For example, RIZ protein can be immobilized to a filter, then incubated with the oligonucleotides under conditions that allow the RIZ to bind relatively specifically to a RIZ binding sequence. Unbound oligonucleotides can be washed from the filter, then specifically bound sequences can be eluted and amplified by PCR. Following three or more cycles of binding, elution and amplification, a consensus RIZ binding sequence can be obtained. If desired, the consensus RIZ binding sequence can be used to screen a genomic DNA library to obtain genomic DNA sequences containing the RIZ binding sequence.

An agent can be a chemical or biological molecule such as a simple or complex organic molecule, a peptide, a peptido-mimetic, a protein, a carbohydrate or an oligonucleotide that has the potential for altering the association of a RIZ with a second molecule or altering an activity of a RIZ. With reference to a RIZ, the term "effective agent" means an agent that can, in fact, alter the association of RIZ with a second molecule or can alter the activity of a RIZ.

An effective agent can be, for example, a nucleic acid molecule that encodes a RIZ or a mutant RIZ or is complementary to a RIZ- or mutant RIZ-encoding nucleotide sequence. Such nucleic acid molecules can be contained within an expression vector having the RIZ encoding sequence operably linked to an expression control sequence. An effective agent also can be an antisense RIZ or a ribozyme complementary to a RIZ mRNA sequence. Such agents can reduce the level of expression of a RIZ in a cell and, as a consequence, can alter the amount of a RIZ that is associated with a second molecule in a cell.

As used herein with reference to a RIZ, the term "alter the association" means that the association of a RIZ and a second molecule either is increased or is decreased due to the presence of an effective agent. As a result of an altered association of RIZ with a second molecule in a cell, the activity of the RIZ or second molecule can be increased or decreased, which can modulate a function of a cell. As used herein with reference to a RIZ, the term "alter the activity" means that the effective agent can increase or decrease the activity of RIZ in a cell, such as by altering the association of a RIZ with the second molecule as described above by modifying, for example, an activity of a RIZ that occurs consequent to binding a second molecule.

An effective agent that alters the association of a RIZ with a second molecule can interfere with the ability of the RIZ and the second molecule to associate or can cause the dissociation of a bound RIZ-second molecule complex. In the presence of an effective agent, the association of a RIZ with a second molecule can be altered, which can alter the activity of the RIZ or the second molecule in the cell. As a result of the altered activity, a cell function such as the ability of a cell to proliferate can be modulated. Thus, the identification of an effective agent that alters the association of a RIZ with a second molecule provides a means to modulate cell proliferation.

An effective agent that alters the association of a RIZ and Rb can be useful as a medicament to treat a pathology characterized, in part, by excessive cell growth such as occurs in a cancer or by insufficient cell growth such as occurs in a tissue that fails to regenerate in response to cell death. A peptide having the sequence EIRCEEKPEDL (SEQ ID NO: 6) or EIRCDEKPEDL (SEQ ID NO: 91), which represent the cr2 motif of RIZ, is an example of an effective agent. Either of the peptides can alter the association between a RIZ and Rb (see Example II) and can induce cells such as adult cardiac muscle cells or adult neural cells to proliferate, which can regenerate heart function or neural function, respectively, following injury or disease.

The present invention also provides in vitro screening assays to detect an effective agent. Such screening assays are particularly useful in that they can be automated, which allows for high through-put screening, for example, of randomly or rationally designed agents such as drugs, peptido-mimetics or peptides in order to identify agents that effectively alter the association of a RIZ and a second molecule or modulate a function of a cell.

An in vitro screening assay can utilize, for example, RIZ or a RIZ fusion protein such as a glutathione-S-transferase-RIZ fusion protein (GST-RIZ; see Example II). For in vitro screening assays, the RIZ or RIZ fusion protein can be attached to a solid substrate, provided the attached RIZ maintains the ability to associate with a particular second molecule. For example, when human RIZ is used in the assay, the solid substrate can contain a covalently attached anti-RIZ antibody to bind RIZ to the substrate (see Example II). Alternatively, a GST-RIZ fusion protein can be used in the assay and the solid; substrate can contain covalently attached glutathione, which is bound by the GST component of the GST-RIZ fusion protein. Similarly, a second molecule or a GST-second molecule fusion protein can be used in an in vitro assay as described herein.

An in vitro screening assay can be performed by allowing, for example, a RIZ or RIZ-fusion protein to bind to the solid support, then adding a second molecule and an agent to be tested. Alternatively, a second molecule or a second molecule-fusion protein can be attached to the solid support and RIZ and an agent to be tested are added. Control reactions, which do not contain an agent, can be performed in parallel. Following incubation under suitable conditions, which include, for example, an appropriate buffer concentration and pH and time and temperature of incubation that permit binding of a RIZ and a second molecule, the amount of the RIZ and second molecule that have associated in the absence of an agent and in the presence of an agent can be determined.

The association of a RIZ and a second molecule can be detected, for example, by attaching a detectable moiety such as a radionuclide or a fluorescent label to the second molecule and measuring the amount of label that is associated with the solid support, wherein the amount of label detected indicates the amount of association of the second molecule and RIZ. By comparing the amount of specific binding in the presence of an agent as compared to the control level of binding, an effective agent, which alters the association of a RIZ and a second molecule, can be identified. Such an assay is particularly useful for screening a panel of agents such as a peptide library in order to detect an effective agent.

In an in vitro screening assay as disclosed herein, the order in which the components are added can be informative. For example, the agent to be detected can be combined with a RIZ prior to adding a second molecule, can be combined with a second molecule prior to adding a RIZ or can be added after allowing binding of the RIZ and the second molecule. Depending on the relative affinities of the components in the reaction mixture for each other, the order of addition and the time between mixing the first two components and adding the remaining component can be manipulated to detect effective agents with varying properties.

The methods for identifying an effective agent that alters the association of RIZ with a second molecule, can be performed to determine, for example, whether the agent can dissociate a bound RIZ-second molecule complex. For this purpose, a RIZ is first contacted with a second molecule under conditions suitable for forming a RIZ-second molecule complex and thereafter the complex is contacted with the effective agent.

The invention also provides methods for identifying an effective agent that alters the association of a RIZ and a second molecule in a test sample containing the RIZ and the second molecule. As used herein, the term "test sample" means a cell or tissue specimen that is obtained from a subject and is to be examined for expression of RIZ protein or a nucleic acid molecule encoding RIZ. A test sample can be obtained, for example, during surgery or by needle biopsy. The test sample can be, for example, a soluble lysate of a cell preparation obtained by treating the cells with a solubilizing agent such as a non-ionic detergent.

A soluble lysate or other form of test sample can be examined by a gel-shift assay to determine the proportion of a RIZ and a second molecule that are associated as a complex. In this assay, the test sample is electrophoresed in a non-denaturing gel such as a low percentage polyacrylamide gel with a buffer containing 50 mM Tris (pH 8.5), 0.4M glycine, 2 mM EDTA and 3% glycerol. By adjusting the buffer conditions, gel concentration or other parameters of electrophoresis well known in the art, electrophoretic separation of a free second molecule, a free RIZ and a second molecule-RIZ complex in the test sample can be achieved. After electrophoresis, the identity of proteins in the gel can be determined by immunoblotting using antibodies specific for the second molecule or the RIZ. Methods for performing immunoblotting using an enzyme or radioisotope labeled primary or secondary antibody are well known in the art (see, for example, Harlow and lane, supra 1988).

If desired a separate gel can be produced western blotted with either anti-second molecule antibodies or anti-RIZ antibodies. Each gel can contain known amounts of both the second molecule and the RIZ to be detected to provide standards for quantitation and specificity of the blot. The amount of a second molecule-RIZ complex in a test sample treated with an agent suspected of being able to alter the association of the second molecule with RIZ can be compared to a control test sample not treated with the agent in order to identify an effective agent, which increases or decreases the proportion of the second molecule-RIZ complex in the treated relative to the control test sample.

The present invention provides methods to modulate a function of a cell by contacting the cell with an effective agent. As used herein, the term "contacting" means providing within sufficient proximity such that the effective agent can interact with a target. Thus, an effective agent can be contacted with Rb in vitro, or can be contacted with a cell, provided the effective agent can enter the cell to interact with RIZ or a second molecule. For example, a small molecule effective agent can enter a cell passively such as through pores in the cell membrane or through the lipid bilayer of the cell. An effective agent also can enter a cell by active means such as through pinocytosis, endocytosis, phagocytosis or through an energy driven specific transport mechanism.

Methods for introducing and expressing a RIZ in a cell can be performed using well known expression vectors and gene transfer methods (for example, see Sambrook et al., supra, 1989 and Kriegler M. *Gene Transfer and Expression: A Laboratory Manual* (W. H. Freeman and Co. New York N.Y., 1990), which is incorporated herein by reference). Such gene transfer methods include, for example, transfection methods such as calcium phosphate precipitation, electroporation or lipofection, or viral infection. For convenience, the term "transfected cell" is meant to include any cell having an exogenous nucleic acid molecule introduced therein. Transfected cells useful for expressing large amounts of RIZ protein can be prokaryotic or eukaryotic and include, for example bacterial cells such as *E. coli*, yeast cells, insect cells or mammalian cells such as COS cells or chinese hamster ovary (CHO) cells.

An expression vector useful for expressing a RIZ or a mutant RIZ in a cell contains an expression control sequence operatively linked to a nucleotide sequence encoding a RIZ. An expression control sequence that is operatively linked to a nucleic acid sequence can direct the transcription and translation of the nucleic acid sequence in vitro or in an appropriate host cell. Expression control elements are well known in the art and include, for example, promoters, enhancers and appropriate start and stop codons. In particular, a tissue specific expression control element can provide a means to selectively express a RIZ or mutant RIZ in a cell. Tissue specific control elements are well known in the art and include, for example, the muscle creatine kinase enhancer for restricting expression to muscle cells and the Purkinje cell protein-2 promoter for restricting expression to Purkinje cells (Vandaele et al., *Genes Devel.* 5:1136–1148 (1991), which is incorporated herein by reference).

Viral vectors that are compatible with a targeted cell are particularly useful for introducing a nucleic acid molecule encoding a RIZ or a mutant RIZ into a cell. For example, recombinant adenoviruses having general or tissue-specific promoters can be used to deliver a nucleic acid encoding RIZ into a variety of cell types in various tissues and can direct expression of the nucleic acid in the target cell (Lebkowski et al. U.S. Pat. No. 5,354,678, issued Oct. 11, 1994, which is incorporated herein by reference). Recombinant adeno-associated viruses also are useful for introducing a nucleic acid molecule encoding RIZ into a cell and have the added advantage that the recombinant virus can stably integrate into the chromatin of even quiescent non-proliferating cells such as neurons of the central and peripheral nervous systems (Lebkowski et al., *Mol. Cell. Biol.* 8:3988–3996 (1988), which is incorporated herein by reference).

Such viral vectors are particularly useful where it is desirable to introduce a nucleic acid molecule encoding a RIZ or a mutant RIZ into a cell in a subject, for example, for gene therapy. Viruses are specialized infectious agents that can elude host defense mechanisms and can infect and propagate in specific cell types. The specificity of viral vectors for particular cell types can be utilized to target predetermined cell types. Thus, the selection of a viral vector will depend, in part, on the cell type to be targeted. For example, if a neurodegenerative disease is to be treated by increasing the level of RIZ in neuronal cells affected by the disease, then a viral vector that targets neuronal cells can be used. A vector derived from a herpes simplex virus is an example of a viral vector that targets neuronal cells (Battleman et al., *J. Neurosci.* 13:941–951 (1993), which is incorporated herein by reference).

A viral vector that is specific for a particular blood cell or its precursor cell can be used to introduce a nucleic acid molecule encoding a RIZ or a mutant RIZ into a hematopoietic cell from a subject having a pathological condition of the hematopoietic system. A vector based on a human immunodeficiency virus is an example of such a viral vector (Carroll et al., *J. Cell. Biochem.* 17E:241 (1993), which is incorporated herein by reference). In addition, a viral vector or other vector can be constructed to express a nucleic acid encoding a RIZ in a tissue specific manner by incorporating a tissue-specific promoter or enhancer into the vector (Dai et al., *Proc. Natl. Acad. Sci. USA* 89:10892–10895 (1992), which is incorporated herein by reference).

Retroviral vectors can be particularly useful for introducing a nucleic acid molecule encoding a RIZ or a mutant RIZ into a cell in vivo. Retroviral vectors can be constructed either to function as infectious particles or as non-infectious particles that undergo only a single initial round of infection. In the former case, the genome of the virus is modified so that it maintains the necessary genes, regulatory sequences and packaging signals to synthesize new viral proteins and RNA. However, genes conferring oncogenic potential of these viruses are destroyed or removed. After the viral proteins are synthesized, the host cell packages the RNA into new viral particles, which can undergo further rounds of infection. The viral genome also is engineered to encode and express the desired recombinant gene.

In the case of non-infectious viral vectors, a helper virus genome is required to provide the structural genes necessary to encode for the viral structural proteins. However, the helper virus is mutated to destroy the viral packaging signal required to encapsulate the helper viral RNA into viral particles. Thus, only the recombinant viral vector containing the gene of interest and a functional packaging signal, but lacking viral structural genes can be incorporated into a virus particle. Although this new virus can infect a target cell, no further infectious virus can be produced since there are not viral structural genes provided. Methods for constructing and using viral vectors are known in the art and reviewed, for example, in Miller and Rosman, *Biotechniques* 7:980–990 (1992), which is incorporated herein by reference. The specific type of vector will depend upon the intended application. These vectors are well known and readily available within the art or can be constructed by one skilled in the art.

For gene therapy, a vector containing a nucleic acid encoding a RIZ or a mutant RIZ can be administered to a subject by various methods. For example, if viral vectors are used, administration can take advantage of the target specificity of the vectors. In such cases, there is no need to administer the vector locally at the diseased site. However, local administration can be a particularly effective method of administering a nucleic acid molecule. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule encoding a RIZ or a mutant RIZ into a cell in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., *Science* 259:1745–1748 (1993), which is incorporated herein by reference). In addition, a nucleic acid molecule encoding a RIZ can be transferred into a variety of tissues using the particle bombardment method (Williams et al., *Proc. Natl. Acad. Sci. USA* 88:2726–2730 (1991), which is incorporated herein by reference). Such nucleic acid molecules can be linked to the appropriate nucleotide sequences required for transcription and translation.

A particularly useful mode of administration of a nucleic acid encoding a RIZ or mutant RIZ is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promotor, an enhancer or other expression element specific for the desired subset of cells to be targeted can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

An alternative method of modulating a function of a cell is to introduce a nucleic acid molecule having a nucleotide sequence encoding an antisense RIZ or a ribozyme specific for a RIZ mRNA into the cell. Such a nucleotide sequence is included within the meaning of an effective agent since it can alter the expression level of RIZ and thus alter the association of a RIZ with a second molecule.

An antisense RIZ or a ribozyme specific for a RIZ mRNA can be complementary to the nucleotide sequence of a RIZ such as the nucleotide sequence of FIG. 1 (SEQ ID NO: 1) or FIG. 9 (SEQ ID NO: 3). An antisense RIZ or ribozyme specific for RIZ mRNA can be introduced into a cell using the methods and vectors described above. Chemically synthesized nucleotide sequences also can be administered directly to cells. Synthetic antisense or ribozyme oligonucleotides can be prepared using well known methods or can be purchased from commercial sources and, if desired, can incorporate nucleotide analogs to increase the resistance of the oligonucleotide to degradation by nucleases in a cell. Synthetic antisense or ribozyme sequences can be active in a cell after contact with and uptake by the cell.

An effective agent can be administered in vivo as a pharmaceutical composition containing the effective agent and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of an effective agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. One skilled in the art would know that a pharmaceutical composition containing an effective agent can be administered to a subject by various routes including, for example, by direct instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to modulate a function of a cell, an effective agent is administered in an effective amount, which can be determined using methods well known to those in the art. As used herein, the term "effective amount" means the amount that produces a desired effect. Thus, an effective amount of an effective agent can alter the association of a RIZ and Rb in a cell and can have a functional effect on the ability of a target cell to increase or decrease its ability to enter the cell cycle. Administration of an effective amount of an effective agent in vivo can reduce symptoms associated with a disease being treated.

The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of an effective agent needed to obtain an effective amount in a subject depends on many factors including the age and general health of the subject as well as the route of administration and the number of treatments to be administered, as well as the chemical form of the effective agent. In view of these factors, the skilled artisan would adjust the particular dose so as to obtain an effective amount for subject being treated.

The present invention also provides methods for detecting the presence of a RIZ in a test sample by detecting the RIZ protein or a nucleic acid molecule encoding RIZ. In addition, methods are disclosed for diagnosing a pathology that is characterized, in part, by an increased or decreased ability of a cell to enter the cell cycle by determining whether cell proliferation or lack thereof is due, for example, to increased or decreased expression of a RIZ or a mutant RIZ in the cell. The identification of such a pathology can allow for intervention therapy using an effective agent as described above.

A test sample can be obtained from a subject having a pathology characterized by increased or decreased cell function and can be compared to a control sample from a normal healthy subject to determine whether the cells in the vest sample have an increased or decreased level of a RIZ or a mutant RIZ. The level of RIZ protein in a cell can be determined by contacting a sample with a RIZ binding reagent such as an anti-RIZ antibody or Rb. For example, the level of RIZ in a cell can be determined by well known immunoassay or immunohistochemical methods using an anti-RIZ antibody (see, for example, Reed et al., supra, 1992; see, also, Harlow and Lane, supra, 1988). In addition, the expression of a mutant RIZ can be detected, for example, by an antibody that specifically binds to the mutant RIZ but not to wild-type RIZ.

The detection of a RIZ by binding to an antibody and to Rb can provide complementary information. For example, the antibody can be used to determine the total level of RIZ expressed, while Rb binding can be used to determine the fraction of RIZ that is bound to Rb. Because Rb can bind to other proteins in a cell, it is advantageous to first isolate RIZ from a cell prior to detecting the fraction of RIZ that is bound to Rb.

An increased or decreased level of expression of a RIZ in a cell in a test sample can be determined by comparison to an expected normal level for the RIZ in a particular cell type. A normal range of RIZ levels in various cell types can be determined by sampling a statistically significant number of normal cell types, which can be obtained from healthy subjects. In addition, a control sample can be evaluated in parallel with a test sample in order to determine whether a pathology characterized by increased or decreased cell function is due to increased or decreased expression of a RIZ or to expression of a mutant RIZ. The test sample can be examined using, for example, immunohistochemical methods as described above or the sample can be further processed and examined. For example, an extract of a test sample can be prepared and examined to determine whether RIZ that is expressed in cells in the sample can associate with Rb in the same manner as RIZ from control cells or whether a variant RIZ, which does not properly associate with Rb, is expressed in the cells in the test sample.

A diagnostic assay kit incorporating a reagent such as an anti-RIZ antibody or Rb can be useful for detecting a pathology due to altered RIZ expression or to expression of a mutant RIZ in a cell. Such a kit is particularly useful because it allows for standardization of assay conditions. A kit can contain, in addition to a reagent, a reaction cocktail that provides suitable reaction conditions for performing the assay and, if desired, a control sample that contains a known amount of RIZ. In addition, the kit can contain an antibody that is specific for the reagent. Where Rb is used as a reagent to detect RIZ, the kit also can contain a competitor molecule such as EIRCEEKPEDL (SEQ ID NO: 6) or EIRCDEKPEDL (SEQ ID NO: 91), which inhibits the association of RIZ and Rb and, therefore, can confirm the specificity of the binding reaction.

A diagnostic assay should include a simple method for detecting the amount of RIZ in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a test sample and, if desired, a control sample, with a labeled reagent, specifically bound reagent can be identified by detecting the particular moiety.

A labeled antibody that can specifically bind the reagent also can be used to identify specific binding of an unlabeled reagent. For example, if the reagent is an anti-RIZ antibody, a second antibody can be used to detect specific binding of the anti-RIZ antibody. A second antibody generally will be specific for the particular class of the first antibody. For example, if an anti-RIZ antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample.

A method for diagnosing a pathology characterized by an abnormal level of expression of a RIZ or can involve measuring the level of expression of a DNA or RNA in the sample. Similarly, diagnosing a pathology characterized by expression of a mutant RIZ or by the presence of a mutant nucleic acid molecule encoding a RIZ can involve detecting the mutation in the RIZ gene or in the RNA encoded by the gene.

For example, a nucleic acid molecule encoding a RIZ can be detected in a test sample using a complementary nucleotide sequence. If desired, the target nucleic acid molecule can be extracted from a test sample by methods well known in the art (See Sambrook et al., supra, 1988). Methods to detect the presence of a particular nucleic acid molecule within a population of nucleic acid molecules are well known to those in the art and include, for example, Southern blotting, northern blotting, slot blotting and PCR amplification (see, for example, Sambrook et al., supra, 1989). In situ hybridization also can be used to identify nucleic acids in directly in a sample containing cells or free chromosomes (see for example, Pardue, in *Nucleic Acid Hybridisation*: a practical approach (IRL Press, 1991), which is incorporated herein by reference).

To detect a nucleic acid molecule encoding a RIZ in a sample, the sample is contacted with the complementary nucleotide sequence, which can hybridize to a nucleic acid molecule encoding the RIZ under relatively stringent conditions. The nucleotide sequence can carry a detectable label such as a radioisotope. The presence of a nucleic acid molecule encoding the RIZ in the sample can be determined, for example, by detecting the level of the specifically bound nucleotide sequence. The normal level of binding of the nucleotide sequence also can be determined in a control sample. An increase or a decrease in the level of nucleic acid molecules encoding a RIZ in the test sample compared to the control sample indicates a pathology characterized by an abnormal expression of the RIZ. A complementary nucleotide sequence for a RIZ can also be used as a primer in a PCR reaction to amplify the RIZ for hybridization by a probe.

A mutant RIZ can be detected by hybridizing with a complementary nucleic acid molecule under relatively stringent conditions essentially as described above except that the complementary sequence is of sufficiently small size to enable selective hybridization to the mutant sequence but not to the wild-type sequence under the conditions chosen for hybridization. Alternatively, the RIZ gene or RNA can be purified directly from a test sample and, if desired, amplified from the sample by PCR and the mutant sequence determined by standard nucleotide sequencing methods (see, for example, Sambrook et al. supra, 1989). The mutant nucleic acid encoding a RIZ or the nucleic acid encoding a mutant RIZ also can be detected in a sample of cells or free chromosomes by in situ hybridization techniques (see, for example Pardue, supra, 1991).

The following Examples are intended to illustrate but not limit the invention.

EXAMPLE I

Cloning of Mammalian RIZ cDNAs

This section describes methods to clone a nucleic acid molecule encoding a RIZ from mammalian cDNA and genomic libraries.

The rat RIZ cDNA was obtained from a rat neonatal cardiac myocyte λgt11 cDNA expression library (Zhu et al., *Mol. Cell Biol.*, 13:4432 (1993), which is incorporated herein by reference). The library was screened using a 56 kD fragment containing the pocket binding site of Rb and the EE epitope (p56EERb) according to previously described methods (Macgregor et al., *Oncogene*, 5:451–458 (1991), which is incorporated herein by reference).

After induction of p56EERb was generated by cloning a synthetic pair of complementary polynucleotides that hybridize to form a double stranded linker encoding the EE-epitope, EEEEYMPME (SEQ ID NO: 8; Grussenmeyer et al., *Proc. Natl. Acad. Sci., USA.*, 82:7952–7954 (1985) and Walter, *J. Immune Meth.*, 88:149–161 (1986), both of which are incorporated herein by reference) and having Bsm I cohesive ends. The ends of the linker were phosphorylated by T4 kinase and the linker was ligated into the plasmid pET8Rbc (Huang et al., *Nature*, 350:160–162 (1991), which is incorporated herein by reference) to produce the plasmid p56EERb. The synthetic nucleotides used to make the linker were: 5'-AATCGATGAA GAAGAAGAAT ATATGCCTAT GGAACA-3' (SEQ ID NO: 9), and 5'-TTCCATAGGC ATATATTCTT CTTCTTCATC GATTTG-3' (SEQ ID NO: 10). A clone with four tandem copies of the EE linker was selected and used to direct expression of p56EERb in the *E. coli* strain BL21(DE3)pLysS as previously described (Huang et al. supra, 1991).

After induction of 56EERb, the bacterial cells were lysed as described (Huang et al. supra, 1991) and 56EERb was precipitated by ammonium sulfate (60% of saturation). The precipitate was dialyzed in dialysis buffer (20 mM Tris-HCl, pH 7.5, 50 mM NaCl, 1 mM EDTA, 1 mM DTT, 1 mM PMSF) and subjected to further purification by diethylaminoethyl (DEAE) Sepharose™ chromatography (Pharmacia, Piscataway N.J.). Partially purified p56EERb was eluted from DEAE by a salt gradient of 50 mM to 500 mM NaCl. Both the DEAE partially purified fraction and the dialyzed ammonium sulfate precipitate of 56EERb were used for screening the cDNA library.

For binding-specificity control, p56EERb was preincubated with 5 µM poly-L-lysine (Sigma) or 50 µM T- or K-peptide (Huang et al., supra, 1991) before applying onto filters. T peptide is an 18 residue synthetic peptide derived from residues 101-118 of SV40 large T antigen, while K peptide is the same as T peptide except for a lysine residue substituted for a glutamic acid residue at position 107 of SV40 large T antigen (Huang et al., supra, 1991). The T peptide binds to the Rb pocket while the K peptide does not.

The binding of p56EERb to a clone expressing a RIZ protein was detected using an anti-EE monoclonal antibody obtained as spent culture medium of the anti-EE hybridoma (Walter, supra, 1986) and an alkaline phosphatase conjugated goat anti-mouse IgG antibody specific for mouse immunoglobulin (Promega, Madision Wis.).

Filters containing 1×10$^6$ library phage plaques were screened using p56EERb and ten positive clones that survived three rounds of plaque purification were selected. Five clones, which maintained their reactivity with p56EERb in to presence of a non-specific inhibitory substance, poly-L-Lysine, but were inhibited from binding p56EERb in the presence of T peptide but not K peptide, were selected for further study. Inhibition by T peptide indicated that the selected clones expressed a product that binds the Rb pocket.

Of the final five clones, four contained an identical 1.9 kilobase (kb) insert. One of the clones, clone 7.1, was subjected to nucleotide sequencing. Sequencing was performed on both strands of the DNA and utilized the Sequenase enzyme™ (United States Biochemical Corp., Arlington Hts. Ill.). Clone 7.1 contained a partial cDNA sequence having a predicted open reading frame encoding 638 amino acids, which formed two types of readily recognizable motifs: a cr2 core motif and 3 zinc finger motifs (see below). The protein encoded by clone 7.1 was designated RIZ for "Rb-interacting zinc finger" protein.

The 1.9 kb insert was used to further screen the cardiac myocyte library and to screen a rat brain B49 cell cDNA library produced in the λZAP vector (Stratagene) according to standard methods (see Sambrook et al., supra, 1989) or purchased from a commercial source. Several clones containing overlapping open reading frames were obtained. The overlapping sequences were assembled into a contiguous stretch of 6171 nucleotides to obtain the cDNA sequence for rat RIZ (FIG. 1; SEQ ID NO: 1).

Analysis of the complete rat RIZ cDNA sequence revealed a large open reading frame beginning at nucleotide 157 and ending at nucleotide 5274. The initiation codon at nucleotide 157 was considered the translational start site based on its being the first ATG following an in-frame upstream stop codon at nucleotide 100 and by it's match with the Kozak consensus sequence (Kozak, Nucl. Acids Res. 15:8425–8148 (1987)). The identity of the start site was confirmed by analyzing an independent cDNA clone that revealed a divergent sequence upstream of nucleotide 92 but otherwise was identical to the assembled cDNA sequence of rat RIZ.

The complete rat RIZ cDNA sequence predicted a protein consisting of 1706 amino acids having a molecular weight of 187,437 Daltons (FIG. 1). Northern blot analysis showed a 7.2 kb major rat RIZ mRNA species. Southern blot analysis indicated that the rat RIZ genome contains a single copy of the RIZ gene.

A nucleic acid molecule encoding human RIZ was cloned from a human fetal brain cDNA library (Clonetech, Palo Alto, Calif.) and a human placental genomic cosmid DNA library (Stratagene, San Diego, Calif.) using the rat RIZ cDNA coding regions as a hybridization probe (clone 7.1). The human RIZ cDNA encodes a polypeptide of 1719 amino acids residues (see FIG. 9; SEQ ID NO: 4). The human RIZ gene obtained from the genomic library showed that RIZ coding sequence was divided between eight separate exons.

An allelic variant of the human RIZ gene is also identified. This variant contains a single nucleotide change of $T_{849}$ to $AS_{849}$, leading to a change of amino acid residue $D_{283}$ to $E_{283}$. The $T_{849}$ allele is estimated to be two times more frequent than the $A_{849}$ allele.

Both the rat and human RIZ proteins have similar sequence motifs including cr1, cr2, ce1 zinc finger, SH3, SH2 and a nuclear localization signal. The deduced rat and human RIZ amino acid sequences show 83% identity. In addition, a rabbit antiserum prepared to rat RIZ crossreacts with human RIZ.

EXAMPLE II

Detection and Characterization of RIZ-Rb Binding

This section describes methods for demonstrating binding of RIZ and Rb and for identifying an agent that effectively alters the binding of a RIZ and Rb.

To characterize the interaction between RIZ and Rb, a $^{35}$S-labeled fragment of rat RIZ from amino acid position 245-883 (RIZ (245-883)) was produced by subcloning the 1.9 kb insert of clone 7.1 into pBKS+ (Stratagene) to yield plasmid pBKS+7.1. Following subcloning, the RIZ insert was then removed and inserted downstream of the 5' untranslated sequence of β-globin in the vector pSP64-xβm (Krieg and Melton, Nucl. Acids Res., 12:7057–7070 (1984). SP6 RNA transcripts encoding RIZ (245-883) were produced by linearizing the plasmid encoding this fragment with Sal I and translating the RIZ fragment using a rabbit reticulocyte lysate in vitro protein translation system (Promega) containing $^{35}$S-methionine. The labeled RIZ fragment had an apparent molecular weight of 125 kD by sodium dodecyl sulfate polyacrylamide gel electrophoresis (SDS-PAGE), which was about 55 kD greater than the predicted molecular mass for this fragment of RIZ. The larger size obtained by SDS-PAGE is likely due to anomalous mobility of the RIZ fragment on the gel.

A 56 kD fragment of Rb produced by bacterial expression from p55Rb plasmid, as described previously (Huang et al., supra, 1991), was tested for binding to radiolabeled RIZ (245-883). Binding was detected by immunoprecipitation with an anti-Rb antiserum and Protein A-Sepharose™ (Huang et al., supra, 1990), which is incorporated herein by reference; and Huang et al., supra, 1991) followed by SDS-PAGE and autoradiography (see Harlow and Lane, supra, 1988). The rabbit anti-Rb antiserum was produced to purified p56Rb using previously described methods (see Harlow and Lane, supra, 1988).

The amount of binding of RIZ by Rb in the immunoprecipitation reaction was dependent on the concentration of Rb added. Full binding of $^{35}$S-labeled RIZ (245-883) was achieved by 10 nM Rb but not 3.3 nM Rb (not shown). These results indicated that RIZ binds Rb.

A competition experiment was used to compare the relative binding affinity of RIZ for Rb as compared to another Rb binding protein, SV40 large T antigen. The full length large T antigen cDNA was subcloned from Y-62-25-2 into plasmid pSP64 for in vitro transcription/translation and $^{35}$S-methionine labeling as described above. When approximately equal amounts of T antigen and RIZ were mixed individually or together with the same amount of Rb, similar amounts of T antigen and RIZ, or somewhat more RIZ, were co-precipitated (not shown). These data indicate that RIZ has a similar binding affinity for Rb as does large T antigen.

Several mutations were generated to identify the regions of RIZ that were involved in binding to Rb. A single amino acid substitution was introduced into full length RIZ cDNA in the plasmid pCMVRIZ to change cysteine at a.a. position 307 to glycine. pCMVRIZ was produced by subcloning the full-length RIZ cDNA into the pRc-CMV vector (Invitrogen, San Diego, Calif.). Mutagenesis of the cr2 motif changing Cys to Gly was performed using the T7 GENE™ mutagenesis kit (United States Biochemical, Arlington Heights, Ill.) as follows: Briefly, the primer, 5'-CCGGAGATCC GGGCTGAAGA AAAGCCA-3' (SEQ ID NO: 11), was used to direct DNA synthesis on a single stranded antisense template prepared from pBSK-5.4. Vector pBSK-5.4 was produced by cloning the cDNA RIZ amino terminal clone 5.4 obtained from the B49 λZAP DNA library into vector pBSK+. An Nsi I to Spe I fragment (nucleotide 1-1718) containing the point mutation was sequenced and subcloned into pRc-CMV to produce pCMVmRIZ (RIZ$^{307}$-Gly). A $^{35}$S labeled fragment of RIZ from amino acid position 1-575 (RIZ (1-575)) and $^{35}$S-RIZ (1-575)$^{307\text{-}Gly}$ were produced by in vitro transcription/translation of Spe I linearized template as described above.

Binding between labeled RIZ (1-575) and the glycine mutant with 33 nM Rb was evaluated by immunoprecipitation with anti-Rb antiserum followed by SDS-PAGE and autoradiography. The results showed that the 56 kD Rb bound the $^{35}$S-RIZ (1-575) fragment but not to the $^{35}$S-RIZ (1-$_{575}$)$^{307\text{-}Gly}$ cr2 mutant (not shown). These results indicate that the RIZ cr2 motif is involved in Rb binding.

To determine whether the RIZ cr2 motif is functional and sufficient for binding Rb, the 11 amino acid peptide EIRCEEKPEDL (SEQ ID NO: 6), representing the cr2 motif of RIZ (RIZ-Pep), and a cysteine to glycine mutant of this peptide (RIZ-Pep*) were synthesized according to standard procedures and tested at various concentrations for their ability to inhibit the binding of labeled RIZ (1-575) to 56 kD Rb. Binding was inhibited with wild-type peptide but not the C→G mutant peptide (see FIG. 4). These data indicate the cr2 motif of RIZ is sufficient for binding to Rb and that the cysteine at a.a. position 307 in the cr2 motif of RIZ is involved in the binding.

Figure 4:
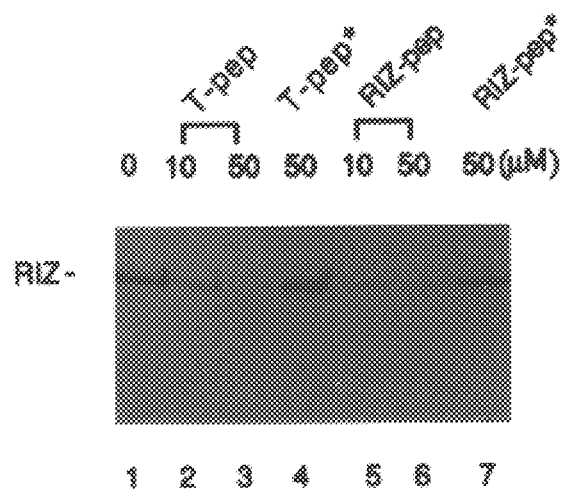
FIG. 4 demonstrates that $^{35}$S-labeled RIZ (a.a. position 1-575) specifically binds to Rb in vitro. Binding assays were performed in the absence or presence of peptides derived from RIZ or SV40 large T antigen. T-pep: peptide of large T antigen (a.a. position 101-118); T-pep*: single amino acid residue mutant of T-pep ($_{107}^{Glu}$); RIZ-pep: peptide of RIZ (a.a. position 304-314); RIZ-pep*: single amino acid mutant of RIZ pep (307$^{Gly}$).

In a similar manner, the binding between radiolabeled RIZ (1-575) and 56 kD Rb was tested for inhibition using the 17 amino acid Rb binding peptide (101-118: T-pep) from the SV40 large T antigen oncoprotein and a position 107 -Glu to Lys mutant of T-pep (T-pep*) that lacks Rb binding activity (Huang et al., supra, 1990 and Huang et al., supra, 1991). Binding was inhibited with T-pep but not with the mutant (FIG. 4). These results indicate that RIZ and large T antigen bind to a similar region on Rb.

The 56 kD Rb fragment that binds to RIZ is a C-terminal fragment containing the Rb pocket binding region and a C-terminal extension. To further define the portion of 56 kD Rb that binds to RIZ, several Rb mutant polypeptides were tested for binding to RIZ. Mutant and full length Rb were cloned and in vitro transcribed/translated as described previously (Huang et al., supra, 1990). H209 is a point mutation resulting in a single amino acid change in Rb that was identified in the small cell lung cancer H209 cell line (American Type Culture Collection (ATCC) #HTB 172). The various Rb forms were tested for binding to glutathionine S-transferase (GST) fused to a fragment of RIZ from amino acid position 245-573 (GST-RIZ (245-573)). This RIZ fragment contains all of the E1A motifs related to binding Rb and was constructed by cloning a Stu I-Hpa I RIZ fragment (nucleotide 795-3068) into vector pBSK+ to make pBSK+SH. An Eco RI fragment was removed from pBSK+SH and ligated into pGEX-KG to produce vector pKG7.1S containing GST-RIZ (245-573).

The binding between purified GST-RIZ (245-573) and the above radiolabeled Rb wild-type and deletion mutants were determined by immunoprecipitation with an anti-RIZ antiserum followed by SDS-PAGE and autoradiography. The antiserum was generated by injecting rabbits with the purified GST fused to a fragment of RIZ from amino acid position 245-573 (RIZ (245-573)), which contains zinc fingers 1-3, according to commonly used procedures (see Harlow and Lane, supra, 1988). GST-RIZ (245-573) used for immunizing rabbits was produced by expression of plasmid pKG7.1S in E. coli strain XL-1 blue. The bacteria were lysed and the GST-RIZ fusion protein isolated by glutathionine agarose column chromotography. pKG7.1S was constructed by ligating the 1.9 kb RIZ insert from pB7.1 into vector pGEX-KG. The resulting plasmid was linearized with Spe I, treated with Klenow fragment of DNA polymerase I and religated, thereby introducing a stop codon at the former Spe I site (nucleotide 1876).

The anti-RIZ antiserum specifically bound to in vitro translated RIZ (245-883) expressed from pB7.1. This binding was inhibited by the addition of the immunogen, GST-RIZ (245-573).

Figures 5A, 5B:
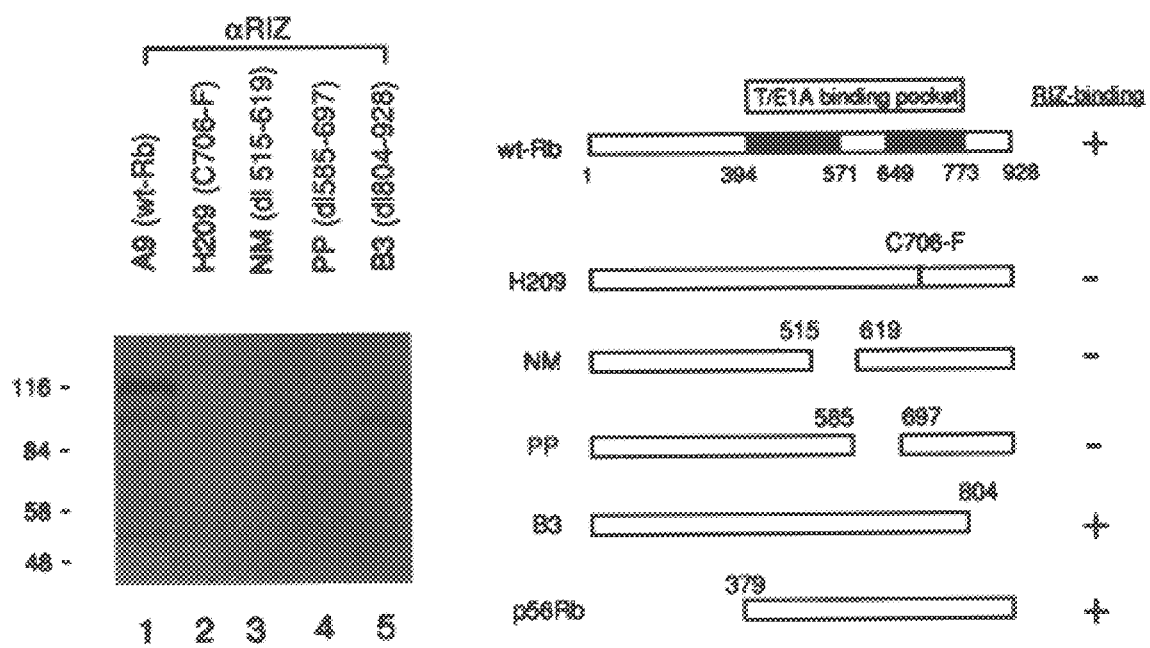
FIG. 5A and 5B: Use of Rb deletion mutants to map the RIZ binding site of Rb.

Purified GST-RIZ (245-573) showed binding to wild-type Rb and the B3 mutant of Rb, which contains a deletion C-terminal to the Rb binding pocket, but failed to bind three different forms of Rb having a deletion within the pocket (FIG. 5A). These results indicate that the Rb pocket, which was initially defined for its role in binding of oncoproteins such as the large T antigen or E1A, also is required for binding to RIZ. RIZ-binding by Rb does not require the C-terminal sequence distal to the pocket, as do certain cellular proteins such as E2F (see Huang et al., DNA Cell Biol., 11:539–548 (1992); Qin et al., Genes Devel., 6:953–964 (1992)) and c-Abl oncoprotein (see Welch and Wang, Cell 75:779–790, (1993)). The binding results map the C-terminal boundary of the RIZ-binding domain of Rb to residue 803 of Rb, in close proximity to the beginning of the N-terminal boundary of the Rb pocket (FIG. 5B).

Rat RIZ was tested for binding to Rb in HT1080 cells (ATCC #ICCL 121). The cells were grown in DMEM supplemented with 10% fetal calf serum. Cells were lysed in ELB buffer (50 mM HEPES, pH 7.5, 250 mM NaCl, 0.1% NP-40) supplemented with 5 mM EDTA, 50 mM NaF, 1 mM Na orthovandate, 1 mM of DTT, aprotinin, leupeptin, and PMSF. The lysate was cleared of cell debris by centrifugation at 12,000 rpm for 10 min in a microfuge.

Binding between 4 μg GST-RIZ (215-462) and Rb from HT1080 cell extract was evaluated by first mixing the two, then binding GST-RIZ and any associated Rb to glutathione-agarose beads. The beads were washed in binding buffer and the bound complexes were eluted by boiling in SDS buffer and analyzed by immunoblotting with anti-Rb antiserum. Immunoblotting was performed by standard techniques (see, for example, Harlow and Lane, supra, 1988).

Figure 6:
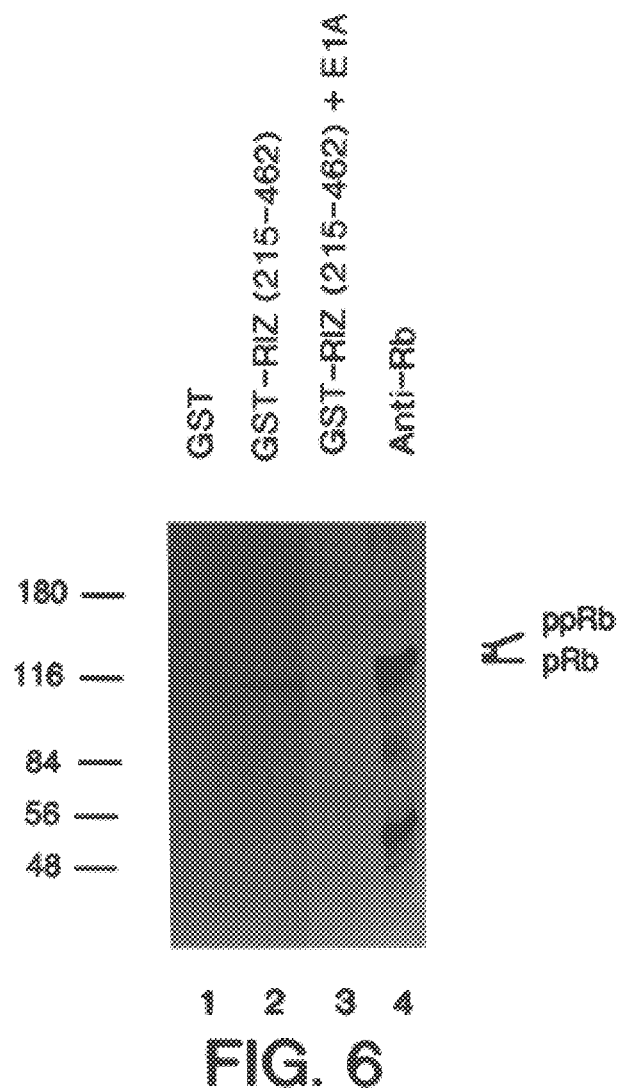
FIG. 6 shows in vitro binding of Rb from HT1080 cells with purified rat RIZ (a.a. position 215-462) fused C-terminal to glutathionine S-transferase (GST). The positions of hypophosphorylated Rb (pRb) and phosphorylated Rb (ppRb) from HT1080 cell extract are indicated in lane 4. Numbers to left indicate the migration of molecular weight markers (kilodaltons).

GST-RIZ (215-462) bound to the fastest migrating forms of Rb, representing hypophosphorylated Rb (FIG. 6, lane 2). The specificity of the interaction between RIZ and hypophosphorylated Rb was demonstrated by showing that the addition of a source of E1A protein inhibited binding (FIG. 6, lane 3). A cell lysate from 293 stably transfected to express E1A was used as the source of E1A.

EXAMPLE III

Structural and Functional Comparison Between RIZ and E1A

The similarity in sequence of particular domains between RIZ and Adenovirus E1A (see FIG. 2A) and the shared property of Rb binding indicated significant structural similarity between RIZ and E1A. To investigate this relationship further, the anti-RIZ antiserum raised against the GST-RIZ (245-573) fusion protein containing the cr2, ce1 and part of the cr1 motifs, was tested for crossreactivity with E1A. For these experiments, E1A was labeled with $^{35}$S-methionine during in vitro transcription/translation using methods described above.

Anti-RIZ antiserum crossreacted weakly with E1A (not shown). To further verify binding between anti-RIZ and E1A, the crossreactive antibodies from the anti-RIZ antiserum were purified by affinity chromatography on a column containing E1A 12S protein. The column was prepared by coupling Affi-gel 10™ beads (Bio-Rad Laboratories, Hercules, Calif.) with the purified GST-E1A 12S fusion protein expressed from pGSTE1A12S (Taylor et al., *Mol. Cell. Biol.* 13:4714–4727 (1993), which is incorporated herein by reference). Antibody affinity purification was conducted by high pH elution according to standard procedures (see Harlow and Lane, supra, 1988).

Anti-RIZ antibodies purified from the E1A affinity column were tested for binding to RIZ and E1A. Both proteins were bound by the antibodies, confirming the original crossreactivity of the anti-RIZ antiserum with E1A 12S (not shown). The E1A-affinity purified RIZ antibodies were designated "anti-cell" for crossreacting E1A antigen.

Anti-ce1 antibodies were tested for binding to various deletion mutants of RIZ and E1A 12S in order to map the location of the ce1 epitope on each molecule. A RIZ mutant truncated after residue 304 (RIZ304) was produced by in vitro transcription/translation of a BAM HI digested fragment derived from a BAM H1 mutant of pCMVRIZ. A T7 GEN™ mutagenesis kit (U.S. Biochemical) was used to introduce a Bam HI restriction site into pCMVRIZ at RIZ nucleotide 1067 using the primer 5'-TTCACACCGG ATC-CCCGGCT CTTTCGC-3' (SEQ ID NO: 12). The Bam HI fragment was then excised and cloned into pRc-CMV to yield a vector encoding RIZ304.

A RIZ mutant truncated after residue 308 (RIZ308) was produced by PCR using full-length RIZ as the template and an upstream T7 primer (Stratagene) and a downstream RIZ primer 5'-TGGCTCTTCT AATAAGTC-3' (SEQ ID NO: 13). The PCR fragment was cloned into pCRSK+ (Stratagene) and used to produce the RIZ318 polypeptide by in vitro T7 transcription/translation.

E1A 12S, truncated at residue 223 (E1A223) was produced by generating a PCR fragment of E1A using an upstream SP6 primer (Stratagene) a downstream E1A primer 5'-GATACATTCC ACAGCCTG-3' (SEQ ID NO: 19) and the plasmid pGEM1Ad5E1A12S as template. The resulting PCR fragment was cloned into pCRSK+, which was used to direct the synthesis of the mutant E1A 12S protein by SP6 in vitro transcription/translation. The full length E1A 12S (E1A243) was produced from vector pGEM1Ad5E1A12S by in vitro transcription/translation as described above for the other vectors.

Anti-ce1 antibody bound to RIZ truncated at residue 318 but failed to react with RIZ truncated at residue 304 (not shown). These results indicate that the ce1 crossreactive antigenic determinant lies within residues 304 to 318 of RIZ. Anti-ce1 antibody bound to full length E1A (E1A243) but failed to react with the C-terminal deletion mutant of E1A (E1A223; not shown). These results indicate that the ce1 epitope is located within the C-terminal 20 amino acids of E1A 12S.

The regions of RIZ and E1A 12S that contain the ce1 epitope show significant amino acid sequence homology (FIG. 2A). The sequence $^{312}$EDLLEE (SEQ ID NO: 20) in RIZ and the sequence $^{224}$EDLLNE (SEQ ID NO: 21) in E1A are likely sites for the ce1 epitope. To evaluate this possibility, an 11 amino acid peptide encompassing residues 310-320 in RIZ (ce1peptide) KPEDLLEEPQS (SEQ ID NO: 7) and an overlapping 11 amino acid control peptide encompassing residues 304-314 containing the cr2 core motif of RIZ, peptide EIRCEEKPEDL (SEQ ID NO: 6), were synthesized by solid phase peptide synthesis and tested for their ability to block binding between anti-ce1 antibody and RIZ or E1A.

The ce1 peptide inhibited binding between anti-ce1 antibody and either $^{35}$S-RIZ318 or $^{35}$S-E1A 12S (E1A243); the cr2 peptide was not inhibitory (not shown). These experiments indicated that the ce1 epitope is located in the sequence $^{312}$EDLLEE (SEQ ID NO: 20) in RIZ and the homologous sequence $^{224}$EDLLNE (SEQ ID NO: 21) in E1A.

Anti-ce1 was tested for binding to a preformed RIZ-Rb complex to determine if the ce1 epitope is directly involved or closely associated with regions in the RIZ-Rb binding interface. In these experiments, $^{35}$S-labeled full-length Rb was preincubated with in vitro translated RIZ (215-462) to form the RIZ-Rb complex prior to adding anti-ce1 antibody for immunoprecipitation. In these experiments, the GST portion of GST-RIZ (215-462) had been previously removed by thrombin cleavage and was purified from any residual uncleaved fusion protein by adsorption with glutathionine-agarose.

The anti-ce1 antibody bound to the preformed RIZ-Rb complex (not shown). Although the binding could be characterized as weak, this was similar in reactivity with anti-ce1 binding with RIZ. Because no evidence of RIZ homo-oligomer formation was observed, Rb likely interacts directly with RIZ that also was bound by anti-ce1. The failure to observe homo-oligomer formation was based on the lack of binding between GST-RIZ (215-462) and $^{35}$S-labeled full length RIZ.

The above binding study also was performed in reverse order by first precomplexing $^{35}$S-labeled RIZ (1-575) with full-length Rb, then testing the complex for binding to anti-ce1 antibody. The result showed that the RIZ fragment bound anti-ce1 antibody regardless of whether RIZ had complexed with Rb (not shown). These experiments indicate that the ce1 epitope is not significantly involved in the interface between RIZ and Rb in the RIZ-Rb complex.

EXAMPLE IV

DNA- And GTP-Binding Activities of RIZ

To evaluate whether the zinc finger domains of RIZ can bind to DNA, the RIZ finger motifs 1 to 3 from amino acid position 245-573 or finger 4 to 6 from amino acid position 1114-1260 were expressed as GST fusion proteins, GSTZ13 and GSTZ46, respectively. The GST-RIZ fragments were purified by glutathionine agarose chromatography (Guan and Dixon, *Anal. Biochem.* 192:262–267 (1991), which is incorporated herein by reference) and evaluated for binding in a filter-based DNA-binding assay (Sukegawa and Blobel, *Cell* 72:29–38 (1993), which is incorporated herein by reference). To obtain GSTZ46, a fragment encoding RIZ (1114-1260) was made by PCR using primers 5'-GTGGTCCAAG AAACATTC-3' (SEQ ID NO: 17) and 5'-TCGTGTAAAG CTCTTCAG-3' (SEQ ID NO: 18) and pCMVRIZ as template. The PCR fragment was cloned into pBKS+, then into pGEX-KG (Guan and Dixon, supra, 1991).

The filter-based DNA binding assay was performed by electrophoresing 0.5 μg of purified GST or GST-RIZ fusion proteins by SDS-PAGE and transferring the proteins to nitrocellulose. The proteins were renatured by incubating the nitrocellulose for 3 hr in binding buffer (50 mM Tris-HCl, pH 8, 100 mM KCl, 0.1% Triton X-100™, 10% glycerol, and 0.1 mM $ZnCl_2$). $^{32}$P-labeled, randomly sheared rat ovary genomic DNA was added to the buffer and the nitrocellulose was incubated for an additional 3 hr. Blots were washed 5 times in binding buffer, dried, then autoradiographed. In some experiments, the binding buffer contained 10 mM EDTA and 2 mM DTT but no $ZnCl_2$.

Figures 7A, 7B, 7C:
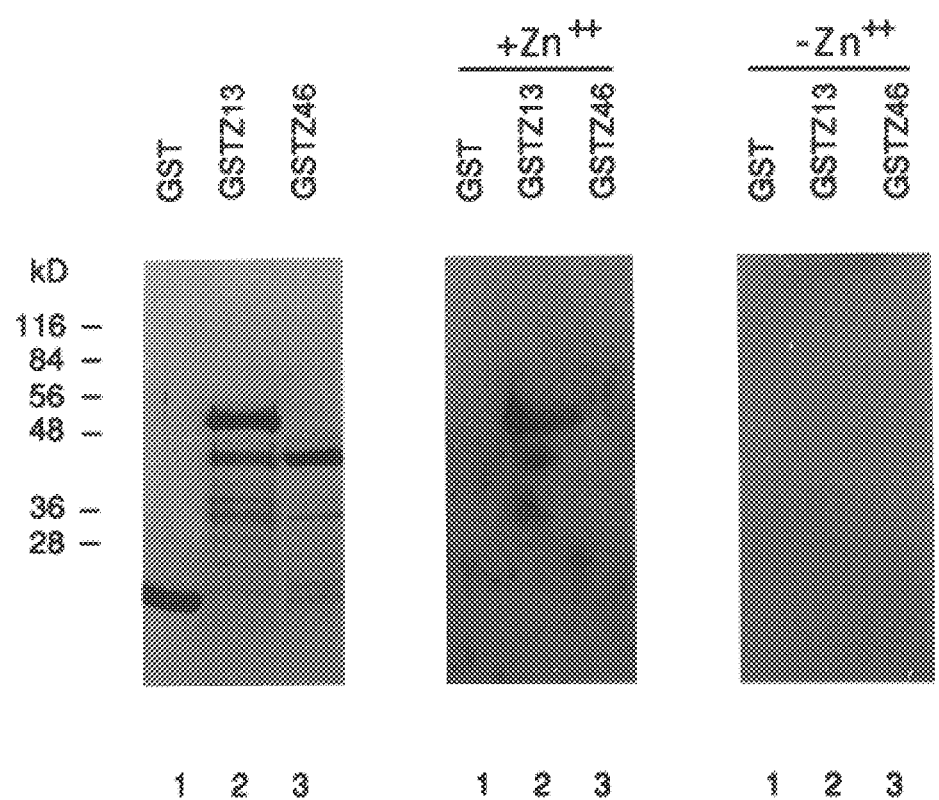
FIGS. 7A to 7C demonstrate that rat RIZ protein binds DNA.

The DNA filter binding assay showed that GSTZ13, containing zinc fingers 1 to 3 bound to rat DNA while GSTZ46, containing zinc fingers 4 to 6 did not bind (FIG. 7A and 7B). In addition, RIZ fragment containing zinc fingers 1–3 bound to DNA in a $Zn^{++}$ ion dependent manner (FIG. 7). These results indicate that RIZ zinc finger domains 1 to 3 are active in binding DNA.

The GTPase domain of RIZ, which was defined by sequence homology, was evaluated to determine if it was functionally active. For these studies, a fragment of RIZ from amino acid position 760-949 (RIZ 760-949), containing the putative GTPase domain was expressed as a fusion to GST from the plasmid pKG-G and tested for binding to radiolabeled nucleotides. pKG-G was produced by PCR amplification of the nucleotide sequence encoding RIZ (760-949) using primers 5'-TCTCCACAGC ACAGCCCT-3' (SEQ ID NO: 15), and 5'-GGATAAGGAG GCTGTCTG-3' (SEQ ID NO: 16) and pCMVRIZ as template. The fragment was cloned into pBSK+ and then into pGEX-KG, expressed and purified by glutathionine-agarose as described above. GST was also expressed from vector pGEX-KG and purified as described above.

To measure GTP-binding, 0.5 μg of GST-RIZ or control GST proteins were separated by SDS-PAGE and blotted onto nitrocellulose. Proteins were renatured in GTP-binding buffer (50 mM Tris-HCl, pH8, 100 mM KCl, 10% glycerol, 0.1% Triton X-100, and 2 mM $ZnSO_2$). The nitrocellulose was incubated for 30 min in GTP-binding buffer and then for 2 hr in GTP-binding buffer containing 1 μM α-$^{32}$P-GTP (800 Ci/mmol). The nitrocellulose was washed 5 times in GTP-binding buffer, dried and autoradiographed. In some samples, 20 mM unlabeled nucleotides were incubated with the nitrocellulose for 1 hr prior to the addition of α-$^{32}$P-GTP.

Figure 8A:
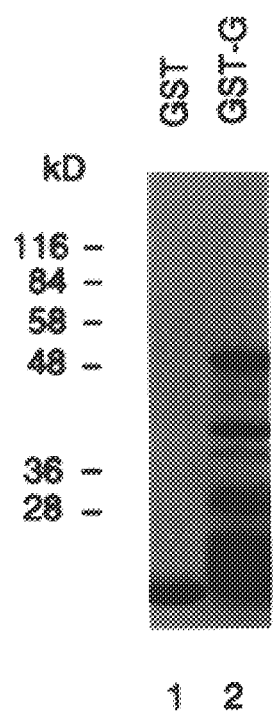
FIGS. 8A and 8B show the GTP-binding activity of rat RIZ GTPase domain (a.a. position 760-949).
Figure 8B:
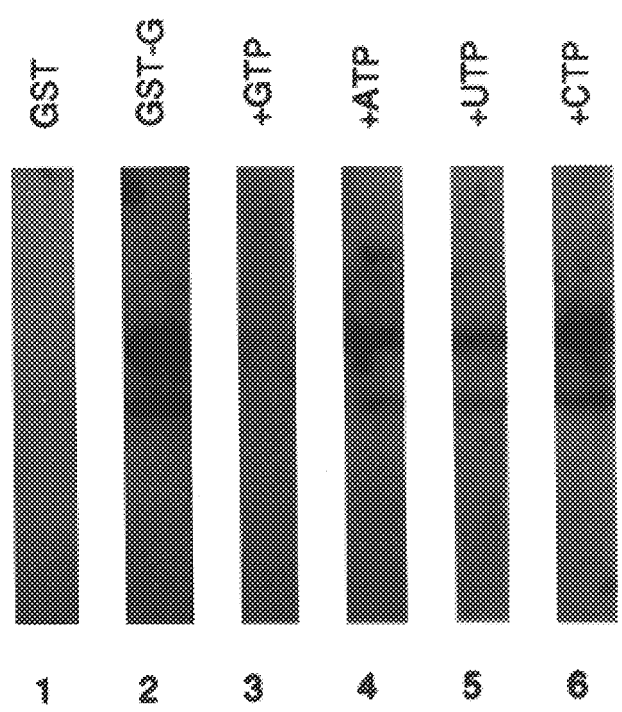

The RIZ GTPase fusion protein (GST-G), but not the control GST-protein, bound to radiolabeled GTP (FIG. 8A and lanes 1 and 2 of FIG. 8B). Binding was specific for GTP, as an excess amount of unlabeled GTP inhibited binding of RIZ GTPase to radiolabeled GTP but excess unlabeled ATP, CTP, or UTP did not effect binding (FIG. 8B, lanes 3–6). These data indicate that the GTPase domain of RIZ is functionally active.

EXAMPLE V

Expression of RIZ in Cells, Tissues and Organs

This example provides methods to identify nucleic acid molecules encoding a RIZ in mammalian cells, tissues and organs.

RNA samples were obtained from rat tissues and from the mouse pituitary cell line Att-20 (ATCC #CCL 89) by extraction with RNAzol (Biotecx, Houston Tex.) following manufacturer's procedures and purification of the mRNA by oligo dT cellulose chromatography using an oligo dT mRNA kit (Qiagen) using standard procedures. mRNA was also extracted as described above from a variety of human cell lines obtained from the American Type Culture Collection (Rockville Md.). Northern blotting was performed using these various mRNAs and hybridization with a $^{32}$P-labeled rat RIZ (representing a.a. positions 245-883) according to standard procedures (Sambrook et. al. supra, 1989).

Figure 11A:
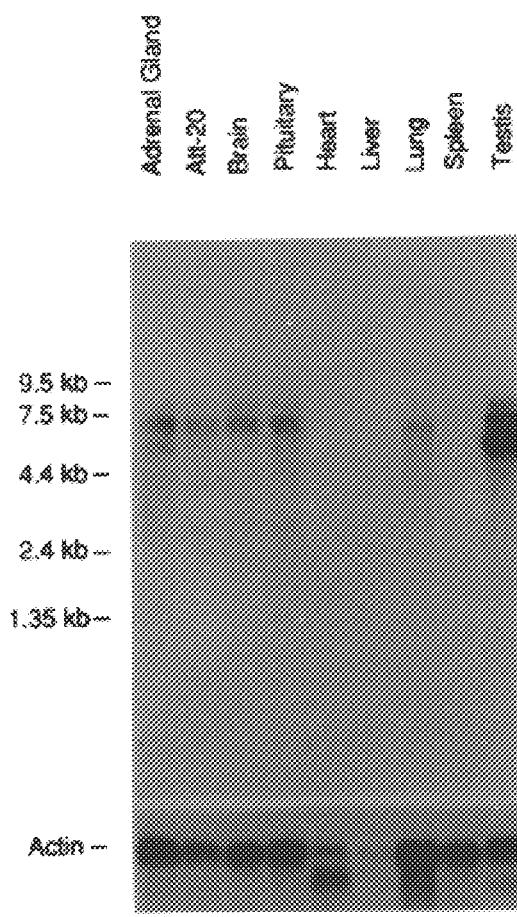
FIGS. 11A and 11B show RIZ mRNA expression in adult and fetal rat tissues, as indicated. Relative amounts of RNA loaded were compared by probing for Actin (see bottom of each blot). Numbers to the left of each figure indicate position of molecular weight markers as indicated (Kb: kilobases).

Northern blotting showed a major 7.2 kb major RIZ mRNA species primarily localized to rat neuroendocrine tissues (FIG. 11A). The testes showed a 5 kb mRNA species, which is smaller than the RIZ mRNA detected in the other organs or tissues.

Figure 11B:
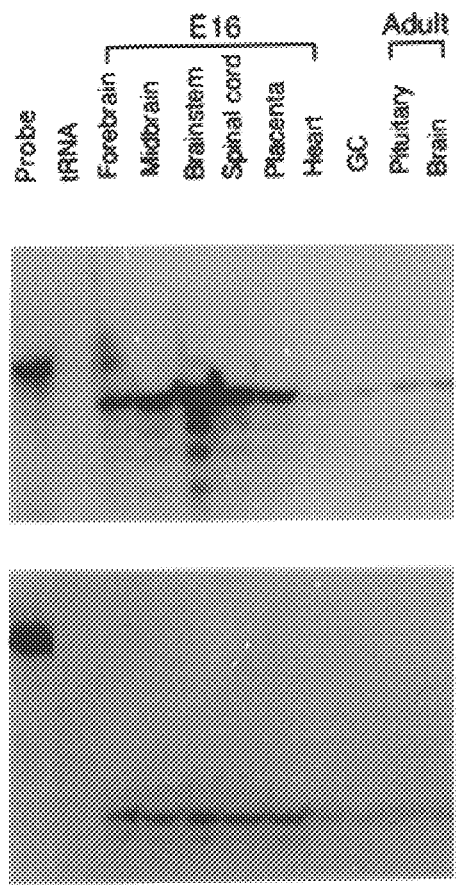

Further evaluation of mRNA expression was performed using an RNase protection method. The method was performed according to standard procedures using a $^{32}$P-labeled rat RIZ (representing a.a. position 463-574) was used as probe. The results showed abundant levels of RIZ mRNA in various neural tissues of a 16 day rat fetus as well as the placenta (FIG. 11B). In contrast, little if any mRNA was detected in adult rat tissues by this method.

RNase protection showed that RIZ mRNA was detectable in the human retinoblastoma cell lines, Y79 and Weri-Rb-1, with lower levels of detection in a variety of other human cell lines (FIG. 12). These results indicate that RIZ mRNA is expressed in large amounts in neuroendocrine related tissues of mammals and can be involved in fetal development.

Several segments of human RIZ cDNA, encompassing the full length coding region were used as probes to screen a human placental genomic cosmid library to isolate the RIZ gene. Several genomic clones were isolated and the segments encoding RIZ were localized within the clones by restriction mapping and nucleotide sequencing. The genomic clones showed that the sequence encoding RIZ is distributed across eight exons in the gene, with the majority of RIZ sequence (4.3 kb) contained in exon 7.

EXAMPLE VI

Analysis of the RIZ Gene in Normal and Tumor Cells

This example provides methods to detect the RIZ gene by direct chromosomal analysis and to evaluate mutations in the RIZ gene in tumor cells.

A. Chromosomal Localization of the Human RIZ Gene

A cosmid clone with a 35 kb insert that contains exons 7 and 8 was used as a probe for fluorescence in situ hybridization (FISH) on R-banded metaphase chromosomes to detect the chromosomal localization of the human RIZ gene. The method for FISH was performed as described previously (Takahashi et al., *Human Genetics* 88:119–121 (1991), which is incorporated herein by reference)l. Cot-1 DNA (BRL, Gaitherburg Md.) was used for the suppression of repetitive sequences present in this clone according to methods described by Lichter et al., (Lichter et. al., *Proc. Natl. Acad. Sci., USA* 87:6634–6638 (1990), which is incorporated herein by reference) using a 20 fold excess of Cot-1 DNA. Ektachrome film (Kodak, ASA100) was used for the microphotography (filter combination, Nikon B-2A).

Of 100 R-banded metaphase plates evaluated by the FISH method, 52 plates showed hybridization of the probe to both chromatids of chromosome 1 at band p36.13–p36.23, 44 plates showed hybridization of the probe only to one chromatid of chromosome 1, and four plates showed no hybridization.

Further localization of the RIZ gene to chromosome 1p36 was accomplished at the molecular level by YAC cloning. A CEPH-derived human mega-YAC library (CEPH, France) was screened by PCR using two oligonucleotide primers to amplify a 290 bp fragment within the RIZ exon 7. YAC DNA was amplified in a total volume of 10 μl containing 1×PCR buffer (50 mM KCl/10 mM Tris-HCl, pH-8.3/1.5 mM MgCl$_2$), 200 μM of each dNTP, 0.3 μM of each primer (SSO 81: 5'CCAGAACCAGACGAGCGATT3' (SEQ ID NO: 92) and SSO 82: 5'AGTTCTGGGGATTTGCATG3' (SEQ ID NO: 93)), 0.2 U Taq DNA polymerase (Perkin Elmer, Norwalk, Conn.). One of the primers was end-labeled using $^{32}$P-γ-ATP and T4 polynucleotide kinase. The PCR fragments were analyzed by acrylamide gel electrophoresis followed by autoradiography.

PCR screening of the CEPH human mega-YAC library for RIZ gene sequences identified two YAC clones, 796H4 and 807H7. A search of Genethon human genome database (Genethon, Paris France) showed that the clones contained the polymorphic marker D1S228, which maps to chromosome 1p36 (Gyapay et al., *Nat. Genet.* 7:246–339 (1994); Weissenbach et al., *Nature* 359:794–801 (1992) and Cohen et al., *Nature* 366:698–701 (1993), each of which is incorporated herein by reference)). Thus, these results indicate that the RIZ gene is localized to chromosome 1p36.

B. Allele-Specific RIZ Expression in Human Melanoma Cells

Genomic DNA from blood and placental samples of normal subjects and tumor cell lines were prepared by incubating cells for 1 hr at 55° C. in 50 mM Tris-HCl, pH 8.0/100 mM EDTA/0.5% SDS/500 μg/ml Proteinase K. After phenol/chloroform and chloroform extraction, the DNA was precipitated. RNA was prepared from a pellet of 5–10×10$^6$ PBS washed cells or from fetal tissues using RNAzol (Biotecx Laboratories, Houston Tex.).

Southern blots and were performed on melanoma cell DNA and RNA, respectively, using a RIZ cDNA a 1 kb human RIZ cDNA probe (1.1). The results showed identification of the appropriate sized bands for the RIZ gene and mRNA transcripts in the melanoma cells, indicating no gross abnormalities in the RIZ gene in these cells.

To determine whether both alleles of RIZ were active in melanoma cells, the frequency of the two allelic variants of RIZ were determined for melanoma and compared with the frequency in the population. RIZ genotyping was performed by amplification of a 290 bp fragment representing RIZ (230-330) using PCR on genomic DNA isolated from 28 normal individuals and 26 human melanoma cell lines. PCR amplification of the 290 bp fragment was performed on 100 ng of genomic DNA in a total volume of 50 μl containing 1×PCR buffer, 200 MM of each dNTP, 0.3 μM of each primer (SSO 81+SSO 82), and 1 U of Taq DNA polymerase (Perkin Elmer). The PCR product was sequenced to determine the codons encoding RIZ a.a. position 283. The RIZ D283 allele encodes an Asp residue at a.a. position 283 by the codon GAT, while the RIZ E283 allele encodes a Glu residue at a.a. position 283 by the codon GAA.

Genotyping of DNA from 28 normal individuals showed that fifteen were homozygous for the RIZ D283 allele (53%) three were homozygous for the E283 allele (10%) and ten were heterozygous (35%). Thus, the overall frequency of the RIZ E283 allele in the population of normal individuals studies was estimated to be about 28.5%.

Genotyping the DNA of 26 melanoma cell lines showed that fifteen were homozygous for the RIZ D283 allele (57%), five were homozygous for RIZ E283 (19%) and six were heterozygous (23%). This reduced frequency of heterozygous alleles in the population of melanoma cell lines tested (23%) compared to normal individuals tested (35%), indicates that a loss of heterozygosity occurs at the 1p36 locus in human melanoma.

RNA samples from the 6 heterozygous melanoma cell lines were sequenced to determine if both alleles were transcribed in the cell. Sequencing was performed on DNA products produced by reverse transcription-PCR (RT-PCR) amplification using specific RIZ primers. RT-PCR amplification was performed according to the manufacturer's instructions (GeneAmp RNA PCR kit, Perkin Elmer). A 640 bp fragment encoding RIZ exons 5–7 was obtained from transcription of 1 μg of total RNA using the SSO 82 primer (SEQ ID NO: 93) and PCR amplification using the SSO 24 primer (5'GCGAGGAGCTCCTGGTCTGG3'; SEQ ID NO: 92) and the SSO 82 primer (SEQ ID NO: 93). The amplified fragment was gel purified and sequenced using primer SSO 82 and a CircumVent™ Thermal Cycle DNA Sequencing kit (New England Biolabs, Mass.). The sequencing products were analyzed on a 6% sequencing gel.

Sequencing of amplified and transcribed RIZ mRNA from heterozygous melanoma cell lines showed that both RIZ alleles were transcribed in four of the lines while only the E283 RIZ allele was detected as transcribed in cell line HT144 (ATCC #HTB 63) and SK-MEL-23. In contrast, sequencing of amplified and transcribed mRNA from RIZ heterozygotes representing seven non-melanoma cell lines and two normal human placental tissues showed that both RIZ alleles were transcribed. Sequence analysis of the expressed allele in HT144 and SK-MEL-23 melanoma cells revealed no mutations in the RIZ encoding sequence. RIZ mRNA amplification was accomplished in 15 of 15 melanoma cell lines analyzed, indicating that homozygous RIZ gene inactivation was not present in this sample.

Regions in human chromosome 1 in the melanoma cell lines HT144 and SK-MEL-23 were evaluated for gross deletions to determine a genetic basis for the failure of these cells to produce detectable mRNA encoding the RIZ D283 allele. Gross deletion in chromosome 1 was determined by PCR amplification of polymorphic (C-A)$_2$ repeat microsatellite markers, including D1S228, D1S489 and D1S507. D1S228 is the only genetic marker in the RIZ YAC clone 796H4 that has an insert of 340 kb, indicating that the distance between RIZ and D1S228 is less than 340 kb. D1S489 is ~9-centamorgan (cM) telomeric and D1S507 ~5-cM centromeric from D1S228 (Gyapay et al., supra, 1994). Oligonucleotide primer pairs for D1S223, D1S489 and D1S507 were used to amplify 100 ng of genomic DNA. One primer was end-labeled with $^{32}$P and the amplified fragments were analyzed by sequencing and autoradiography.

PCR amplification of chromosome 1 microsatellite markers in the melanoma cell line DNA showed two different length fragments of the expected size range for each of the three markers examined, indicating heterozygosity at all three loci. These results showed that loss of transcription of the D283 allele in HT144 and SK-MEL-23 cells was not likely due to a gross deletion in the genomic DNA near the RIZ allele.

The 6 melanoma cell lines heterozygous for RIZ were evaluated to determine the amount of RIZ protein produced by the cells. RIZ protein level was estimated qualitatively by immunoprecipitation of RIZ from cell extracts with anti-RIZ antibody followed by immunoblotting the isolated RIZ with the anti-RIZ antibody. The melanoma cells lines HT144 and SK-MEL-23 produced about 50% less RIZ protein than the other melanoma cell lines tested. These data indicate that the loss of expression of the RIZ D283 allele in these cell lines results in a decrease in overall expression of RIZ in the cell.

Although the invention has been described with reference to the above-provided examples, it should be understood that various modifications can be made without departing from the spirit of the invention. Accordingly, the invention is limited only by the claims that follow.

I claim:

1. An isolated nucleic acid molecule encoding a human retinoblastoma protein-interacting zinc finger protein, comprising the nucleotide sequence shown in FIG. 9 (SEQ ID NO: 3).

2. The nucleic acid molecule of claim 1, wherein thymine at nucleotide position 849 in SEQ ID NO: 3 is replaced by adenine.

3. An isolated nucleic acid molecule encoding rat retinoblastoma protein-interacting zinc finger protein, comprising the nucleotide sequence shown in FIG. 1 (SEQ ID NO: 1).

4. An isolated nucleic acid molecule encoding a retinoblastoma protein-interacting zinc finger protein, comprising a nucleotide sequence encoding the amino acid sequence shown in FIG. 9 (SEQ ID NO: 4).

5. An isolated nucleic acid molecule encoding a retinoblastoma protein-interacting zinc finger protein, comprising a nucleotide sequence encoding the amino acid sequence shown in FIG. 1 (SEQ ID NO: 2).

6. An isolated nucleic acid molecule encoding a mutant human retinoblastoma protein-interacting zinc finger protein, comprising a nucleotide sequence encoding the amino acid sequence shown in FIG. 9 (SEQ ID NO: 4), except wherein the cysteine at amino acid position 106 is replaced by tyrosine.

7. A method of reducing the growth of a tumor cell having a mutant retinoblastoma protein-interacting zinc finger protein (RIZ), comprising the steps of:

a. introducing the nucleic acid molecule of claim 1, 2, 3, 4 or 5 into the tumor cell in vitro; and b. expressing said RIZ in said tumor cell, wherein expression of said RIZ reduces the growth of said tumor cell.

8. The method of claim 7, wherein said tumor cell is selected from the group consisting of a neuroblastoma tumor cell and a melanoma tumor cell.

9. A vector, comprising the nucleic acid molecule of claim 1, 2, 3, 4, 5 or 6.

10. A host cell, containing the vector of claim 9.

* * * * *

UNITED STATES PATENT AND TRADEMARK OFFICE
CERTIFICATE OF CORRECTION

PATENT NO. : 5,811,304
DATED : September 22, 1998
INVENTOR(S) : Shi Huang

It is certified that error appears in the above-identified patent and that said Letters Patent is hereby corrected as shown below:

Column 3,
Line 49, please delete "$_{107}{}^{Glu}$" and replace therefor with -- $107^{Glu}$ --.
Line 54, please delete "glutationine" and replace therefor with -- glutathione --.

Column 5,
Line 7, please delete "indicating a role".

Column 7, TABLE 1,
Line 48, "(27)" should be under column "G2" and "(30)" should be under column "G3".
Line 59, please delete "Ray Chaudhuri and Park (1992)" and replace therefor with
-- Raychauduri and Park, Nature 359:251-254 (1992) --.

Column 9,
Line 50, please delete "glutationine" and replace therefor with -- glutathione --.

Column 13,
Line 30, please delete "Lo" and replace therefor with -- to --.

Column 17,
Line 55, please delete "lane" and replace therefor with -- Lane --.
Line 56, please insert -- and -- between "produced" and "western".

Column 22,
Line 4, please delete "vest" and replace therefor with -- test --.

Column 23,
Line 38, please delete "in" after "nucleic acids".

Column 25,
Line 9, please delete "to" and replace therefor with -- the --.
Line 40, please delete "8425" and replace therefor with -- 8125 --.
Line 63, please delete "A $S_{849}$," and replace therefor with -- $A_{849}$, --.

Column 27,
Line 19, please delete "($1_{-575}$)" and replace therefor with -- (1-575) --.
Line 37, please delete "-Glu" and replace therefor with -- Glu --.

UNITED STATES PATENT AND TRADEMARK OFFICE
CERTIFICATE OF CORRECTION

PATENT NO. : 5,811,304
DATED : September 22, 1998
INVENTOR(S) : Shi Huang

It is certified that error appears in the above-identified patent and that said Letters Patent is hereby corrected as shown below:

Column 28,
Line 44, please delete "glutathione" and replace therefor with -- glutathione --.

Column 30,
Line 2, please delete "(celpeptide)" and replace therefor with -- (cel peptide) --.

Column 32,
Line 50, please delete "reference)1" and replace therefor with -- reference) --.

Signed and Sealed this

Twenty-sixth Day of February, 2002

Attest:

JAMES E. ROGAN
Attesting Officer    Director of the United States Patent and Trademark Office

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
( A ) LENGTH: 6171 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 157..5275

( x i ) SEQUENCE DESCRIPTION: SEQ ID NO:1:

| | | | | | |
|---|---|---|---|---|---|
| GCCAAGATGG | CGGCGGCGCG | GCCGCGGGCG | CCAGGGCGAC | GGCGGCGGCT | GAGGCTCTGG | 60 |
| GCTCGCTGAA | GCGTTGGCAC | GTCGCGCTCT | GGGCTCATGT | AATCAAAGAA | GTTTCTTTGT | 120 |
| TGTGTGTATC | TTCACAGAAC | ACAACAGGAA | TTGAAA ATG CAT CAG AAC ACT GAG | 174 |
| | | | Met His Gln Asn Thr Glu |
| | | | 1             5 |

| TCT GTG GCA GCC ACT GAG ACT CTG GCT GAG GTA CCT GAA CAT GTG CTT | 222 |
| Ser Val Ala Ala Thr Glu Thr Leu Ala Glu Val Pro Glu His Val Leu |
| 10                15                  20 |

| CGA GGA CTT CCA GAG GAA GTA AGA CTT TTC CCA TCT GCA GTC GAC AAG | 270 |
| Arg Gly Leu Pro Glu Glu Val Arg Leu Phe Pro Ser Ala Val Asp Lys |
| 25                  30                35 |

| ACT CGG ATT GGT GTC TGG GCT ACT AAA CCA ATT TTA AAA GGG AAA AAG | 318 |
| Thr Arg Ile Gly Val Trp Ala Thr Lys Pro Ile Leu Lys Gly Lys Lys |
| 40                  45                50 |

| TTT GGG CCA TTT GTT GGT GAT AAG AAG AAG AGA TCC CAG GTT AGG AAT | 366 |
| Phe Gly Pro Phe Val Gly Asp Lys Lys Lys Arg Ser Gln Val Arg Asn |
| 55                60                  65                70 |

| AAT GTG TAC ATG TGG GAG GTC TAC TAC CCA AAT TTG GGG TGG ATG TGC | 414 |
| Asn Val Tyr Met Trp Glu Val Tyr Tyr Pro Asn Leu Gly Trp Met Cys |
| 75                  80                  85 |

| ATT GAT GCC ACC GAT CCG GAG AAG GGC AAC TGG CTA CGC TAT GTG AAC | 462 |
| Ile Asp Ala Thr Asp Pro Glu Lys Gly Asn Trp Leu Arg Tyr Val Asn |
| 90                  95                  100 |

| TGG GCT TGC TCA GGA GAA GAG CAG AAT TTA TTT CCA CTG GAA ATC AAC | 510 |
| Trp Ala Cys Ser Gly Glu Glu Gln Asn Leu Phe Pro Leu Glu Ile Asn |
| 105                    110                 115 |

| AGA GCC ATT TAC TAT AAA ACC TTA AAG CCA ATC GCG CCT GGC GAG GAG | 558 |
| Arg Ala Ile Tyr Tyr Lys Thr Leu Lys Pro Ile Ala Pro Gly Glu Glu |
| 120                  125                 130 |

| CTC CTG GTC TGG TAC AAT GGG GAA GAC AAC CCT GAG ATA GCA GCT GCG | 606 |
| Leu Leu Val Trp Tyr Asn Gly Glu Asp Asn Pro Glu Ile Ala Ala Ala |
| 135                 140                 145                 150 |

| ATT GAG GAA GAG CGA GCC AGC GCC CGG AGC AAG CGG AGC TCC CCG AAG | 654 |
| Ile Glu Glu Glu Arg Ala Ser Ala Arg Ser Lys Arg Ser Ser Pro Lys |
| 155                  160                 165 |

| AGC CGC AGA GGG AAG AAG AAA TCA CAC GAG AAC AAA AAC AAA GGC ATC | 702 |
| Ser Arg Arg Gly Lys Lys Lys Ser His Glu Asn Lys Asn Lys Gly Ile |
| 170                 175                 180 |

| AGA ACC CAC CCC ACA CAG CTG AAG GCA AGT GAG CTG GAC TCT ACC TTT | 750 |
| Arg Thr His Pro Thr Gln Leu Lys Ala Ser Glu Leu Asp Ser Thr Phe |
| 185                  190                 195 |

| | | | | | | | | | | | | | | | | |
|---|---|---|---|---|---|---|---|---|---|---|---|---|---|---|---|---|
| GCA | AAC | ATG | AGG | GGC | TCT | GCA | GAA | GGT | CCA | AAA | GAA | GAG | GAT | GAG | AGG | 798 |
| Ala | Asn | Met | Arg | Gly | Ser | Ala | Glu | Gly | Pro | Lys | Glu | Glu | Asp | Glu | Arg | |
| | 200 | | | | | 205 | | | | | 210 | | | | | |
| CCT | TTG | GCT | TCG | GCA | CCT | GAG | CAG | CCA | GCC | CCT | CTG | CCG | GAG | GTG | GGG | 846 |
| Pro | Leu | Ala | Ser | Ala | Pro | Glu | Gln | Pro | Ala | Pro | Leu | Pro | Glu | Val | Gly | |
| 215 | | | | | 220 | | | | | 225 | | | | | 230 | |
| AAT | CAA | GAT | GCA | GTT | CCA | CAG | GTG | GCC | ATC | CCT | CTC | CCT | GCC | TGC | GAG | 894 |
| Asn | Gln | Asp | Ala | Val | Pro | Gln | Val | Ala | Ile | Pro | Leu | Pro | Ala | Cys | Glu | |
| | | | | 235 | | | | | 240 | | | | | 245 | | |
| CCA | CAG | CCA | GAG | GTA | GAT | GGG | AAA | CAA | GAA | GTC | ACA | GAC | TGT | GAG | GTC | 942 |
| Pro | Gln | Pro | Glu | Val | Asp | Gly | Lys | Gln | Glu | Val | Thr | Asp | Cys | Glu | Val | |
| | | | 250 | | | | | 255 | | | | | 260 | | | |
| AAT | GAT | GTG | GAG | GAA | GAG | GAG | CTG | GAA | GAG | GAA | GAG | GAG | CTG | GAA | GAG | 990 |
| Asn | Asp | Val | Glu | Glu | Glu | Glu | Leu | Glu | Glu | Glu | Glu | Glu | Leu | Glu | Glu | |
| | | 265 | | | | | 270 | | | | | 275 | | | | |
| GAG | GAG | GAG | GAG | GAG | TTG | GGA | GAA | GAT | GGG | GTA | GAA | GAA | GCA | GAC | ATG | 1038 |
| Glu | Glu | Glu | Glu | Glu | Leu | Gly | Glu | Asp | Gly | Val | Glu | Glu | Ala | Asp | Met | |
| | 280 | | | | | 285 | | | | | 290 | | | | | |
| CCG | AAT | GAA | AGC | TCT | GCG | AAA | GAG | CCG | GAG | ATC | CGG | TGT | GAA | GAA | AAG | 1086 |
| Pro | Asn | Glu | Ser | Ser | Ala | Lys | Glu | Pro | Glu | Ile | Arg | Cys | Glu | Glu | Lys | |
| 295 | | | | | 300 | | | | | 305 | | | | | 310 | |
| CCA | GAA | GAC | TTA | TTA | GAA | GAG | CCA | CAG | AGC | ATG | TCG | AAT | GAA | GCT | CGT | 1134 |
| Pro | Glu | Asp | Leu | Leu | Glu | Glu | Pro | Gln | Ser | Met | Ser | Asn | Glu | Ala | Arg | |
| | | | | 315 | | | | | 320 | | | | | 325 | | |
| GAA | GAC | TCT | CCA | GAC | GTG | ACC | CCT | CCT | CCC | CAC | ACT | CCC | AGA | GCT | AGA | 1182 |
| Glu | Asp | Ser | Pro | Asp | Val | Thr | Pro | Pro | Pro | His | Thr | Pro | Arg | Ala | Arg | |
| | | | 330 | | | | | 335 | | | | | 340 | | | |
| GAG | GAG | GCC | AAC | GGT | GAT | GTA | CTT | GAG | ACA | TTT | ATG | TTT | CCG | TGT | CAG | 1230 |
| Glu | Glu | Ala | Asn | Gly | Asp | Val | Leu | Glu | Thr | Phe | Met | Phe | Pro | Cys | Gln | |
| | | 345 | | | | | 350 | | | | | 355 | | | | |
| CAC | TGT | GAA | AGA | AAA | TTT | GCA | ACG | AAG | CAG | GGG | CTA | GAG | CGT | CAC | ATG | 1278 |
| His | Cys | Glu | Arg | Lys | Phe | Ala | Thr | Lys | Gln | Gly | Leu | Glu | Arg | His | Met | |
| | 360 | | | | | 365 | | | | | 370 | | | | | |
| CAC | ATC | CAC | ATT | TCT | ACC | ATC | AAT | CAT | GCT | TTC | AAG | TGC | AAG | TAC | TGT | 1326 |
| His | Ile | His | Ile | Ser | Thr | Ile | Asn | His | Ala | Phe | Lys | Cys | Lys | Tyr | Cys | |
| 375 | | | | | 380 | | | | | 385 | | | | | 390 | |
| GGG | AAA | CGG | TTT | GGC | ACA | CAG | ATT | AAC | AGG | AGG | CGG | CAT | GAA | CGG | CGC | 1374 |
| Gly | Lys | Arg | Phe | Gly | Thr | Gln | Ile | Asn | Arg | Arg | Arg | His | Glu | Arg | Arg | |
| | | | | 395 | | | | | 400 | | | | | 405 | | |
| CAC | GAA | ACG | GGG | TTG | AAG | AGA | AGA | CCC | AGC | ATG | ACT | TTA | CAG | TCC | TCA | 1422 |
| His | Glu | Thr | Gly | Leu | Lys | Arg | Arg | Pro | Ser | Met | Thr | Leu | Gln | Ser | Ser | |
| | | | 410 | | | | | 415 | | | | | 420 | | | |
| GAG | GAT | CCA | GAT | GAT | GGC | AAG | GGG | GAA | AAT | GTT | ACT | TCT | AAA | GAT | GAG | 1470 |
| Glu | Asp | Pro | Asp | Asp | Gly | Lys | Gly | Glu | Asn | Val | Thr | Ser | Lys | Asp | Glu | |
| | | 425 | | | | | 430 | | | | | 435 | | | | |
| TCA | AGT | CCA | CCT | CAA | CTC | GGG | CAA | GAC | TGT | TTG | ATA | TTG | AAC | TCA | GAG | 1518 |
| Ser | Ser | Pro | Pro | Gln | Leu | Gly | Gln | Asp | Cys | Leu | Ile | Leu | Asn | Ser | Glu | |
| | 440 | | | | | 445 | | | | | 450 | | | | | |
| AAA | ACC | TCA | CAG | GAA | GTA | CTG | AAT | TCA | TCT | TTT | GTG | GAA | GAA | AAT | GGT | 1566 |
| Lys | Thr | Ser | Gln | Glu | Val | Leu | Asn | Ser | Ser | Phe | Val | Glu | Glu | Asn | Gly | |
| 455 | | | | | 460 | | | | | 465 | | | | | 470 | |
| GAA | GTT | AAA | GAA | CTT | CAT | CCG | TGC | AAA | TAC | TGC | AAA | AAG | GTA | TTT | GGA | 1614 |
| Glu | Val | Lys | Glu | Leu | His | Pro | Cys | Lys | Tyr | Cys | Lys | Lys | Val | Phe | Gly | |
| | | | | 475 | | | | | 480 | | | | | 485 | | |
| ACT | CAC | ACC | AAT | ATG | AGA | CGA | CAT | CAG | CGT | AGA | GTT | CAT | GAG | CGC | CAC | 1662 |
| Thr | His | Thr | Asn | Met | Arg | Arg | His | Gln | Arg | Arg | Val | His | Glu | Arg | His | |
| | | | 490 | | | | | 495 | | | | | 500 | | | |
| CTG | ATT | CCC | AAA | GGT | GTC | AGG | CGA | AAA | GGA | GGA | CTT | CTG | GAA | GAG | CCA | 1710 |
| Leu | Ile | Pro | Lys | Gly | Val | Arg | Arg | Lys | Gly | Gly | Leu | Leu | Glu | Glu | Pro | |
| | | 505 | | | | | 510 | | | | | 515 | | | | |

| | | | | | | | | | | | | | | | | |
|---|---|---|---|---|---|---|---|---|---|---|---|---|---|---|---|---|
| CAG | CCA | CCA | GCA | GAG | CAG | GCT | CCA | CCC | TCC | CAG | AAT | GTC | TAT | GTC | CCA | 1758 |
| Gln | Pro | Pro | Ala | Glu | Gln | Ala | Pro | Pro | Ser | Gln | Asn | Val | Tyr | Val | Pro | |
| | 520 | | | | 525 | | | | | 530 | | | | | | |
| AGC | ACA | GAG | CCA | GAG | GAG | GAA | GGG | GAA | ACA | GAT | GAC | GTG | TAC | ATC | ATG | 1806 |
| Ser | Thr | Glu | Pro | Glu | Glu | Glu | Gly | Glu | Thr | Asp | Asp | Val | Tyr | Ile | Met | |
| 535 | | | | | 540 | | | | | 545 | | | | | 550 | |
| GAC | ATT | TCT | AGC | AAC | ATC | TCT | GAA | AAC | CTA | AAT | TAC | TAT | ATT | GAC | GGT | 1854 |
| Asp | Ile | Ser | Ser | Asn | Ile | Ser | Glu | Asn | Leu | Asn | Tyr | Tyr | Ile | Asp | Gly | |
| | | | | 555 | | | | | 560 | | | | | 565 | | |
| AAG | ATT | CAG | ACC | AAC | AGC | AGC | ACT | AGT | AAC | TGT | GAT | GTG | ATT | GAG | ATG | 1902 |
| Lys | Ile | Gln | Thr | Asn | Ser | Ser | Thr | Ser | Asn | Cys | Asp | Val | Ile | Glu | Met | |
| | | | 570 | | | | 575 | | | | | 580 | | | | |
| GAG | TCT | AAT | TCT | GCA | CAC | TTG | TAT | GGC | ATA | GAC | TGT | CTG | CTC | ACT | CCA | 1950 |
| Glu | Ser | Asn | Ser | Ala | His | Leu | Tyr | Gly | Ile | Asp | Cys | Leu | Leu | Thr | Pro | |
| | | 585 | | | | | 590 | | | | | 595 | | | | |
| GTG | ACC | GTG | GAG | ATT | ACT | CAG | AAC | ATA | AAG | AGC | ACT | CAG | GTC | TCT | GTG | 1998 |
| Val | Thr | Val | Glu | Ile | Thr | Gln | Asn | Ile | Lys | Ser | Thr | Gln | Val | Ser | Val | |
| | 600 | | | | | 605 | | | | | 610 | | | | | |
| ACA | GAT | GAT | CTT | CTC | AAA | GAC | TCT | CCC | AGC | AGC | ACA | AAT | TGT | GAG | TCT | 2046 |
| Thr | Asp | Asp | Leu | Leu | Lys | Asp | Ser | Pro | Ser | Ser | Thr | Asn | Cys | Glu | Ser | |
| 615 | | | | | 620 | | | | | 625 | | | | | 630 | |
| AAG | AAA | CGG | AGG | ACT | GCC | AGT | CCA | CCT | GTG | CTC | CCC | AAA | ATT | AAA | ACG | 2094 |
| Lys | Lys | Arg | Arg | Thr | Ala | Ser | Pro | Pro | Val | Leu | Pro | Lys | Ile | Lys | Thr | |
| | | | | 635 | | | | | 640 | | | | | 645 | | |
| GAG | ACG | GAG | TCT | GAT | TCC | ACA | GCA | CCC | TCG | TGT | TCC | TTA | AGT | CTG | CCC | 2142 |
| Glu | Thr | Glu | Ser | Asp | Ser | Thr | Ala | Pro | Ser | Cys | Ser | Leu | Ser | Leu | Pro | |
| | | | 650 | | | | 655 | | | | | 660 | | | | |
| CTG | AGC | ATA | TCC | ACA | GCC | GAG | GTG | GTG | TCC | TTC | CAT | AAA | GAG | AAG | GGC | 2190 |
| Leu | Ser | Ile | Ser | Thr | Ala | Glu | Val | Val | Ser | Phe | His | Lys | Glu | Lys | Gly | |
| | | 665 | | | | | 670 | | | | | 675 | | | | |
| GTC | TAT | TTG | TCG | TCC | AAG | CTC | AAG | CAG | CTT | CTT | CAG | ACC | CAG | GAC | AAG | 2238 |
| Val | Tyr | Leu | Ser | Ser | Lys | Leu | Lys | Gln | Leu | Leu | Gln | Thr | Gln | Asp | Lys | |
| | 680 | | | | | 685 | | | | | 690 | | | | | |
| CTG | ACC | CTT | CCT | GCA | GGG | TTT | TCA | GCA | GCT | GAG | ATT | CCT | AAG | TTA | GGT | 2286 |
| Leu | Thr | Leu | Pro | Ala | Gly | Phe | Ser | Ala | Ala | Glu | Ile | Pro | Lys | Leu | Gly | |
| 695 | | | | | 700 | | | | | 705 | | | | | 710 | |
| CCC | GTG | TGC | GCG | TCT | GCT | CCT | GCA | TCC | ATG | TTG | CCC | GTG | ACC | TCT | AGT | 2334 |
| Pro | Val | Cys | Ala | Ser | Ala | Pro | Ala | Ser | Met | Leu | Pro | Val | Thr | Ser | Ser | |
| | | | | 715 | | | | | 720 | | | | | 725 | | |
| AGG | TTT | AAG | AGA | CGC | ACC | AGC | TCT | CCA | CCG | AGC | TCT | CCA | CAG | CAC | AGC | 2382 |
| Arg | Phe | Lys | Arg | Arg | Thr | Ser | Ser | Pro | Pro | Ser | Ser | Pro | Gln | His | Ser | |
| | | | | 730 | | | | | 735 | | | | | 740 | | |
| CCT | GCC | CTT | CGA | GAC | TTC | GGG | AAA | CCA | AAT | GAT | GGG | AAA | GCA | GCA | TGG | 2430 |
| Pro | Ala | Leu | Arg | Asp | Phe | Gly | Lys | Pro | Asn | Asp | Gly | Lys | Ala | Ala | Trp | |
| | | 745 | | | | | 750 | | | | | 755 | | | | |
| ACA | GAC | ACA | GTC | CTG | ACT | TCC | AAG | AAA | CCC | AAG | TTA | GAA | AGT | CGT | AGT | 2478 |
| Thr | Asp | Thr | Val | Leu | Thr | Ser | Lys | Lys | Pro | Lys | Leu | Glu | Ser | Arg | Ser | |
| | 760 | | | | | 765 | | | | | 770 | | | | | |
| GAC | TCA | CCA | GCA | TGG | AGT | TTG | TCT | GGG | AGA | GAT | GAA | AGA | GAA | ACC | GGA | 2526 |
| Asp | Ser | Pro | Ala | Trp | Ser | Leu | Ser | Gly | Arg | Asp | Glu | Arg | Glu | Thr | Gly | |
| 775 | | | | | 780 | | | | | 785 | | | | | 790 | |
| AGC | CCT | CCT | TGC | TTT | GAT | GAA | TAC | AAA | ATA | TCA | AAG | GAA | TGG | GCA | GCC | 2574 |
| Ser | Pro | Pro | Cys | Phe | Asp | Glu | Tyr | Lys | Ile | Ser | Lys | Glu | Trp | Ala | Ala | |
| | | | | 795 | | | | | 800 | | | | | 805 | | |
| AGT | TCT | ACT | TTC | AGC | AGT | GTG | TGC | AAC | CAA | CAG | CCA | TTG | GAT | TTA | TCC | 2622 |
| Ser | Ser | Thr | Phe | Ser | Ser | Val | Cys | Asn | Gln | Gln | Pro | Leu | Asp | Leu | Ser | |
| | | | | 810 | | | | | 815 | | | | | 820 | | |
| AGC | GGG | GTC | AAA | CAG | AAG | TCA | GAG | GGC | ACA | GGC | AAG | ACT | CCA | GTC | CCA | 2670 |
| Ser | Gly | Val | Lys | Gln | Lys | Ser | Glu | Gly | Thr | Gly | Lys | Thr | Pro | Val | Pro | |
| | | 825 | | | | | 830 | | | | | 835 | | | | |

| | | | | | | | | | | | | | | | | |
|---|---|---|---|---|---|---|---|---|---|---|---|---|---|---|---|---|
| TGG | GAA | TCT | GTA | TTG | GAT | CTC | AGT | GTG | CAT | AAA | AAG | CCT | TGC | GAT | TCT | 2718 |
| Trp | Glu | Ser | Val | Leu | Asp | Leu | Ser | Val | His | Lys | Lys | Pro | Cys | Asp | Ser | |
| | 840 | | | | | 845 | | | | | 850 | | | | | |
| GAA | GGC | AAG | GAA | TTC | AAA | GAG | AAC | CAT | TTG | GCA | CAG | CCA | GCT | GCA | AAG | 2766 |
| Glu | Gly | Lys | Glu | Phe | Lys | Glu | Asn | His | Leu | Ala | Gln | Pro | Ala | Ala | Lys | |
| 855 | | | | | 860 | | | | | 865 | | | | | 870 | |
| AAG | AAA | AAA | CCA | ACC | ACC | TGT | ATG | CTT | CAA | AAG | GTT | CTT | CTC | AAT | GAG | 2814 |
| Lys | Lys | Lys | Pro | Thr | Thr | Cys | Met | Leu | Gln | Lys | Val | Leu | Leu | Asn | Glu | |
| | | | | 875 | | | | | 880 | | | | | 885 | | |
| TAT | AAT | GGT | GTT | AGC | TTA | CCT | ACA | GAA | ACC | ACA | CCA | GAG | GTG | ACC | AGG | 2862 |
| Tyr | Asn | Gly | Val | Ser | Leu | Pro | Thr | Glu | Thr | Thr | Pro | Glu | Val | Thr | Arg | |
| | | | 890 | | | | | 895 | | | | | 900 | | | |
| AGC | CCA | AGT | CCT | TGT | AAA | TCC | CCA | GAT | ACA | CAG | CCA | GAT | CCT | GAA | CTT | 2910 |
| Ser | Pro | Ser | Pro | Cys | Lys | Ser | Pro | Asp | Thr | Gln | Pro | Asp | Pro | Glu | Leu | |
| | | 905 | | | | | 910 | | | | | 915 | | | | |
| GGT | CCT | GAC | TCA | AGT | TGC | TCA | GTC | CCC | ACT | GCT | GAG | TCT | CCA | CCT | GAA | 2958 |
| Gly | Pro | Asp | Ser | Ser | Cys | Ser | Val | Pro | Thr | Ala | Glu | Ser | Pro | Pro | Glu | |
| 920 | | | | | 925 | | | | | 930 | | | | | | |
| GTT | GTT | GGC | CCT | TCC | TCA | CCC | CCT | CTC | CAG | ACA | GCC | TCC | TTA | TCC | TCC | 3006 |
| Val | Val | Gly | Pro | Ser | Ser | Pro | Pro | Leu | Gln | Thr | Ala | Ser | Leu | Ser | Ser | |
| 935 | | | | | 940 | | | | | 945 | | | | | 950 | |
| GGT | CAG | CTG | CCT | CCT | CTC | TTA | ACC | CCC | ACA | GAG | CCT | TCT | TCC | CCT | CCC | 3054 |
| Gly | Gln | Leu | Pro | Pro | Leu | Leu | Thr | Pro | Thr | Glu | Pro | Ser | Ser | Pro | Pro | |
| | | | | 955 | | | | | 960 | | | | | 965 | | |
| CCC | TGC | CCT | CCT | GTG | TTA | ACT | GTT | GCC | ACT | CCA | CCA | CCT | CCC | CTC | CTT | 3102 |
| Pro | Cys | Pro | Pro | Val | Leu | Thr | Val | Ala | Thr | Pro | Pro | Pro | Pro | Leu | Leu | |
| | | | 970 | | | | | 975 | | | | | 980 | | | |
| CCA | ACC | GTC | CCT | CTC | TCC | CAC | CCC | TCT | TCT | GAT | GCC | TCC | CCT | CAG | CAG | 3150 |
| Pro | Thr | Val | Pro | Leu | Ser | His | Pro | Ser | Ser | Asp | Ala | Ser | Pro | Gln | Gln | |
| | | 985 | | | | | 990 | | | | | 995 | | | | |
| TGT | CCC | TCT | CCG | TTC | TCA | AAC | ACC | ACT | GCT | CAG | TCT | CCT | CTT | CCC | ATT | 3198 |
| Cys | Pro | Ser | Pro | Phe | Ser | Asn | Thr | Thr | Ala | Gln | Ser | Pro | Leu | Pro | Ile | |
| | | 1000 | | | | | 1005 | | | | | 1010 | | | | |
| CTC | TCC | CCA | ACA | GTG | TCT | CCC | TCT | CCC | TCT | CCC | ATT | CCT | CCT | GTA | GAG | 3246 |
| Leu | Ser | Pro | Thr | Val | Ser | Pro | Ser | Pro | Ser | Pro | Ile | Pro | Pro | Val | Glu | |
| 1015 | | | | | 1020 | | | | | 1025 | | | | | 1030 | |
| CCA | CTT | ATG | TCT | GCT | GCT | TCC | CCT | GGT | CCC | CCA | ACA | CTT | TCT | TCC | TCC | 3294 |
| Pro | Leu | Met | Ser | Ala | Ala | Ser | Pro | Gly | Pro | Pro | Thr | Leu | Ser | Ser | Ser | |
| | | | | 1035 | | | | | 1040 | | | | | 1045 | | |
| TCC | TCT | TCT | TCC | TCT | TCC | TTC | CCT | TCC | TCT | TCC | TGC | TCC | TCC | ACC | TCC | 3342 |
| Ser | Ser | Ser | Ser | Ser | Ser | Phe | Pro | Ser | Ser | Ser | Cys | Ser | Ser | Thr | Ser | |
| | | | | 1050 | | | | | 1055 | | | | | 1060 | | |
| CCC | TCC | CCA | CCC | CCT | CTT | TCA | GCA | GTG | TCA | TCT | GTG | GTT | TCC | TCT | GGG | 3390 |
| Pro | Ser | Pro | Pro | Pro | Leu | Ser | Ala | Val | Ser | Ser | Val | Val | Ser | Ser | Gly | |
| | | 1065 | | | | | 1070 | | | | | 1075 | | | | |
| GAC | AAC | CTG | GAG | GCA | TCT | CTG | CCT | GCA | GTA | ACT | TTC | AAA | CAG | GAG | GAG | 3438 |
| Asp | Asn | Leu | Glu | Ala | Ser | Leu | Pro | Ala | Val | Thr | Phe | Lys | Gln | Glu | Glu | |
| | 1080 | | | | | 1085 | | | | | 1090 | | | | | |
| TCA | GAG | AGT | GAA | GGT | CTG | AAA | CCC | AAG | GAA | GAG | GCC | CCA | CCT | GCA | GGG | 3486 |
| Ser | Glu | Ser | Glu | Gly | Leu | Lys | Pro | Lys | Glu | Glu | Ala | Pro | Pro | Ala | Gly | |
| 1095 | | | | | 1100 | | | | | 1105 | | | | | 1110 | |
| GGA | CAG | AGT | GTG | GTC | CAA | GAA | ACA | TTC | AGC | AAA | AAC | TTC | ATT | TGC | AAT | 3534 |
| Gly | Gln | Ser | Val | Val | Gln | Glu | Thr | Phe | Ser | Lys | Asn | Phe | Ile | Cys | Asn | |
| | | | | 1115 | | | | | 1120 | | | | | 1125 | | |
| GTC | TGT | GAA | TCG | CCT | TTT | CTT | TCC | ATT | AAA | GAC | CTA | ACC | AAA | CAT | TTA | 3582 |
| Val | Cys | Glu | Ser | Pro | Phe | Leu | Ser | Ile | Lys | Asp | Leu | Thr | Lys | His | Leu | |
| | | | | 1130 | | | | | 1135 | | | | | 1140 | | |
| TCC | GTC | CAT | GCT | GAA | GAG | TGG | CCC | TTC | AAA | TGT | GAG | TTT | TGT | GTG | CAG | 3630 |
| Ser | Val | His | Ala | Glu | Glu | Trp | Pro | Phe | Lys | Cys | Glu | Phe | Cys | Val | Gln | |
| | | | 1145 | | | | | 1150 | | | | | 1155 | | | |

```
CTG TTT AAG GTT AAG ACT GAT CTA TCA GAG CAT CGA TTT CTG CTT CAT      3678
Leu Phe Lys Val Lys Thr Asp Leu Ser Glu His Arg Phe Leu Leu His
1160                    1165                    1170

GGG GTT GGA AAT ATC TTT GTG TGT TCT GTA TGT AAG AAA GAA TTT GCC      3726
Gly Val Gly Asn Ile Phe Val Cys Ser Val Cys Lys Lys Glu Phe Ala
1175                    1180                    1185                    1190

TTC TTA TGC AAT CTG CAG CAG CAC CAG CGT GAT CTC CAC CCA GAT GAG      3774
Phe Leu Cys Asn Leu Gln Gln His Gln Arg Asp Leu His Pro Asp Glu
                1195                    1200                    1205

GTA TGC ACA CAC CAC GAG TTT GAA AGT GGG ACC CTG AGG CCC CAG AAC      3822
Val Cys Thr His His Glu Phe Glu Ser Gly Thr Leu Arg Pro Gln Asn
1210                    1215                    1220

TTC ACA GAC CCC AGC AAG GCC AAT GTT GAG CAT ATG CCA AGT TTG CCA      3870
Phe Thr Asp Pro Ser Lys Ala Asn Val Glu His Met Pro Ser Leu Pro
1225                    1230                    1235

GAA GAG CCT TTA GAA ACT TCT AGA GAG GAG GAG TTA AAT GAT TCC TCT      3918
Glu Glu Pro Leu Glu Thr Ser Arg Glu Glu Glu Leu Asn Asp Ser Ser
1240                    1245                    1250

GAA GAG CTT TAC ACG ACC ATC AAA ATA ATG GCT TCT GGA ATA AAG ACG      3966
Glu Glu Leu Tyr Thr Thr Ile Lys Ile Met Ala Ser Gly Ile Lys Thr
1255                    1260                    1265                    1270

AAG GAT CCA GAT GTT CGA CTT GGT CTC AAC CAG CAC TAC CCG AGC TTT      4014
Lys Asp Pro Asp Val Arg Leu Gly Leu Asn Gln His Tyr Pro Ser Phe
                1275                    1280                    1285

AAA CCT CCT CCA TTT CAG TAC CAC CAT CGA AAC CCT ATG GGG ATA GGG      4062
Lys Pro Pro Pro Phe Gln Tyr His His Arg Asn Pro Met Gly Ile Gly
                1290                    1295                    1300

GTG ACA GCC ACC AAC TTC ACC ACC CAC AAT ATT CCA CAG ACT TTC ACT      4110
Val Thr Ala Thr Asn Phe Thr Thr His Asn Ile Pro Gln Thr Phe Thr
            1305                    1310                    1315

ACT GCC ATC CGC TGC ACA AAG TGT GGG AAG GGC GTC GAC AAT ATG CCT      4158
Thr Ala Ile Arg Cys Thr Lys Cys Gly Lys Gly Val Asp Asn Met Pro
1320                    1325                    1330

GAG CTG CAT AAG CAT ATC TTG GCG TGT GCG TCT GCA AGT GAC AAG AAG      4206
Glu Leu His Lys His Ile Leu Ala Cys Ala Ser Ala Ser Asp Lys Lys
1335                    1340                    1345                    1350

AGG TAC ACC CCT AAG AAA AAC CCA GTG CCC CTG AAA CAA ACT GTG CAG      4254
Arg Tyr Thr Pro Lys Lys Asn Pro Val Pro Leu Lys Gln Thr Val Gln
                1355                    1360                    1365

CCC AAA AAT GGA GTG GTG GTT CTA GAC AAC TCT GGG AAA AAT GCC TTC      4302
Pro Lys Asn Gly Val Val Val Leu Asp Asn Ser Gly Lys Asn Ala Phe
                1370                    1375                    1380

AGA CGG ATG GGG CAG CCC AAG AGA CTG AGC TTC AAT GTT GAA CTG GGT      4350
Arg Arg Met Gly Gln Pro Lys Arg Leu Ser Phe Asn Val Glu Leu Gly
            1385                    1390                    1395

AAA ATG TCT CCA AAC AAG CTC AAG CTG AGT GCG CTG AAG AAG AAA AAC      4398
Lys Met Ser Pro Asn Lys Leu Lys Leu Ser Ala Leu Lys Lys Lys Asn
1400                    1405                    1410

CAG CTG GTG CAG AAG GCC ATC CTT CAG AAG AAC AGA GCC GCG AAG CAG      4446
Gln Leu Val Gln Lys Ala Ile Leu Gln Lys Asn Arg Ala Ala Lys Gln
1415                    1420                    1425                    1430

AAG GCG GAC CTG AGG GAT ACT TCC GAG GCG TCC TCA CAC ATC TGC CCG      4494
Lys Ala Asp Leu Arg Asp Thr Ser Glu Ala Ser Ser His Ile Cys Pro
                1435                    1440                    1445

TAC TGT GAC AGG GAG TTC ACA TAC ATT GGC AGC CTG AAT AAG CAT GCC      4542
Tyr Cys Asp Arg Glu Phe Thr Tyr Ile Gly Ser Leu Asn Lys His Ala
                1450                    1455                    1460

GCC TTC AGC TGT CCT AAA AAA CCT CTT TCT CCT TCC AAA AGA AAA GTT      4590
Ala Phe Ser Cys Pro Lys Lys Pro Leu Ser Pro Ser Lys Arg Lys Val
1465                    1470                    1475
```

| | | | | | | | | | | | | | | | | |
|---|---|---|---|---|---|---|---|---|---|---|---|---|---|---|---|---|
| TCC | CAT | TCG | TCT | AAG | AAA | GGT | GGC | CAT | GCA | TCA | TCT | TCT | AGC | AGT | GAC | 4638 |
| Ser | His | Ser | Ser | Lys | Lys | Gly | Gly | His | Ala | Ser | Ser | Ser | Ser | Ser | Asp | |
| | | | 1480 | | | 1485 | | | | | 1490 | | | | | |
| AGA | AAC | AGC | AGC | TGC | CAC | CCC | CGG | AGG | CGG | ACT | GCA | GAT | ACC | GAG | ATC | 4686 |
| Arg | Asn | Ser | Ser | Cys | His | Pro | Arg | Arg | Arg | Thr | Ala | Asp | Thr | Glu | Ile | |
| 1495 | | | | | 1500 | | | | | 1505 | | | | | 1510 | |
| AAG | ATG | CAG | AGC | ACG | CAG | GCA | CCC | TTG | GGC | AAG | ACC | AGA | GCT | CGG | AGT | 4734 |
| Lys | Met | Gln | Ser | Thr | Gln | Ala | Pro | Leu | Gly | Lys | Thr | Arg | Ala | Arg | Ser | |
| | | | 1515 | | | | | 1520 | | | | | 1525 | | | |
| ACA | GGC | CCC | GCC | CAG | GCC | TCA | CTG | CCC | TCC | TCG | TCC | TTC | AGA | TCC | AGA | 4782 |
| Thr | Gly | Pro | Ala | Gln | Ala | Ser | Leu | Pro | Ser | Ser | Ser | Phe | Arg | Ser | Arg | |
| | | | 1530 | | | | | 1535 | | | | | 1540 | | | |
| CAG | AAT | GTC | AAA | TTT | GCA | GCT | TCA | GTG | AAA | TCC | AAA | AAA | GCA | AGC | TCT | 4830 |
| Gln | Asn | Val | Lys | Phe | Ala | Ala | Ser | Val | Lys | Ser | Lys | Lys | Ala | Ser | Ser | |
| | | | 1545 | | | | | 1550 | | | | | 1555 | | | |
| TCA | TCC | TTG | AGG | AAT | TCC | AGT | CCC | ATA | AGA | ATG | GCC | AAA | ATT | ACT | CAC | 4878 |
| Ser | Ser | Leu | Arg | Asn | Ser | Ser | Pro | Ile | Arg | Met | Ala | Lys | Ile | Thr | His | |
| | | | 1560 | | | | | 1565 | | | | | 1570 | | | |
| GTC | GAG | GGC | AAA | AAA | CCC | AAA | GCT | GTT | GCC | AAG | AGT | CAT | TCT | GCT | CAG | 4926 |
| Val | Glu | Gly | Lys | Lys | Pro | Lys | Ala | Val | Ala | Lys | Ser | His | Ser | Ala | Gln | |
| 1575 | | | | | 1580 | | | | | 1585 | | | | | 1590 | |
| CTC | TCA | AGC | AAA | TCC | TCC | CGA | GGC | CTG | CAT | GTC | AGA | GTG | CAG | AAG | AGC | 4974 |
| Leu | Ser | Ser | Lys | Ser | Ser | Arg | Gly | Leu | His | Val | Arg | Val | Gln | Lys | Ser | |
| | | | 1595 | | | | | 1600 | | | | | 1605 | | | |
| AAA | GCT | GTC | ATA | CAG | AGC | AAG | ACT | GCC | CTG | GCC | AGT | AAG | AGG | AGA | ACA | 5022 |
| Lys | Ala | Val | Ile | Gln | Ser | Lys | Thr | Ala | Leu | Ala | Ser | Lys | Arg | Arg | Thr | |
| | | | 1610 | | | | | 1615 | | | | | 1620 | | | |
| GAC | CGG | TTC | ATA | GTG | AAA | TCT | AGA | GAG | CGC | AGC | GGG | GGC | CCA | ATC | ACC | 5070 |
| Asp | Arg | Phe | Ile | Val | Lys | Ser | Arg | Glu | Arg | Ser | Gly | Gly | Pro | Ile | Thr | |
| | | | 1625 | | | | | 1630 | | | | | 1635 | | | |
| CGA | AGC | CTT | CAG | CTG | GCA | GCT | GCT | GCG | GAC | CTG | AGT | GAA | AGC | AGG | AGA | 5118 |
| Arg | Ser | Leu | Gln | Leu | Ala | Ala | Ala | Ala | Asp | Leu | Ser | Glu | Ser | Arg | Arg | |
| | | | 1640 | | | | | 1645 | | | | | 1650 | | | |
| GAG | GAC | AGC | AGT | GCC | AGG | CAT | GAG | CTG | AAG | GAC | TTC | AGC | TAC | AGT | CTC | 5166 |
| Glu | Asp | Ser | Ser | Ala | Arg | His | Glu | Leu | Lys | Asp | Phe | Ser | Tyr | Ser | Leu | |
| 1655 | | | | | 1660 | | | | | 1665 | | | | | 1670 | |
| CGC | CTG | GCA | TCT | CGA | TGC | GGC | TCA | TCA | ACA | GCC | TCT | TAC | ATC | ACC | AGA | 5214 |
| Arg | Leu | Ala | Ser | Arg | Cys | Gly | Ser | Ser | Thr | Ala | Ser | Tyr | Ile | Thr | Arg | |
| | | | 1675 | | | | | 1680 | | | | | 1685 | | | |
| CAA | TGC | AGA | AAG | GTC | AAG | GCC | GCC | GCA | GCA | ACT | CCG | TTC | CAG | GGA | CCC | 5262 |
| Gln | Cys | Arg | Lys | Val | Lys | Ala | Ala | Ala | Ala | Thr | Pro | Phe | Gln | Gly | Pro | |
| | | | 1690 | | | | | 1695 | | | | | 1700 | | | |
| TTC | CTC | AAA | GAG | T | AGGCACTCTG | TCTGCTCCTT | AACAGCACCT | GAAGTGACCT | | | | | | | | 5315 |
| Phe | Leu | Lys | Glu | | | | | | | | | | | | | |
| | | | 1705 | | | | | | | | | | | | | |

| | | | | |
|---|---|---|---|---|
| GGAATCAGTG | AAGCCAAAGG | GACCAGCAGT | CTGCCCTGCA | GAGAGCACTG ACCTCTCCCA | 5375 |
| GTTGTGAGAG | TGAGAGAACG | AGAGAGAGAG | AGAGAGAGAG | AGAGAGAGAG AGAGAGAGAG | 5435 |
| AGAATGAGAA | TGTGTGTGTG | TGTGTGCTGG | TGCATGTGTG | TGGTCTTCAA GCCAAGGTCC | 5495 |
| CAGCCTCAGG | AGCAGGACCT | TCCCATTTCC | CGTCATCCTC | TGGATGATCC TTGGACGTGG | 5555 |
| CCCAGAACCG | TGCTCTGTGG | TGCAGCCATC | CTGCCCGGGA | GGGGCATCTC CTTCTATGCA | 5615 |
| ATTTTTTTAA | AGAGTTCCTT | GGCCCTGCTT | TGTGCTTCTT | GAGCTGTCCG TTTGCCACCA | 5675 |
| CTGGGACTTG | GATCTGGCCC | TGAGGGGTGG | GGAAGAGGGC | CTATCTAAGG ATAACCTTTC | 5735 |
| AGAGGTCAAG | CTCCCCTTCA | TGCCACCCCT | CCCCCCTGCC | CTCACCGACC TTTTCCCCAC | 5795 |
| ACTGTCTCTG | GGAATCAATA | GCAGATAGCA | TATAGATCCA | TCAGGGTTGA GCCTGAACCT | 5855 |
| CGGCCCTAGC | ACTAGGAAAT | CCCCCTTTTC | TCCCTAAGCA | ACTGGAGCCG CCAGCTTTCA | 5915 |

```
AGTCATTTCC TCCTTTGAGG TTCTAGAGTC CGAGAGTCTG CTCCGAAGTC TCTCCTGGGA      5975

ACCCGGGAGC CCTCGCACCC AGGACGCAGA CTCTGTGCCC ATTCTTAGAC CTGAGGTAGA      6035

AGAAGCAGTG TTTTGGGACG ATAGGGTGGA GGCGTGCCTA CTTTGTCTCC TCTGGTGGGA      6095

CCTCCTACAT CATTGGCATC TGAACCTTGC AAGTTCGCTG CAAAGAGAAG CAAAGGAAAA      6155

AAAAAAAAAA AAAAAA                                                      6171
```

(2) INFORMATION FOR SEQ ID NO:2:

(i) SEQUENCE CHARACTERISTICS:
        (A) LENGTH: 1706 amino acids
        (B) TYPE: amino acid
        (D) TOPOLOGY: linear (ii) MOLECULE TYPE: protein (xi) SEQUENCE DESCRIPTION: SEQ ID NO:2:

```
Met His Gln Asn Thr Glu Ser Val Ala Ala Thr Glu Thr Leu Ala Glu
 1               5                  10                  15

Val Pro Glu His Val Leu Arg Gly Leu Pro Glu Glu Val Arg Leu Phe
                20                  25                  30

Pro Ser Ala Val Asp Lys Thr Arg Ile Gly Val Trp Ala Thr Lys Pro
            35                  40                  45

Ile Leu Lys Gly Lys Lys Phe Gly Pro Phe Val Gly Asp Lys Lys Lys
        50                  55                  60

Arg Ser Gln Val Arg Asn Asn Val Tyr Met Trp Glu Val Tyr Tyr Pro
65                  70                  75                  80

Asn Leu Gly Trp Met Cys Ile Asp Ala Thr Asp Pro Glu Lys Gly Asn
                85                  90                  95

Trp Leu Arg Tyr Val Asn Trp Ala Cys Ser Gly Glu Glu Gln Asn Leu
               100                 105                 110

Phe Pro Leu Glu Ile Asn Arg Ala Ile Tyr Tyr Lys Thr Leu Lys Pro
           115                 120                 125

Ile Ala Pro Gly Glu Glu Leu Leu Val Trp Tyr Asn Gly Glu Asp Asn
       130                 135                 140

Pro Glu Ile Ala Ala Ala Ile Glu Glu Glu Arg Ala Ser Ala Arg Ser
145                 150                 155                 160

Lys Arg Ser Ser Pro Lys Ser Arg Arg Gly Lys Lys Lys Ser His Glu
                165                 170                 175

Asn Lys Asn Lys Gly Ile Arg Thr His Pro Thr Gln Leu Lys Ala Ser
            180                 185                 190

Glu Leu Asp Ser Thr Phe Ala Asn Met Arg Gly Ser Ala Glu Gly Pro
        195                 200                 205

Lys Glu Glu Asp Glu Arg Pro Leu Ala Ser Ala Pro Glu Gln Pro Ala
    210                 215                 220

Pro Leu Pro Glu Val Gly Asn Gln Asp Ala Val Pro Gln Val Ala Ile
225                 230                 235                 240

Pro Leu Pro Ala Cys Glu Pro Gln Pro Glu Val Asp Gly Lys Gln Glu
                245                 250                 255

Val Thr Asp Cys Glu Val Asn Asp Val Glu Glu Glu Leu Glu Glu
            260                 265                 270

Glu Glu Glu Leu Glu Glu Glu Glu Glu Glu Leu Gly Glu Asp Gly
        275                 280                 285

Val Glu Glu Ala Asp Met Pro Asn Glu Ser Ser Ala Lys Glu Pro Glu
290                 295                 300
```

| | | | | | | | | | | | | | | |
|---|---|---|---|---|---|---|---|---|---|---|---|---|---|---|
| Ile | Arg | Cys | Glu | Glu | Lys | Pro | Glu | Asp | Leu | Leu | Glu | Glu | Pro | Gln | Ser |
| 305 | | | | 310 | | | | 315 | | | | | | 320 | |
| Met | Ser | Asn | Glu | Ala | Arg | Glu | Asp | Ser | Pro | Asp | Val | Thr | Pro | Pro | Pro |
| | | | 325 | | | | 330 | | | | 335 | | | | |
| His | Thr | Pro | Arg | Ala | Arg | Glu | Glu | Asn | Gly | Asp | Val | Leu | Glu | Thr | |
| | | | 340 | | | | 345 | | | | 350 | | | | |
| Phe | Met | Phe | Pro | Cys | Gln | His | Cys | Glu | Arg | Lys | Phe | Ala | Thr | Lys | Gln |
| | | 355 | | | | 360 | | | | 365 | | | | | |
| Gly | Leu | Glu | Arg | His | Met | His | Ile | His | Ile | Ser | Thr | Ile | Asn | His | Ala |
| | 370 | | | | 375 | | | | 380 | | | | | | |
| Phe | Lys | Cys | Lys | Tyr | Cys | Gly | Lys | Arg | Phe | Gly | Thr | Gln | Ile | Asn | Arg |
| 385 | | | | 390 | | | | 395 | | | | | | 400 | |
| Arg | Arg | His | Glu | Arg | Arg | His | Glu | Thr | Gly | Leu | Lys | Arg | Arg | Pro | Ser |
| | | | 405 | | | | 410 | | | | 415 | | | | |
| Met | Thr | Leu | Gln | Ser | Ser | Glu | Asp | Pro | Asp | Asp | Gly | Lys | Gly | Glu | Asn |
| | | | 420 | | | | 425 | | | | 430 | | | | |
| Val | Thr | Ser | Lys | Asp | Glu | Ser | Ser | Pro | Pro | Gln | Leu | Gly | Gln | Asp | Cys |
| | | 435 | | | | 440 | | | | 445 | | | | | |
| Leu | Ile | Leu | Asn | Ser | Glu | Lys | Thr | Ser | Gln | Glu | Val | Leu | Asn | Ser | Ser |
| | 450 | | | | 455 | | | | 460 | | | | | | |
| Phe | Val | Glu | Glu | Asn | Gly | Glu | Val | Lys | Glu | Leu | His | Pro | Cys | Lys | Tyr |
| 465 | | | | 470 | | | | 475 | | | | | | 480 | |
| Cys | Lys | Lys | Val | Phe | Gly | Thr | His | Thr | Asn | Met | Arg | Arg | His | Gln | Arg |
| | | | 485 | | | | 490 | | | | 495 | | | | |
| Arg | Val | His | Glu | Arg | His | Leu | Ile | Pro | Lys | Gly | Val | Arg | Arg | Lys | Gly |
| | | | 500 | | | | 505 | | | | 510 | | | | |
| Gly | Leu | Leu | Glu | Glu | Pro | Gln | Pro | Pro | Ala | Glu | Gln | Ala | Pro | Pro | Ser |
| | | 515 | | | | 520 | | | | 525 | | | | | |
| Gln | Asn | Val | Tyr | Val | Pro | Ser | Thr | Glu | Pro | Glu | Glu | Glu | Gly | Glu | Thr |
| | 530 | | | | 535 | | | | 540 | | | | | | |
| Asp | Asp | Val | Tyr | Ile | Met | Asp | Ile | Ser | Ser | Asn | Ile | Ser | Glu | Asn | Leu |
| 545 | | | | 550 | | | | 555 | | | | | | 560 | |
| Asn | Tyr | Tyr | Ile | Asp | Gly | Lys | Ile | Gln | Thr | Asn | Ser | Ser | Thr | Ser | Asn |
| | | | 565 | | | | 570 | | | | 575 | | | | |
| Cys | Asp | Val | Ile | Glu | Met | Glu | Ser | Asn | Ser | Ala | His | Leu | Tyr | Gly | Ile |
| | | | 580 | | | | 585 | | | | 590 | | | | |
| Asp | Cys | Leu | Leu | Thr | Pro | Val | Thr | Val | Glu | Ile | Thr | Gln | Asn | Ile | Lys |
| | | 595 | | | | 600 | | | | 605 | | | | | |
| Ser | Thr | Gln | Val | Ser | Val | Thr | Asp | Asp | Leu | Leu | Lys | Asp | Ser | Pro | Ser |
| | 610 | | | | 615 | | | | 620 | | | | | | |
| Ser | Thr | Asn | Cys | Glu | Ser | Lys | Lys | Arg | Arg | Thr | Ala | Ser | Pro | Pro | Val |
| 625 | | | | 630 | | | | 635 | | | | | | 640 | |
| Leu | Pro | Lys | Ile | Lys | Thr | Glu | Thr | Glu | Ser | Asp | Ser | Thr | Ala | Pro | Ser |
| | | | 645 | | | | 650 | | | | 655 | | | | |
| Cys | Ser | Leu | Ser | Leu | Pro | Leu | Ser | Ile | Ser | Thr | Ala | Glu | Val | Val | Ser |
| | | | 660 | | | | 665 | | | | 670 | | | | |
| Phe | His | Lys | Glu | Lys | Gly | Val | Tyr | Leu | Ser | Ser | Lys | Leu | Lys | Gln | Leu |
| | | 675 | | | | 680 | | | | 685 | | | | | |
| Leu | Gln | Thr | Gln | Asp | Lys | Leu | Thr | Leu | Pro | Ala | Gly | Phe | Ser | Ala | Ala |
| | 690 | | | | 695 | | | | 700 | | | | | | |
| Glu | Ile | Pro | Lys | Leu | Gly | Pro | Val | Cys | Ala | Ser | Ala | Pro | Ala | Ser | Met |
| 705 | | | | 710 | | | | 715 | | | | | | 720 | |
| Leu | Pro | Val | Thr | Ser | Ser | Arg | Phe | Lys | Arg | Arg | Thr | Ser | Ser | Pro | Pro |
| | | | 725 | | | | 730 | | | | 735 | | | | |

```
Ser  Ser  Pro  Gln  His  Ser  Pro  Ala  Leu  Arg  Asp  Phe  Gly  Lys  Pro  Asn
               740                 745                          750

Asp  Gly  Lys  Ala  Ala  Trp  Thr  Asp  Thr  Val  Leu  Thr  Ser  Lys  Lys  Pro
          755                 760                 765

Lys  Leu  Glu  Ser  Arg  Ser  Asp  Ser  Pro  Ala  Trp  Ser  Leu  Ser  Gly  Arg
770                      775                 780

Asp  Glu  Arg  Glu  Thr  Gly  Ser  Pro  Pro  Cys  Phe  Asp  Glu  Tyr  Lys  Ile
785                      790                 795                          800

Ser  Lys  Glu  Trp  Ala  Ala  Ser  Ser  Thr  Phe  Ser  Ser  Val  Cys  Asn  Gln
               805                 810                          815

Gln  Pro  Leu  Asp  Leu  Ser  Ser  Gly  Val  Lys  Gln  Lys  Ser  Glu  Gly  Thr
               820                 825                          830

Gly  Lys  Thr  Pro  Val  Pro  Trp  Glu  Ser  Val  Leu  Asp  Leu  Ser  Val  His
               835                 840                          845

Lys  Lys  Pro  Cys  Asp  Ser  Glu  Gly  Lys  Glu  Phe  Lys  Glu  Asn  His  Leu
          850                 855                 860

Ala  Gln  Pro  Ala  Ala  Lys  Lys  Lys  Pro  Thr  Thr  Cys  Met  Leu  Gln
865                      870                 875                     880

Lys  Val  Leu  Leu  Asn  Glu  Tyr  Asn  Gly  Val  Ser  Leu  Pro  Thr  Glu  Thr
                    885                 890                     895

Thr  Pro  Glu  Val  Thr  Arg  Ser  Pro  Ser  Pro  Cys  Lys  Ser  Pro  Asp  Thr
               900                 905                          910

Gln  Pro  Asp  Pro  Glu  Leu  Gly  Pro  Asp  Ser  Ser  Cys  Ser  Val  Pro  Thr
          915                      920                 925

Ala  Glu  Ser  Pro  Pro  Glu  Val  Val  Gly  Pro  Ser  Ser  Pro  Pro  Leu  Gln
          930                 935                      940

Thr  Ala  Ser  Leu  Ser  Ser  Gly  Gln  Leu  Pro  Pro  Leu  Leu  Thr  Pro  Thr
945                      950                 955                          960

Glu  Pro  Ser  Ser  Pro  Pro  Pro  Cys  Pro  Pro  Val  Leu  Thr  Val  Ala  Thr
               965                      970                     975

Pro  Pro  Pro  Pro  Leu  Leu  Pro  Thr  Val  Pro  Leu  Ser  His  Pro  Ser  Ser
               980                 985                          990

Asp  Ala  Ser  Pro  Gln  Gln  Cys  Pro  Ser  Pro  Phe  Ser  Asn  Thr  Thr  Ala
          995                      1000                1005

Gln  Ser  Pro  Leu  Pro  Ile  Leu  Ser  Pro  Thr  Val  Ser  Pro  Ser  Pro  Ser
     1010                1015                     1020

Pro  Ile  Pro  Pro  Val  Glu  Pro  Leu  Met  Ser  Ala  Ala  Ser  Pro  Gly  Pro
1025                     1030                1035                         1040

Pro  Thr  Leu  Ser  Ser  Ser  Ser  Ser  Ser  Ser  Ser  Ser  Phe  Pro  Ser  Ser
                    1045                1050                    1055

Ser  Cys  Ser  Ser  Thr  Ser  Pro  Ser  Pro  Pro  Leu  Ser  Ala  Val  Ser
               1060                1065                1070

Ser  Val  Val  Ser  Ser  Gly  Asp  Asn  Leu  Glu  Ala  Ser  Leu  Pro  Ala  Val
          1075                1080                    1085

Thr  Phe  Lys  Gln  Glu  Glu  Ser  Glu  Ser  Glu  Gly  Leu  Lys  Pro  Lys  Glu
          1090                1095                    1100

Glu  Ala  Pro  Pro  Ala  Gly  Gly  Gln  Ser  Val  Val  Gln  Glu  Thr  Phe  Ser
1105                     1110                1115                         1120

Lys  Asn  Phe  Ile  Cys  Asn  Val  Cys  Glu  Ser  Pro  Phe  Leu  Ser  Ile  Lys
                    1125                1130                    1135

Asp  Leu  Thr  Lys  His  Leu  Ser  Val  His  Ala  Glu  Glu  Trp  Pro  Phe  Lys
               1140                1145                    1150

Cys  Glu  Phe  Cys  Val  Gln  Leu  Phe  Lys  Val  Lys  Thr  Asp  Leu  Ser  Glu
```

|                                                              |
|--------------------------------------------------------------|
|                 1155                     1160                     1165 |

His Arg Phe Leu Leu His Gly Val Gly Asn Ile Phe Val Cys Ser Val
               1170                 1175                 1180

Cys Lys Lys Glu Phe Ala Phe Leu Cys Asn Leu Gln Gln His Gln Arg
1185                 1190                 1195                 1200

Asp Leu His Pro Asp Glu Val Cys Thr His His Glu Phe Glu Ser Gly
                 1205                 1210                 1215

Thr Leu Arg Pro Gln Asn Phe Thr Asp Pro Ser Lys Ala Asn Val Glu
                 1220                 1225                 1230

His Met Pro Ser Leu Pro Glu Glu Pro Leu Glu Thr Ser Arg Glu Glu
                 1235                 1240                 1245

Glu Leu Asn Asp Ser Ser Glu Glu Leu Tyr Thr Thr Ile Lys Ile Met
1250                 1255                 1260

Ala Ser Gly Ile Lys Thr Lys Asp Pro Asp Val Arg Leu Gly Leu Asn
1265                 1270                 1275                 1280

Gln His Tyr Pro Ser Phe Lys Pro Pro Pro Phe Gln Tyr His His Arg
                 1285                 1290                 1295

Asn Pro Met Gly Ile Gly Val Thr Ala Thr Asn Phe Thr Thr His Asn
                 1300                 1305                 1310

Ile Pro Gln Thr Phe Thr Thr Ala Ile Arg Cys Thr Lys Cys Gly Lys
                 1315                 1320                 1325

Gly Val Asp Asn Met Pro Glu Leu His Lys His Ile Leu Ala Cys Ala
                 1330                 1335                 1340

Ser Ala Ser Asp Lys Lys Arg Tyr Thr Pro Lys Lys Asn Pro Val Pro
1345                 1350                 1355                 1360

Leu Lys Gln Thr Val Gln Pro Lys Asn Gly Val Val Val Leu Asp Asn
                 1365                 1370                 1375

Ser Gly Lys Asn Ala Phe Arg Arg Met Gly Gln Pro Lys Arg Leu Ser
                 1380                 1385                 1390

Phe Asn Val Glu Leu Gly Lys Met Ser Pro Asn Lys Leu Lys Leu Ser
                 1395                 1400                 1405

Ala Leu Lys Lys Lys Asn Gln Leu Val Gln Lys Ala Ile Leu Gln Lys
                 1410                 1415                 1420

Asn Arg Ala Ala Lys Gln Lys Ala Asp Leu Arg Asp Thr Ser Glu Ala
1425                 1430                 1435                 1440

Ser Ser His Ile Cys Pro Tyr Cys Asp Arg Glu Phe Thr Tyr Ile Gly
                 1445                 1450                 1455

Ser Leu Asn Lys His Ala Ala Phe Ser Cys Pro Lys Lys Pro Leu Ser
                 1460                 1465                 1470

Pro Ser Lys Arg Lys Val Ser His Ser Ser Lys Lys Gly Gly His Ala
                 1475                 1480                 1485

Ser Ser Ser Ser Ser Asp Arg Asn Ser Ser Cys His Pro Arg Arg Arg
                 1490                 1495                 1500

Thr Ala Asp Thr Glu Ile Lys Met Gln Ser Thr Gln Ala Pro Leu Gly
1505                 1510                 1515                 1520

Lys Thr Arg Ala Arg Ser Thr Gly Pro Ala Gln Ala Ser Leu Pro Ser
                 1525                 1530                 1535

Ser Ser Phe Arg Ser Arg Gln Asn Val Lys Phe Ala Ala Ser Val Lys
                 1540                 1545                 1550

Ser Lys Lys Ala Ser Ser Ser Ser Leu Arg Asn Ser Ser Pro Ile Arg
                 1555                 1560                 1565

Met Ala Lys Ile Thr His Val Glu Gly Lys Lys Pro Lys Ala Val Ala
                 1570                 1575                 1580

| Lys | Ser | His | Ser | Ala | Gln | Leu | Ser | Ser | Lys | Ser | Ser | Arg | Gly | Leu | His |
|---|---|---|---|---|---|---|---|---|---|---|---|---|---|---|---|
| 1585 | | | | 1590 | | | | | 1595 | | | | | | 1600 |

| Val | Arg | Val | Gln | Lys | Ser | Lys | Ala | Val | Ile | Gln | Ser | Lys | Thr | Ala | Leu |
|---|---|---|---|---|---|---|---|---|---|---|---|---|---|---|---|
| | | | | 1605 | | | | | 1610 | | | | | 1615 | |

| Ala | Ser | Lys | Arg | Arg | Thr | Asp | Arg | Phe | Ile | Val | Lys | Ser | Arg | Glu | Arg |
|---|---|---|---|---|---|---|---|---|---|---|---|---|---|---|---|
| | | | 1620 | | | | | 1625 | | | | | 1630 | | |

| Ser | Gly | Gly | Pro | Ile | Thr | Arg | Ser | Leu | Gln | Leu | Ala | Ala | Ala | Ala | Asp |
|---|---|---|---|---|---|---|---|---|---|---|---|---|---|---|---|
| | | | 1635 | | | | | 1640 | | | | | 1645 | | |

| Leu | Ser | Glu | Ser | Arg | Arg | Glu | Asp | Ser | Ser | Ala | Arg | His | Glu | Leu | Lys |
|---|---|---|---|---|---|---|---|---|---|---|---|---|---|---|---|
| | 1650 | | | | | 1655 | | | | | 1660 | | | | |

| Asp | Phe | Ser | Tyr | Ser | Leu | Arg | Leu | Ala | Ser | Arg | Cys | Gly | Ser | Ser | Thr |
|---|---|---|---|---|---|---|---|---|---|---|---|---|---|---|---|
| 1665 | | | | | 1670 | | | | | 1675 | | | | | 1680 |

| Ala | Ser | Tyr | Ile | Thr | Arg | Gln | Cys | Arg | Lys | Val | Lys | Ala | Ala | Ala | Ala |
|---|---|---|---|---|---|---|---|---|---|---|---|---|---|---|---|
| | | | | 1685 | | | | | 1690 | | | | | 1695 | |

| Thr | Pro | Phe | Gln | Gly | Pro | Phe | Leu | Lys | Glu |
|---|---|---|---|---|---|---|---|---|---|
| | | | 1700 | | | | | 1705 | |

( 2 ) INFORMATION FOR SEQ ID NO:3:

( i ) SEQUENCE CHARACTERISTICS:
        ( A ) LENGTH: 5183 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..5158

( x i ) SEQUENCE DESCRIPTION: SEQ ID NO:3:

| ATG | AAT | CAG | AAC | ACT | ACT | GAG | CCT | GTG | GCG | GCC | ACC | GAG | ACC | CTG | GCT | 48 |
|---|---|---|---|---|---|---|---|---|---|---|---|---|---|---|---|---|
| Met | Asn | Gln | Asn | Thr | Thr | Glu | Pro | Val | Ala | Ala | Thr | Glu | Thr | Leu | Ala | |
| 1 | | | | 5 | | | | | 10 | | | | | 15 | | |

| GAG | GTA | CCC | GAA | CAT | GTG | CTG | CGA | GGA | CTT | CCG | GAG | GAA | GTG | AGG | CTT | 96 |
|---|---|---|---|---|---|---|---|---|---|---|---|---|---|---|---|---|
| Glu | Val | Pro | Glu | His | Val | Leu | Arg | Gly | Leu | Pro | Glu | Glu | Val | Arg | Leu | |
| | | | 20 | | | | | 25 | | | | | 30 | | | |

| TTC | CCT | TCT | GCT | GTT | GAC | AAG | ACC | CGG | ATT | GGT | GTC | TGG | GCC | ACT | AAA | 144 |
|---|---|---|---|---|---|---|---|---|---|---|---|---|---|---|---|---|
| Phe | Pro | Ser | Ala | Val | Asp | Lys | Thr | Arg | Ile | Gly | Val | Trp | Ala | Thr | Lys | |
| | | 35 | | | | | 40 | | | | | 45 | | | | |

| CCA | ATT | TTA | AAA | GGG | AAA | AAA | TTT | GGG | CCA | TTT | GTT | GGT | GAT | AAG | AAA | 192 |
|---|---|---|---|---|---|---|---|---|---|---|---|---|---|---|---|---|
| Pro | Ile | Leu | Lys | Gly | Lys | Lys | Phe | Gly | Pro | Phe | Val | Gly | Asp | Lys | Lys | |
| | 50 | | | | | 55 | | | | | 60 | | | | | |

| AAA | AGA | TCT | CAG | GTT | AAG | AAT | AAT | GTA | TAC | ATG | TGG | GAG | GTG | TAT | TAC | 240 |
|---|---|---|---|---|---|---|---|---|---|---|---|---|---|---|---|---|
| Lys | Arg | Ser | Gln | Val | Lys | Asn | Asn | Val | Tyr | Met | Trp | Glu | Val | Tyr | Tyr | |
| 65 | | | | | 70 | | | | | 75 | | | | | 80 | |

| CCA | AAT | TTG | GGA | TGG | ATG | TGC | ATT | GAT | GCC | ACT | GAT | CCA | GAG | AAG | GGA | 288 |
|---|---|---|---|---|---|---|---|---|---|---|---|---|---|---|---|---|
| Pro | Asn | Leu | Gly | Trp | Met | Cys | Ile | Asp | Ala | Thr | Asp | Pro | Glu | Lys | Gly | |
| | | | | 85 | | | | | 90 | | | | | 95 | | |

| AAC | TGG | CTG | CGA | TAT | GTG | AAT | TGG | GCT | TGC | TCA | GGA | GAA | GAG | CAA | AAT | 336 |
|---|---|---|---|---|---|---|---|---|---|---|---|---|---|---|---|---|
| Asn | Trp | Leu | Arg | Tyr | Val | Asn | Trp | Ala | Cys | Ser | Gly | Glu | Glu | Gln | Asn | |
| | | | 100 | | | | | 105 | | | | | 110 | | | |

| TTA | TTC | CCA | CTG | GAA | ATC | AAC | AGA | GCC | ATT | TAC | TAT | AAA | ACT | TTA | AAG | 384 |
|---|---|---|---|---|---|---|---|---|---|---|---|---|---|---|---|---|
| Leu | Phe | Pro | Leu | Glu | Ile | Asn | Arg | Ala | Ile | Tyr | Tyr | Lys | Thr | Leu | Lys | |
| | | 115 | | | | | 120 | | | | | 125 | | | | |

| CCA | ATC | GCG | CCG | GGC | GAG | GAG | CTC | CTG | GTC | TGG | TAC | AAT | GGG | GAA | GAC | 432 |
|---|---|---|---|---|---|---|---|---|---|---|---|---|---|---|---|---|
| Pro | Ile | Ala | Pro | Gly | Glu | Glu | Leu | Leu | Val | Trp | Tyr | Asn | Gly | Glu | Asp | |
| | 130 | | | | | 135 | | | | | 140 | | | | | |

| AAC | CCT | GAG | ATA | GCA | GCT | GCG | ATT | GAG | GAA | GAG | CGA | GCC | AGC | GCC | CGG | 480 |
|---|---|---|---|---|---|---|---|---|---|---|---|---|---|---|---|---|
| Asn | Pro | Glu | Ile | Ala | Ala | Ala | Ile | Glu | Glu | Glu | Arg | Ala | Ser | Ala | Arg | |
| 145 | | | | | 150 | | | | | 155 | | | | | 160 | |

| AGC | AAG | CGG | AGC | TCC | CCC | AAG | AGC | CGG | AAA | GGG | AAG | AAA | AAA | TCC | CAG | 528 |

| | | | | | | | | | | | | | | | | |
|---|---|---|---|---|---|---|---|---|---|---|---|---|---|---|---|---|
| Ser | Lys | Arg | Ser | Ser | Pro | Lys | Ser | Arg | Lys | Gly | Lys | Lys | Lys | Ser | Gln | |
| | | | | 165 | | | | 170 | | | | | 175 | | | |
| GAA | AAT | AAA | AAC | AAA | GGA | AAC | AAA | ATC | CAA | GAC | ATA | CAA | CTG | AAG | ACA | 576 |
| Glu | Asn | Lys | Asn | Lys | Gly | Asn | Lys | Ile | Gln | Asp | Ile | Gln | Leu | Lys | Thr | |
| | | | 180 | | | | | 185 | | | | | 190 | | | |
| AGT | GAG | CCA | GAT | TTC | ACC | TCT | GCA | AAT | ATG | AGA | GAT | TCT | GCA | GAA | GGT | 624 |
| Ser | Glu | Pro | Asp | Phe | Thr | Ser | Ala | Asn | Met | Arg | Asp | Ser | Ala | Glu | Gly | |
| | | 195 | | | | | 200 | | | | | 205 | | | | |
| CCT | AAA | GAA | GAC | GAA | GAG | AAG | CCT | TCA | GCC | TCA | GCA | CTT | GAG | CAG | CCG | 672 |
| Pro | Lys | Glu | Asp | Glu | Glu | Lys | Pro | Ser | Ala | Ser | Ala | Leu | Glu | Gln | Pro | |
| | 210 | | | | | 215 | | | | | 220 | | | | | |
| GCC | ACC | CTC | CAG | GAG | GTG | GCC | AGT | CAG | GAG | GTG | CCT | CCA | GAA | CTA | GCA | 720 |
| Ala | Thr | Leu | Gln | Glu | Val | Ala | Ser | Gln | Glu | Val | Pro | Pro | Glu | Leu | Ala | |
| 225 | | | | | 230 | | | | | 235 | | | | | 240 | |
| ACC | CCT | GCC | CCT | GCC | TGG | GAG | CCA | CAG | CCA | GAA | CCA | GAC | GAG | CGA | TTA | 768 |
| Thr | Pro | Ala | Pro | Ala | Trp | Glu | Pro | Gln | Pro | Glu | Pro | Asp | Glu | Arg | Leu | |
| | | | | 245 | | | | 250 | | | | | 255 | | | |
| GAA | GCG | GCA | GCT | TGT | GAG | GTG | AAT | GAT | TTG | GGG | GAA | GAG | GAG | GAG | GAG | 816 |
| Glu | Ala | Ala | Ala | Cys | Glu | Val | Asn | Asp | Leu | Gly | Glu | Glu | Glu | Glu | Glu | |
| | | | 260 | | | | | 265 | | | | | 270 | | | |
| GAA | GAG | GAG | GAG | GAT | GAA | GAA | GAA | GAA | GAA | GAT | GAT | GAT | GAT | GAT | GAG | 864 |
| Glu | Glu | Glu | Glu | Asp | Glu | Glu | Glu | Glu | Glu | Asp | Asp | Asp | Asp | Asp | Glu | |
| | | 275 | | | | | 280 | | | | | 285 | | | | |
| TTG | GAA | GAC | GAG | GGG | GAA | GAA | GAA | GCC | AGC | ATG | CCA | AAT | GAA | AAT | TCT | 912 |
| Leu | Glu | Asp | Glu | Gly | Glu | Glu | Glu | Ala | Ser | Met | Pro | Asn | Glu | Asn | Ser | |
| | 290 | | | | | 295 | | | | | 300 | | | | | |
| GTG | AAA | GAG | CCA | GAA | ATA | CGG | TGT | GAT | GAG | AAG | CCA | GAA | GAT | TTA | TTA | 960 |
| Val | Lys | Glu | Pro | Glu | Ile | Arg | Cys | Asp | Glu | Lys | Pro | Glu | Asp | Leu | Leu | |
| 305 | | | | | 310 | | | | | 315 | | | | | 320 | |
| GAG | GAA | CCA | AAA | ACA | ACT | TCA | GAA | GAA | ACT | CTT | GAA | GAC | TGC | TCA | GAG | 1008 |
| Glu | Glu | Pro | Lys | Thr | Thr | Ser | Glu | Glu | Thr | Leu | Glu | Asp | Cys | Ser | Glu | |
| | | | | 325 | | | | | 330 | | | | | 335 | | |
| GTA | ACA | CCT | GCC | ATG | CAA | ATC | CCC | AGA | ACT | AAA | GAA | GAG | GCC | AAT | GGT | 1056 |
| Val | Thr | Pro | Ala | Met | Gln | Ile | Pro | Arg | Thr | Lys | Glu | Glu | Ala | Asn | Gly | |
| | | | 340 | | | | | 345 | | | | | 350 | | | |
| GAT | GTA | TTT | GAA | ACG | TTT | ATG | TTT | CCG | TGT | CAA | CAT | TGT | GAA | AGG | AAG | 1104 |
| Asp | Val | Phe | Glu | Thr | Phe | Met | Phe | Pro | Cys | Gln | His | Cys | Glu | Arg | Lys | |
| | | 355 | | | | | 360 | | | | | 365 | | | | |
| TTT | ACA | ACC | AAA | CAG | GGG | CTT | GAG | CGT | CAC | ATG | CAT | ATC | CAT | ATA | TCC | 1152 |
| Phe | Thr | Thr | Lys | Gln | Gly | Leu | Glu | Arg | His | Met | His | Ile | His | Ile | Ser | |
| | 370 | | | | | 375 | | | | | 380 | | | | | |
| ACC | GTC | AAT | CAT | GCT | TTC | AAA | TGC | AAG | TAC | TGT | GGG | AAA | GCC | TTT | GGC | 1200 |
| Thr | Val | Asn | His | Ala | Phe | Lys | Cys | Lys | Tyr | Cys | Gly | Lys | Ala | Phe | Gly | |
| 385 | | | | | 390 | | | | | 395 | | | | | 400 | |
| ACA | CAG | ATT | AAC | CGG | CGG | CGA | CAT | GAG | CGG | CGC | CAT | GAA | GCA | GGG | TTA | 1248 |
| Thr | Gln | Ile | Asn | Arg | Arg | Arg | His | Glu | Arg | Arg | His | Glu | Ala | Gly | Leu | |
| | | | | 405 | | | | | 410 | | | | | 415 | | |
| AAG | CGG | AAA | CCC | AGC | CAA | ACA | CTA | CAG | CCG | TCA | GAG | GAT | CTG | GCT | GAT | 1296 |
| Lys | Arg | Lys | Pro | Ser | Gln | Thr | Leu | Gln | Pro | Ser | Glu | Asp | Leu | Ala | Asp | |
| | | | 420 | | | | | 425 | | | | | 430 | | | |
| GGC | AAA | GCA | TCT | GGA | GAA | AAC | GTT | GCT | TCA | AAA | GAT | GAT | TCG | AGT | CCT | 1344 |
| Gly | Lys | Ala | Ser | Gly | Glu | Asn | Val | Ala | Ser | Lys | Asp | Asp | Ser | Ser | Pro | |
| | | 435 | | | | | 440 | | | | | 445 | | | | |
| CCC | AGT | CTT | GGG | CCA | GAC | TGT | CTG | ATC | ATG | AAT | TCA | GAG | AAG | GCT | TCC | 1392 |
| Pro | Ser | Leu | Gly | Pro | Asp | Cys | Leu | Ile | Met | Asn | Ser | Glu | Lys | Ala | Ser | |
| | 450 | | | | | 455 | | | | | 460 | | | | | |
| CAA | GAC | ACA | ATA | AAT | TCT | TCT | GTC | GTA | GAA | GAG | AAT | GGG | GAA | GTT | AAA | 1440 |
| Gln | Asp | Thr | Ile | Asn | Ser | Ser | Val | Val | Glu | Glu | Asn | Gly | Glu | Val | Lys | |
| 465 | | | | | 470 | | | | | 475 | | | | | 480 | |
| GAA | CTT | CAT | CCG | TGC | AAA | TAT | TGT | AAA | AAG | GTT | TTT | GGA | ACT | CAT | ACT | 1488 |

| Glu | Leu | His | Pro | Cys 485 | Lys | Tyr | Cys | Lys 490 | Lys | Val | Phe | Gly | Thr | His 495 | Thr | | |
|---|---|---|---|---|---|---|---|---|---|---|---|---|---|---|---|---|---|

| AAT | ATG | AGA | CGG | CAT | CAG | CGT | AGA | GTT | CAC | GAA | CGT | CAT | CTG | ATT | CCC | 1536 |
|---|---|---|---|---|---|---|---|---|---|---|---|---|---|---|---|---|
| Asn | Met | Arg | Arg 500 | His | Gln | Arg | Arg 505 | Val | His | Glu | Arg | His 510 | Leu | Ile | Pro | |

| AAA | GGT | GTA | CGG | CGA | AAA | GGA | GGC | CTT | GAA | GAG | CCC | CAG | CCT | CCA | GCA | 1584 |
|---|---|---|---|---|---|---|---|---|---|---|---|---|---|---|---|---|
| Lys | Gly | Val 515 | Arg | Arg | Lys | Gly | Gly 520 | Leu | Glu | Glu | Pro | Gln 525 | Pro | Pro | Ala | |

| GAA | CAG | GCC | CAG | GCC | ACC | CAG | AAC | GTG | TAT | GTA | CCA | AGC | ACA | GAG | CCG | 1632 |
|---|---|---|---|---|---|---|---|---|---|---|---|---|---|---|---|---|
| Glu | Gln | Ala 530 | Gln | Ala | Thr | Gln | Asn 535 | Val | Tyr | Val | Pro | Ser 540 | Thr | Glu | Pro | |

| GAG | GAG | GAA | GGG | GAA | GCA | GAT | GAT | GTG | TAC | ATC | ATG | GAC | ATT | TCT | AGC | 1680 |
|---|---|---|---|---|---|---|---|---|---|---|---|---|---|---|---|---|
| Glu 545 | Glu | Glu | Gly | Glu | Ala 550 | Asp | Asp | Val | Tyr | Ile 555 | Met | Asp | Ile | Ser | Ser 560 | |

| AAT | ATC | TCT | GAA | AAC | TTA | AAT | TAC | TAT | ATT | GAT | GGT | AAA | ATT | CAA | ACT | 1728 |
|---|---|---|---|---|---|---|---|---|---|---|---|---|---|---|---|---|
| Asn | Ile | Ser | Glu | Asn 565 | Leu | Asn | Tyr | Tyr | Ile 570 | Asp | Gly | Lys | Ile | Gln 575 | Thr | |

| AAT | AAC | AAC | ACT | AGT | AAC | TGT | GAT | GTG | ATT | GAG | ATG | GAG | TCT | GCT | TCG | 1776 |
|---|---|---|---|---|---|---|---|---|---|---|---|---|---|---|---|---|
| Asn | Asn | Asn | Thr 580 | Ser | Asn | Cys | Asp | Val 585 | Ile | Glu | Met | Glu | Ser 590 | Ala | Ser | |

| GCA | GAT | TTG | TAT | GGT | ATA | AAT | TGT | CTG | CTC | ACT | CCA | GTT | ACA | GTG | GAA | 1824 |
|---|---|---|---|---|---|---|---|---|---|---|---|---|---|---|---|---|
| Ala | Asp | Leu | Tyr 595 | Gly | Ile | Asn | Cys 600 | Leu | Leu | Thr | Pro | Val 605 | Thr | Val | Glu | |

| ATT | ACT | CAA | AAT | ATA | AAG | ACC | ACA | CAG | GTC | CCT | GTA | ACA | GAA | GAT | CTT | 1872 |
|---|---|---|---|---|---|---|---|---|---|---|---|---|---|---|---|---|
| Ile | Thr 610 | Gln | Asn | Ile | Lys | Thr 615 | Thr | Gln | Val | Pro | Val 620 | Thr | Glu | Asp | Leu | |

| CCT | AAA | GAG | CCT | TTG | GGC | AGC | ACA | AAT | AGT | GAG | GCC | AAG | AAG | CGG | AGA | 1920 |
|---|---|---|---|---|---|---|---|---|---|---|---|---|---|---|---|---|
| Pro 625 | Lys | Glu | Pro | Leu | Gly 630 | Ser | Thr | Asn | Ser | Glu 635 | Ala | Lys | Lys | Arg | Arg 640 | |

| ACT | GCG | AGC | CCA | CCT | GCA | CTG | CCC | AAA | ATT | AAG | GCC | GAA | ACA | GAC | TCT | 1968 |
|---|---|---|---|---|---|---|---|---|---|---|---|---|---|---|---|---|
| Thr | Ala | Ser | Pro | Pro 645 | Ala | Leu | Pro | Lys | Ile 650 | Lys | Ala | Glu | Thr | Asp 655 | Ser | |

| GAC | CCC | ATG | GTC | CCC | TCT | TGC | TCT | TTA | AGT | CTT | CCT | CTT | AGC | ATA | TCA | 2016 |
|---|---|---|---|---|---|---|---|---|---|---|---|---|---|---|---|---|
| Asp | Pro | Met | Val 660 | Pro | Ser | Cys | Ser | Leu 665 | Ser | Leu | Pro | Leu | Ser 670 | Ile | Ser | |

| ACA | ACA | GAG | GCA | GTG | TCT | TTC | CAC | AAA | GAG | AAA | AGT | GTT | TAT | TTG | TCA | 2064 |
|---|---|---|---|---|---|---|---|---|---|---|---|---|---|---|---|---|
| Thr | Thr | Glu 675 | Ala | Val | Ser | Phe | His 680 | Lys | Glu | Lys | Ser | Val 685 | Tyr | Leu | Ser | |

| TCA | AAG | CTC | AAA | CAA | CTT | CTT | CAA | ACC | CAA | GAT | AAA | CTA | ACT | CCT | CCT | 2112 |
|---|---|---|---|---|---|---|---|---|---|---|---|---|---|---|---|---|
| Ser | Lys 690 | Leu | Lys | Gln | Leu | Leu 695 | Gln | Thr | Gln | Asp | Lys 700 | Leu | Thr | Pro | Pro | |

| GCA | GGG | ATT | TCA | GCA | ACT | GAA | ATA | GCT | AAA | TTA | GGT | CCT | GTT | TGT | GTG | 2160 |
|---|---|---|---|---|---|---|---|---|---|---|---|---|---|---|---|---|
| Ala 705 | Gly | Ile | Ser | Ala | Thr 710 | Glu | Ile | Ala | Lys | Leu 715 | Gly | Pro | Val | Cys | Val 720 | |

| TCT | GCT | CCT | GCA | TCA | ATG | TTG | CCT | GTG | ACC | TCA | AGT | AGG | TTT | AAG | AGG | 2208 |
|---|---|---|---|---|---|---|---|---|---|---|---|---|---|---|---|---|
| Ser | Ala | Pro | Ala | Ser 725 | Met | Leu | Pro | Val | Thr 730 | Ser | Ser | Arg | Phe | Lys 735 | Arg | |

| CGG | ACC | AGC | TCT | CCT | CCC | AGT | TCT | CCA | CAG | CAC | AGT | CCT | GCC | CTT | CGA | 2256 |
|---|---|---|---|---|---|---|---|---|---|---|---|---|---|---|---|---|
| Arg | Thr | Ser | Ser 740 | Pro | Pro | Ser | Ser | Pro 745 | Gln | His | Ser | Pro | Ala 750 | Leu | Arg | |

| GAC | TTT | GGA | AAG | CCA | AGT | GAT | GGG | AAA | GCA | GCA | TGG | ACC | GAT | GCC | GGG | 2304 |
|---|---|---|---|---|---|---|---|---|---|---|---|---|---|---|---|---|
| Asp | Phe | Gly | Lys 755 | Pro | Ser | Asp | Gly | Lys 760 | Ala | Ala | Trp | Thr | Asp 765 | Ala | Gly | |

| CTG | ACT | TCC | AAA | AAA | TCC | AAA | TTA | GAA | AGT | CAC | AGC | GAC | TCA | CCA | GCA | 2352 |
|---|---|---|---|---|---|---|---|---|---|---|---|---|---|---|---|---|
| Leu | Thr | Ser 770 | Lys | Lys | Ser | Lys | Leu 775 | Glu | Ser | His | Ser | Asp 780 | Ser | Pro | Ala | |

| TGG | AGT | TTG | TCT | GGG | AGA | GAT | GAG | AGA | GAA | ACT | GTG | AGC | CCT | CCA | TGC | 2400 |
|---|---|---|---|---|---|---|---|---|---|---|---|---|---|---|---|---|
| Trp 785 | Ser | Leu | Ser | Gly | Arg 790 | Asp | Glu | Arg | Glu | Thr 795 | Val | Ser | Pro | Pro | Cys 800 | |

| TTT | GAT | GAA | TAT | AAA | ATG | TCT | AAA | GAG | TGG | ACA | GCT | AGT | TCT | GCT | TTT | 2448 |
|---|---|---|---|---|---|---|---|---|---|---|---|---|---|---|---|---|

```
            Phe  Asp  Glu  Tyr  Lys  Met  Ser  Lys  Glu  Trp  Thr  Ala  Ser  Ser  Ala  Phe
                           805                 810                          815

AGC  AGT  GTG  TGC  AAC  CAG  CAG  CCA  CTG  GAT  TTA  TCC  AGC  GGT  GTC  AAA                    2496
Ser  Ser  Val  Cys  Asn  Gln  Gln  Pro  Leu  Asp  Leu  Ser  Ser  Gly  Val  Lys
               820                      825                          830

CAG  AAG  GCT  GAG  GGT  ACA  GGC  AAG  ACT  CCA  GTC  CAG  TGG  GAA  TCT  GTC                    2544
Gln  Lys  Ala  Glu  Gly  Thr  Gly  Lys  Thr  Pro  Val  Gln  Trp  Glu  Ser  Val
               835                      840                          845

TTA  GAT  CTC  AGT  GTG  CAT  AAA  AAG  CAT  TGT  AGT  GAC  TCT  GAA  GGC  AAG                    2592
Leu  Asp  Leu  Ser  Val  His  Lys  Lys  His  Cys  Ser  Asp  Ser  Glu  Gly  Lys
          850                      855                      860

GAA  TTC  AAA  GAA  AGT  CAT  TCA  GTG  CAG  CCT  ACG  TGT  AGT  GCT  GTA  AAG                    2640
Glu  Phe  Lys  Glu  Ser  His  Ser  Val  Gln  Pro  Thr  Cys  Ser  Ala  Val  Lys
865                      870                      875                          880

AAA  AGG  AAA  CCA  ACC  ACC  TGC  ATG  CTG  CAG  AAG  GTT  CTT  CTC  AAT  GAA                    2688
Lys  Arg  Lys  Pro  Thr  Thr  Cys  Met  Leu  Gln  Lys  Val  Leu  Leu  Asn  Glu
                         885                      890                          895

TAT  AAT  GGC  ATC  GAT  TTA  CCT  GTA  GAA  AAC  CCT  GCA  GAT  GGG  ACC  AGG                    2736
Tyr  Asn  Gly  Ile  Asp  Leu  Pro  Val  Glu  Asn  Pro  Ala  Asp  Gly  Thr  Arg
               900                      905                          910

AGC  CCA  AGT  CCT  TGT  AAA  TCC  CTA  GAA  GCT  CAG  CCA  GAT  CCT  GAC  CTC                    2784
Ser  Pro  Ser  Pro  Cys  Lys  Ser  Leu  Glu  Ala  Gln  Pro  Asp  Pro  Asp  Leu
               915                      920                          925

GGT  CCG  GGC  TCT  GGT  TTC  CCT  GCC  CCT  ACT  GTT  GAG  TCC  ACA  CCT  GAT                    2832
Gly  Pro  Gly  Ser  Gly  Phe  Pro  Ala  Pro  Thr  Val  Glu  Ser  Thr  Pro  Asp
          930                      935                      940

GTT  TGT  CCT  TCA  TCA  CCT  GCC  CTG  CAG  ACA  CCC  TCC  CTT  TCA  TCC  GGT                    2880
Val  Cys  Pro  Ser  Ser  Pro  Ala  Leu  Gln  Thr  Pro  Ser  Leu  Ser  Ser  Gly
945                      950                      955                          960

CAG  CTG  CCT  CCT  CTC  TTG  ATC  CCC  ACA  GAT  CCC  TCT  TCC  CCT  CCA  CCC                    2928
Gln  Leu  Pro  Pro  Leu  Leu  Ile  Pro  Thr  Asp  Pro  Ser  Ser  Pro  Pro  Pro
                    965                      970                          975

TGT  CCC  CCG  GTA  TTA  ACT  GTT  GCC  ACT  CCG  CCC  CCT  CCC  CTC  CTT  CCT                    2976
Cys  Pro  Pro  Val  Leu  Thr  Val  Ala  Thr  Pro  Pro  Pro  Pro  Leu  Leu  Pro
               980                      985                          990

ACC  GTA  CCT  CTT  CCA  GCC  CCC  TCT  TCC  AGT  GCA  TCT  CCA  CAC  CCA  TGC                    3024
Thr  Val  Pro  Leu  Pro  Ala  Pro  Ser  Ser  Ser  Ala  Ser  Pro  His  Pro  Cys
          995                      1000                     1005

CCC  TCT  CCA  CTC  TCA  AAT  GCC  ACC  GCA  CAG  TCC  CCA  CTT  CCA  ATT  CTG                    3072
Pro  Ser  Pro  Leu  Ser  Asn  Ala  Thr  Ala  Gln  Ser  Pro  Leu  Pro  Ile  Leu
     1010                     1015                     1020

TCC  CCA  ACA  GTG  TCC  CCC  TCT  CCC  TCT  CCC  ATT  CCT  CCC  GTG  GAG  CCC                    3120
Ser  Pro  Thr  Val  Ser  Pro  Ser  Pro  Ser  Pro  Ile  Pro  Pro  Val  Glu  Pro
1025                     1030                     1035                          1040

CTG  ATG  TCT  GCC  GCC  TCA  CCC  GGG  CCT  CCA  ACA  CTT  TCT  TCT  TCC  TCC                    3168
Leu  Met  Ser  Ala  Ala  Ser  Pro  Gly  Pro  Pro  Thr  Leu  Ser  Ser  Ser  Ser
                    1045                     1050                     1055

TCT  TCA  TCT  TCC  TCC  TCC  TCT  TCG  TTT  TCT  TCT  TCA  TCT  TCC  TCC  TCT                    3216
Ser  Ser  Ser  Ser  Ser  Ser  Ser  Ser  Phe  Ser  Ser  Ser  Ser  Ser  Ser  Ser
                    1060                     1065                     1070

TCT  CCT  TCT  CCA  CCT  CCT  CTC  TCC  GCA  ATA  TCA  TCT  GTT  GTT  TCC  TCT                    3264
Ser  Pro  Ser  Pro  Pro  Pro  Leu  Ser  Ala  Ile  Ser  Ser  Val  Val  Ser  Ser
               1075                     1080                     1085

GGT  GAT  AAT  CTG  GAG  GCT  TCT  CTC  CCC  ATG  ATA  TCT  TTC  AAA  CAG  GAG                    3312
Gly  Asp  Asn  Leu  Glu  Ala  Ser  Leu  Pro  Met  Ile  Ser  Phe  Lys  Gln  Glu
     1090                     1095                     1100

GAA  TTA  GAG  AAT  GAA  GGT  CTG  AAA  CCC  AGG  GAA  GAG  CCC  CAG  TCT  GCT                    3360
Glu  Leu  Glu  Asn  Glu  Gly  Leu  Lys  Pro  Arg  Glu  Glu  Pro  Gln  Ser  Ala
1105                     1110                     1115                          1120

GCT  GAA  CAG  GAT  GTT  GTT  GTT  CAG  GAA  ACA  TTC  AAC  AAA  AAC  TTT  GTT                    3408
```

```
Ala Glu Gln Asp Val Val Gln Glu Thr Phe Asn Lys Asn Phe Val
                1125                1130                1135

TGC AAC GTC TGT GAA TCA CCT TTT CTT TCC ATT AAA GAT CTA ACC AAA    3456
Cys Asn Val Cys Glu Ser Pro Phe Leu Ser Ile Lys Asp Leu Thr Lys
            1140                1145                1150

CAT TTA TCT ATT CAT GCT GAA GAA TGG CCC TTC AAA TGT GAA TTT TGT    3504
His Leu Ser Ile His Ala Glu Glu Trp Pro Phe Lys Cys Glu Phe Cys
        1155                1160                1165

GTG CAG CTT TTT AAG GAT AAA ACG GAC TTG TCA GAA CAT CGC TTT TTG    3552
Val Gln Leu Phe Lys Asp Lys Thr Asp Leu Ser Glu His Arg Phe Leu
    1170                1175                1180

CTT CAT GGA GTT GGG AAT ATC TTT GTG TGT TCT GTT TGT AAA AAA GAA    3600
Leu His Gly Val Gly Asn Ile Phe Val Cys Ser Val Cys Lys Lys Glu
1185                1190                1195                1200

TTT GCT TTT TTG TGC AAT TTG CAG CAG CAC CAG CGA GAT CTC CAC CCA    3648
Phe Ala Phe Leu Cys Asn Leu Gln Gln His Gln Arg Asp Leu His Pro
                1205                1210                1215

GAT AAG GTG TGC ACA CAT CAC GAG TTT GAA AGC GGG ACT CTG AGG CCC    3696
Asp Lys Val Cys Thr His His Glu Phe Glu Ser Gly Thr Leu Arg Pro
            1220                1225                1230

CAG AAC TTT ACA GAT CCC AGC AAG GCC CAT GTA GAG CAT ATG CAG AGC    3744
Gln Asn Phe Thr Asp Pro Ser Lys Ala His Val Glu His Met Gln Ser
        1235                1240                1245

TTG CCA GAA GAT CCT TTA GAA ACT TCT AAA GAA GAA GAG GAG TTA AAT    3792
Leu Pro Glu Asp Pro Leu Glu Thr Ser Lys Glu Glu Glu Glu Leu Asn
    1250                1255                1260

GAT TCC TCT GAA GAG CTT TAC ACG ACT ATA AAA ATA ATG GCT TCT GGA    3840
Asp Ser Ser Glu Glu Leu Tyr Thr Thr Ile Lys Ile Met Ala Ser Gly
1265                1270                1275                1280

ATA AAG ACA AAA GAT CCA GAT GTT CGA TTG GGC CTC AAT CAG CAT TAC    3888
Ile Lys Thr Lys Asp Pro Asp Val Arg Leu Gly Leu Asn Gln His Tyr
                1285                1290                1295

CCA AGC TTT AAA CCA CCT CCA TTT CAG TAC CAT CAC CGT AAC CCC ATG    3936
Pro Ser Phe Lys Pro Pro Pro Phe Gln Tyr His His Arg Asn Pro Met
            1300                1305                1310

GGG ATT GGT GTG ACA GCC ACA AAT TTC ACT ACA CAC AAT ATT CCA CAG    3984
Gly Ile Gly Val Thr Ala Thr Asn Phe Thr Thr His Asn Ile Pro Gln
        1315                1320                1325

ACT TTC ACT ACC GCC ATT CGC TGC ACA AAG TGT GGA AAA GGT GTC GAC    4032
Thr Phe Thr Thr Ala Ile Arg Cys Thr Lys Cys Gly Lys Gly Val Asp
    1330                1335                1340

AAT ATG CCG GAG TTG CAC AAA CAT ATC CTG GCT TGT GCT TCT GCA AGT    4080
Asn Met Pro Glu Leu His Lys His Ile Leu Ala Cys Ala Ser Ala Ser
1345                1350                1355                1360

GAC AAG AAG AGG TAC ACG CCT AAG AAA AAC CCA GTA CCA TTA AAA CAA    4128
Asp Lys Lys Arg Tyr Thr Pro Lys Lys Asn Pro Val Pro Leu Lys Gln
                1365                1370                1375

ACT GTG CAA CCC AAA AAT GGC GTG GTG GTT TTA GAT AAC TCT GGG AAA    4176
Thr Val Gln Pro Lys Asn Gly Val Val Val Leu Asp Asn Ser Gly Lys
            1380                1385                1390

AAT GCC TTC CGA CGA ATG GGA CAG CCC AAA AGG CTT AAC TTT AGT GTT    4224
Asn Ala Phe Arg Arg Met Gly Gln Pro Lys Arg Leu Asn Phe Ser Val
        1395                1400                1405

GAG CTC AGC AAA ATG TCG TCG AAT AAG CTC AAA TTA AAT GCA TTG AAG    4272
Glu Leu Ser Lys Met Ser Ser Asn Lys Leu Lys Leu Asn Ala Leu Lys
    1410                1415                1420

AAA AAA AAT CAG CTA GTA CAG AAA GCA ATT CTT CAG AAA AAC AAA TCT    4320
Lys Lys Asn Gln Leu Val Gln Lys Ala Ile Leu Gln Lys Asn Lys Ser
1425                1430                1435                1440

GCA AAG CAG AAG GCC GAC TTG AAA AAT GCT TGT GAG TCA TCC TCT CAC    4368
```

| | | | | | | | | | | | | | | | | |
|---|---|---|---|---|---|---|---|---|---|---|---|---|---|---|---|---|
| Ala | Lys | Gln | Lys | Ala | Asp | Leu | Lys | Asn | Ala | Cys | Glu | Ser | Ser | Ser | His | |
| | | | | 1445 | | | | 1450 | | | | | | 1455 | | |

| | | | | | | | | | | | | | | | | |
|---|---|---|---|---|---|---|---|---|---|---|---|---|---|---|---|---|
| ATC | TGC | CCT | TAC | TGT | AAT | CGA | GAG | TTC | ACT | TAC | ATT | GGA | AGC | CTG | AAT | 4416 |
| Ile | Cys | Pro | Tyr | Cys | Asn | Arg | Glu | Phe | Thr | Tyr | Ile | Gly | Ser | Leu | Asn | |
| | | | 1460 | | | | 1465 | | | | | 1470 | | | | |
| AAA | CAC | GCC | GCC | TTC | AGC | TGT | CCC | AAA | AAA | CCC | CTT | TCT | CCT | CCC | AAA | 4464 |
| Lys | His | Ala | Ala | Phe | Ser | Cys | Pro | Lys | Lys | Pro | Leu | Ser | Pro | Pro | Lys | |
| | | 1475 | | | | 1480 | | | | | 1485 | | | | | |
| AAA | AAA | GTT | TCT | CAT | TCA | TCT | AAG | AAA | GGT | GGA | CAC | TCA | TCA | CCT | GCA | 4512 |
| Lys | Lys | Val | Ser | His | Ser | Ser | Lys | Lys | Gly | Gly | His | Ser | Ser | Pro | Ala | |
| | 1490 | | | | 1495 | | | | | 1500 | | | | | | |
| AGT | AGT | GAC | AAA | AAC | AGT | AAC | AGC | AAC | CAC | CGC | AGA | CGG | ACA | GCG | GAT | 4560 |
| Ser | Ser | Asp | Lys | Asn | Ser | Asn | Ser | Asn | His | Arg | Arg | Arg | Thr | Ala | Asp | |
| 1505 | | | | | 1510 | | | | | 1515 | | | | | 1520 | |
| GCG | GAG | ATT | AAA | ATG | CAA | AGC | ATG | CAG | ACT | CCG | TTG | GGC | AAG | ACC | AGA | 4608 |
| Ala | Glu | Ile | Lys | Met | Gln | Ser | Met | Gln | Thr | Pro | Leu | Gly | Lys | Thr | Arg | |
| | | | | 1525 | | | | 1530 | | | | | 1535 | | | |
| GCC | CGC | AGC | TCA | GGC | CCC | ACC | CAA | GTC | CCA | CTT | CCC | TCC | TCA | TCC | TTC | 4656 |
| Ala | Arg | Ser | Ser | Gly | Pro | Thr | Gln | Val | Pro | Leu | Pro | Ser | Ser | Ser | Phe | |
| | | | 1540 | | | | 1545 | | | | | 1550 | | | | |
| AGG | TCC | AAG | CAG | AAC | GTC | AAG | TTT | GCA | GCT | TCG | GTG | AAA | TCC | AAA | AAA | 4704 |
| Arg | Ser | Lys | Gln | Asn | Val | Lys | Phe | Ala | Ala | Ser | Val | Lys | Ser | Lys | Lys | |
| | | 1555 | | | | 1560 | | | | | 1565 | | | | | |
| CCA | AGC | TCC | TCC | TCT | TTA | AGG | AAC | TCC | AGC | CCG | ATA | AGA | ATG | GCC | AAA | 4752 |
| Pro | Ser | Ser | Ser | Ser | Leu | Arg | Asn | Ser | Ser | Pro | Ile | Arg | Met | Ala | Lys | |
| 1570 | | | | | 1575 | | | | | 1580 | | | | | | |
| ATA | ACT | CAT | GTT | GAG | GGG | AAA | AAA | CCT | AAA | GCT | GTG | GCC | AAG | AAT | CAT | 4800 |
| Ile | Thr | His | Val | Glu | Gly | Lys | Lys | Pro | Lys | Ala | Val | Ala | Lys | Asn | His | |
| 1585 | | | | | 1590 | | | | | 1595 | | | | | 1600 | |
| TCT | GCT | CAG | CTT | TCC | AGC | AAA | ACA | TCG | CGG | AGC | CTG | CAC | GTG | AGG | GTA | 4848 |
| Ser | Ala | Gln | Leu | Ser | Ser | Lys | Thr | Ser | Arg | Ser | Leu | His | Val | Arg | Val | |
| | | | | 1605 | | | | 1610 | | | | | 1615 | | | |
| CAG | AAA | AGC | AAA | GCT | GTT | TTA | CAA | AGC | AAA | TCC | ACC | TTG | GCG | AGT | AAG | 4896 |
| Gln | Lys | Ser | Lys | Ala | Val | Leu | Gln | Ser | Lys | Ser | Thr | Leu | Ala | Ser | Lys | |
| | | | 1620 | | | | 1625 | | | | | 1630 | | | | |
| AAA | AGA | ACA | GAC | CGG | TTC | AAT | ATA | AAA | TCT | AGA | GAG | CGG | AGT | GGG | GGG | 4944 |
| Lys | Arg | Thr | Asp | Arg | Phe | Asn | Ile | Lys | Ser | Arg | Glu | Arg | Ser | Gly | Gly | |
| | | 1635 | | | | 1640 | | | | | 1645 | | | | | |
| CCA | GTC | ACC | CGG | AGC | CTT | CAG | CTG | GCA | GCT | GCT | GCT | GAC | TTG | AGT | GAG | 4992 |
| Pro | Val | Thr | Arg | Ser | Leu | Gln | Leu | Ala | Ala | Ala | Ala | Asp | Leu | Ser | Glu | |
| 1650 | | | | | 1655 | | | | | 1660 | | | | | | |
| AAC | AAG | AGA | GAG | GAC | GGC | AGC | GCC | AAG | CAG | GAG | CTG | AAG | GAC | TTC | AGC | 5040 |
| Asn | Lys | Arg | Glu | Asp | Gly | Ser | Ala | Lys | Gln | Glu | Leu | Lys | Asp | Phe | Ser | |
| 1665 | | | | | 1670 | | | | | 1675 | | | | | 1680 | |
| TAC | AGC | CTC | CGC | TTG | GCG | TCC | CGA | TGC | TCT | CCA | CCA | GCC | GCC | TCT | TAC | 5088 |
| Tyr | Ser | Leu | Arg | Leu | Ala | Ser | Arg | Cys | Ser | Pro | Pro | Ala | Ala | Ser | Tyr | |
| | | | | 1685 | | | | 1690 | | | | | 1695 | | | |
| ATC | ACC | AGG | CAG | TAT | AGG | AAG | GTC | AAA | GCT | CCG | GCT | GCA | GCC | CAG | TTC | 5136 |
| Ile | Thr | Arg | Gln | Tyr | Arg | Lys | Val | Lys | Ala | Pro | Ala | Ala | Ala | Gln | Phe | |
| | | | 1700 | | | | 1705 | | | | | 1710 | | | | |
| CAG | GGA | CCA | TTC | TTC | AAA | GAG | T AGACACTCTG GCTGCTCCCT GACAG | | | | | | | | | 5183 |
| Gln | Gly | Pro | Phe | Phe | Lys | Glu | | | | | | | | | | |
| | | 1715 | | | | | | | | | | | | | | |

( 2 ) INFORMATION FOR SEQ ID NO:4:

( i ) SEQUENCE CHARACTERISTICS:
        ( A ) LENGTH: 1719 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Asn | Gln | Asn | Thr | Thr | Glu | Pro | Val | Ala | Ala | Thr | Glu | Thr | Leu | Ala |
|---|---|---|---|---|---|---|---|---|---|---|---|---|---|---|---|
| 1 | | | | 5 | | | | | 10 | | | | | 15 | |

| Glu | Val | Pro | Glu | His | Val | Leu | Arg | Gly | Leu | Pro | Glu | Glu | Val | Arg | Leu |
|---|---|---|---|---|---|---|---|---|---|---|---|---|---|---|---|
| | | | 20 | | | | | 25 | | | | | 30 | | |

| Phe | Pro | Ser | Ala | Val | Asp | Lys | Thr | Arg | Ile | Gly | Val | Trp | Ala | Thr | Lys |
|---|---|---|---|---|---|---|---|---|---|---|---|---|---|---|---|
| | | | 35 | | | | | 40 | | | | | 45 | | |

| Pro | Ile | Leu | Lys | Gly | Lys | Lys | Phe | Gly | Pro | Phe | Val | Gly | Asp | Lys | Lys |
|---|---|---|---|---|---|---|---|---|---|---|---|---|---|---|---|
| | 50 | | | | | 55 | | | | | 60 | | | | |

| Lys | Arg | Ser | Gln | Val | Lys | Asn | Asn | Val | Tyr | Met | Trp | Glu | Val | Tyr | Tyr |
|---|---|---|---|---|---|---|---|---|---|---|---|---|---|---|---|
| 65 | | | | | 70 | | | | | 75 | | | | | 80 |

| Pro | Asn | Leu | Gly | Trp | Met | Cys | Ile | Asp | Ala | Thr | Asp | Pro | Glu | Lys | Gly |
|---|---|---|---|---|---|---|---|---|---|---|---|---|---|---|---|
| | | | | 85 | | | | | 90 | | | | | 95 | |

| Asn | Trp | Leu | Arg | Tyr | Val | Asn | Trp | Ala | Cys | Ser | Gly | Glu | Glu | Gln | Asn |
|---|---|---|---|---|---|---|---|---|---|---|---|---|---|---|---|
| | | | 100 | | | | | 105 | | | | | 110 | | |

| Leu | Phe | Pro | Leu | Glu | Ile | Asn | Arg | Ala | Ile | Tyr | Tyr | Lys | Thr | Leu | Lys |
|---|---|---|---|---|---|---|---|---|---|---|---|---|---|---|---|
| | | | 115 | | | | | 120 | | | | | 125 | | |

| Pro | Ile | Ala | Pro | Gly | Glu | Glu | Leu | Leu | Val | Trp | Tyr | Asn | Gly | Glu | Asp |
|---|---|---|---|---|---|---|---|---|---|---|---|---|---|---|---|
| | | 130 | | | | | 135 | | | | | 140 | | | |

| Asn | Pro | Glu | Ile | Ala | Ala | Ala | Ile | Glu | Glu | Glu | Arg | Ala | Ser | Ala | Arg |
|---|---|---|---|---|---|---|---|---|---|---|---|---|---|---|---|
| 145 | | | | | 150 | | | | | 155 | | | | | 160 |

| Ser | Lys | Arg | Ser | Ser | Pro | Lys | Ser | Arg | Lys | Gly | Lys | Lys | Lys | Ser | Gln |
|---|---|---|---|---|---|---|---|---|---|---|---|---|---|---|---|
| | | | | 165 | | | | | 170 | | | | | 175 | |

| Glu | Asn | Lys | Asn | Lys | Gly | Asn | Lys | Ile | Gln | Asp | Ile | Gln | Leu | Lys | Thr |
|---|---|---|---|---|---|---|---|---|---|---|---|---|---|---|---|
| | | | 180 | | | | | 185 | | | | | 190 | | |

| Ser | Glu | Pro | Asp | Phe | Thr | Ser | Ala | Asn | Met | Arg | Asp | Ser | Ala | Glu | Gly |
|---|---|---|---|---|---|---|---|---|---|---|---|---|---|---|---|
| | | 195 | | | | | 200 | | | | | 205 | | | |

| Pro | Lys | Glu | Asp | Glu | Glu | Lys | Pro | Ser | Ala | Ser | Ala | Leu | Glu | Gln | Pro |
|---|---|---|---|---|---|---|---|---|---|---|---|---|---|---|---|
| | 210 | | | | | 215 | | | | | 220 | | | | |

| Ala | Thr | Leu | Gln | Glu | Val | Ala | Ser | Gln | Glu | Val | Pro | Pro | Glu | Leu | Ala |
|---|---|---|---|---|---|---|---|---|---|---|---|---|---|---|---|
| 225 | | | | | 230 | | | | | 235 | | | | | 240 |

| Thr | Pro | Ala | Pro | Ala | Trp | Glu | Pro | Gln | Pro | Glu | Pro | Asp | Glu | Arg | Leu |
|---|---|---|---|---|---|---|---|---|---|---|---|---|---|---|---|
| | | | | 245 | | | | | 250 | | | | | 255 | |

| Glu | Ala | Ala | Ala | Cys | Glu | Val | Asn | Asp | Leu | Gly | Glu | Glu | Glu | Glu | Glu |
|---|---|---|---|---|---|---|---|---|---|---|---|---|---|---|---|
| | | | 260 | | | | | 265 | | | | | 270 | | |

| Glu | Glu | Glu | Glu | Asp | Glu | Glu | Glu | Glu | Glu | Asp | Asp | Asp | Asp | Asp | Glu |
|---|---|---|---|---|---|---|---|---|---|---|---|---|---|---|---|
| | | | 275 | | | | | 280 | | | | | 285 | | |

| Leu | Glu | Asp | Glu | Gly | Glu | Glu | Glu | Ala | Ser | Met | Pro | Asn | Glu | Asn | Ser |
|---|---|---|---|---|---|---|---|---|---|---|---|---|---|---|---|
| | 290 | | | | | 295 | | | | | 300 | | | | |

| Val | Lys | Glu | Pro | Glu | Ile | Arg | Cys | Asp | Glu | Lys | Pro | Glu | Asp | Leu | Leu |
|---|---|---|---|---|---|---|---|---|---|---|---|---|---|---|---|
| 305 | | | | | 310 | | | | | 315 | | | | | 320 |

| Glu | Glu | Pro | Lys | Thr | Thr | Ser | Glu | Glu | Thr | Leu | Glu | Asp | Cys | Ser | Glu |
|---|---|---|---|---|---|---|---|---|---|---|---|---|---|---|---|
| | | | | 325 | | | | | 330 | | | | | 335 | |

| Val | Thr | Pro | Ala | Met | Gln | Ile | Pro | Arg | Thr | Lys | Glu | Glu | Ala | Asn | Gly |
|---|---|---|---|---|---|---|---|---|---|---|---|---|---|---|---|
| | | | 340 | | | | | 345 | | | | | 350 | | |

| Asp | Val | Phe | Glu | Thr | Phe | Met | Phe | Pro | Cys | Gln | His | Cys | Glu | Arg | Lys |
|---|---|---|---|---|---|---|---|---|---|---|---|---|---|---|---|
| | | 355 | | | | | 360 | | | | | 365 | | | |

| Phe | Thr | Thr | Lys | Gln | Gly | Leu | Glu | Arg | His | Met | His | Ile | His | Ile | Ser |
|---|---|---|---|---|---|---|---|---|---|---|---|---|---|---|---|
| | 370 | | | | | 375 | | | | | 380 | | | | |

| Thr | Val | Asn | His | Ala | Phe | Lys | Cys | Lys | Tyr | Cys | Gly | Lys | Ala | Phe | Gly |
|---|---|---|---|---|---|---|---|---|---|---|---|---|---|---|---|
| 385 | | | | | 390 | | | | | 395 | | | | | 400 |

| Thr | Gln | Ile | Asn | Arg | Arg | Arg | His | Glu | Arg | Arg | His | Glu | Ala | Gly | Leu |
|---|---|---|---|---|---|---|---|---|---|---|---|---|---|---|---|
| | | | | 405 | | | | | 410 | | | | | 415 | |

```
Lys  Arg  Lys  Pro  Ser  Gln  Thr  Leu  Gln  Pro  Ser  Glu  Asp  Leu  Ala  Asp
               420                 425                      430

Gly  Lys  Ala  Ser  Gly  Glu  Asn  Val  Ala  Ser  Lys  Asp  Asp  Ser  Ser  Pro
               435                 440                      445

Pro  Ser  Leu  Gly  Pro  Asp  Cys  Leu  Ile  Met  Asn  Ser  Glu  Lys  Ala  Ser
               450                 455                      460

Gln  Asp  Thr  Ile  Asn  Ser  Val  Val  Glu  Glu  Asn  Gly  Glu  Val  Lys
465                           470                 475                      480

Glu  Leu  His  Pro  Cys  Lys  Tyr  Cys  Lys  Lys  Val  Phe  Gly  Thr  His  Thr
                    485                 490                      495

Asn  Met  Arg  Arg  His  Gln  Arg  Arg  Val  His  Glu  Arg  His  Leu  Ile  Pro
               500                 505                      510

Lys  Gly  Val  Arg  Arg  Lys  Gly  Gly  Leu  Glu  Glu  Pro  Gln  Pro  Pro  Ala
               515                 520                      525

Glu  Gln  Ala  Gln  Ala  Thr  Gln  Asn  Val  Tyr  Val  Pro  Ser  Thr  Glu  Pro
530                           535                      540

Glu  Glu  Glu  Gly  Glu  Ala  Asp  Asp  Val  Tyr  Ile  Met  Asp  Ile  Ser  Ser
545                      550                 555                           560

Asn  Ile  Ser  Glu  Asn  Leu  Asn  Tyr  Tyr  Ile  Asp  Gly  Lys  Ile  Gln  Thr
                    565                 570                      575

Asn  Asn  Asn  Thr  Ser  Asn  Cys  Asp  Val  Ile  Glu  Met  Glu  Ser  Ala  Ser
               580                 585                      590

Ala  Asp  Leu  Tyr  Gly  Ile  Asn  Cys  Leu  Leu  Thr  Pro  Val  Thr  Val  Glu
               595                 600                      605

Ile  Thr  Gln  Asn  Ile  Lys  Thr  Thr  Gln  Val  Pro  Val  Thr  Glu  Asp  Leu
          610                 615                 620

Pro  Lys  Glu  Pro  Leu  Gly  Ser  Thr  Asn  Ser  Glu  Ala  Lys  Lys  Arg  Arg
625                      630                 635                           640

Thr  Ala  Ser  Pro  Pro  Ala  Leu  Pro  Lys  Ile  Lys  Ala  Glu  Thr  Asp  Ser
                    645                 650                      655

Asp  Pro  Met  Val  Pro  Ser  Cys  Ser  Leu  Ser  Leu  Pro  Leu  Ser  Ile  Ser
               660                 665                      670

Thr  Thr  Glu  Ala  Val  Ser  Phe  His  Lys  Glu  Lys  Ser  Val  Tyr  Leu  Ser
          675                 680                 685

Ser  Lys  Leu  Lys  Gln  Leu  Leu  Gln  Thr  Gln  Asp  Lys  Leu  Thr  Pro  Pro
     690                      695                 700

Ala  Gly  Ile  Ser  Ala  Thr  Glu  Ile  Ala  Lys  Leu  Gly  Pro  Val  Cys  Val
705                      710                 715                           720

Ser  Ala  Pro  Ala  Ser  Met  Leu  Pro  Val  Thr  Ser  Ser  Arg  Phe  Lys  Arg
                    725                 730                      735

Arg  Thr  Ser  Ser  Pro  Pro  Ser  Ser  Pro  Gln  His  Ser  Pro  Ala  Leu  Arg
               740                 745                      750

Asp  Phe  Gly  Lys  Pro  Ser  Asp  Gly  Lys  Ala  Ala  Trp  Thr  Asp  Ala  Gly
          755                 760                      765

Leu  Thr  Ser  Lys  Lys  Ser  Lys  Leu  Glu  Ser  His  Ser  Asp  Ser  Pro  Ala
     770                      775                 780

Trp  Ser  Leu  Ser  Gly  Arg  Asp  Glu  Arg  Glu  Thr  Val  Ser  Pro  Pro  Cys
785                      790                 795                           800

Phe  Asp  Glu  Tyr  Lys  Met  Ser  Lys  Glu  Trp  Thr  Ala  Ser  Ser  Ala  Phe
                    805                 810                      815

Ser  Ser  Val  Cys  Asn  Gln  Gln  Pro  Leu  Asp  Leu  Ser  Ser  Gly  Val  Lys
               820                 825                      830

Gln  Lys  Ala  Glu  Gly  Thr  Gly  Lys  Thr  Pro  Val  Gln  Trp  Glu  Ser  Val
```

-continued

|     |     |     |     | 835 |     |     |     |     | 840 |     |     |     |     | 845 |
| --- | --- | --- | --- | --- | --- | --- | --- | --- | --- | --- | --- | --- | --- | --- |

Leu Asp Leu Ser Val His Lys Lys His Cys Ser Asp Ser Glu Gly Lys
850 855 860

Glu Phe Lys Glu Ser His Ser Val Gln Pro Thr Cys Ser Ala Val Lys
865 870 875 880

Lys Arg Lys Pro Thr Thr Cys Met Leu Gln Lys Val Leu Leu Asn Glu
885 890 895

Tyr Asn Gly Ile Asp Leu Pro Val Glu Asn Pro Ala Asp Gly Thr Arg
900 905 910

Ser Pro Ser Pro Cys Lys Ser Leu Glu Ala Gln Pro Asp Pro Asp Leu
915 920 925

Gly Pro Gly Ser Gly Phe Pro Ala Pro Thr Val Glu Ser Thr Pro Asp
930 935 940

Val Cys Pro Ser Ser Pro Ala Leu Gln Thr Pro Ser Leu Ser Ser Gly
945 950 955 960

Gln Leu Pro Pro Leu Leu Ile Pro Thr Asp Pro Ser Ser Pro Pro Pro
965 970 975

Cys Pro Pro Val Leu Thr Val Ala Thr Pro Pro Pro Leu Leu Pro
980 985 990

Thr Val Pro Leu Pro Ala Pro Ser Ser Ser Ala Ser Pro His Pro Cys
995 1000 1005

Pro Ser Pro Leu Ser Asn Ala Thr Ala Gln Ser Pro Leu Pro Ile Leu
1010 1015 1020

Ser Pro Thr Val Ser Pro Ser Pro Ser Pro Ile Pro Pro Val Glu Pro
1025 1030 1035 1040

Leu Met Ser Ala Ala Ser Pro Gly Pro Pro Thr Leu Ser Ser Ser Ser
1045 1050 1055

Ser Ser Ser Ser Ser Ser Ser Ser Phe Ser Ser Ser Ser Ser Ser
1060 1065 1070

Ser Pro Ser Pro Pro Pro Leu Ser Ala Ile Ser Ser Val Val Ser Ser
1075 1080 1085

Gly Asp Asn Leu Glu Ala Ser Leu Pro Met Ile Ser Phe Lys Gln Glu
1090 1095 1100

Glu Leu Glu Asn Glu Gly Leu Lys Pro Arg Glu Glu Pro Gln Ser Ala
1105 1110 1115 1120

Ala Glu Gln Asp Val Val Val Gln Glu Thr Phe Asn Lys Asn Phe Val
1125 1130 1135

Cys Asn Val Cys Glu Ser Pro Phe Leu Ser Ile Lys Asp Leu Thr Lys
1140 1145 1150

His Leu Ser Ile His Ala Glu Glu Trp Pro Phe Lys Cys Glu Phe Cys
1155 1160 1165

Val Gln Leu Phe Lys Asp Lys Thr Asp Leu Ser Glu His Arg Phe Leu
1170 1175 1180

Leu His Gly Val Gly Asn Ile Phe Val Cys Ser Val Cys Lys Lys Glu
1185 1190 1195 1200

Phe Ala Phe Leu Cys Asn Leu Gln Gln His Gln Arg Asp Leu His Pro
1205 1210 1215

Asp Lys Val Cys Thr His His Glu Phe Glu Ser Gly Thr Leu Arg Pro
1220 1225 1230

Gln Asn Phe Thr Asp Pro Ser Lys Ala His Val Glu His Met Gln Ser
1235 1240 1245

Leu Pro Glu Asp Pro Leu Glu Thr Ser Lys Glu Glu Glu Leu Asn
1250 1255 1260

```
Asp Ser Ser Glu Glu Leu Tyr Thr Thr Ile Lys Ile Met Ala Ser Gly
1265                1270                1275                1280

Ile Lys Thr Lys Asp Pro Asp Val Arg Leu Gly Leu Asn Gln His Tyr
                1285                1290                1295

Pro Ser Phe Lys Pro Pro Pro Phe Gln Tyr His His Arg Asn Pro Met
            1300                1305                1310

Gly Ile Gly Val Thr Ala Thr Asn Phe Thr Thr His Asn Ile Pro Gln
        1315                1320                1325

Thr Phe Thr Thr Ala Ile Arg Cys Thr Lys Cys Gly Lys Gly Val Asp
    1330                1335                1340

Asn Met Pro Glu Leu His Lys His Ile Leu Ala Cys Ala Ser Ala Ser
1345                1350                1355                1360

Asp Lys Lys Arg Tyr Thr Pro Lys Lys Asn Pro Val Pro Leu Lys Gln
                1365                1370                1375

Thr Val Gln Pro Lys Asn Gly Val Val Val Leu Asp Asn Ser Gly Lys
            1380                1385                1390

Asn Ala Phe Arg Arg Met Gly Gln Pro Lys Arg Leu Asn Phe Ser Val
        1395                1400                1405

Glu Leu Ser Lys Met Ser Ser Asn Lys Leu Lys Leu Asn Ala Leu Lys
    1410                1415                1420

Lys Lys Asn Gln Leu Val Gln Lys Ala Ile Leu Gln Lys Asn Lys Ser
1425                1430                1435                1440

Ala Lys Gln Lys Ala Asp Leu Lys Asn Ala Cys Glu Ser Ser Ser His
                1445                1450                1455

Ile Cys Pro Tyr Cys Asn Arg Glu Phe Thr Tyr Ile Gly Ser Leu Asn
            1460                1465                1470

Lys His Ala Ala Phe Ser Cys Pro Lys Lys Pro Leu Ser Pro Pro Lys
        1475                1480                1485

Lys Lys Val Ser His Ser Ser Lys Lys Gly Gly His Ser Ser Pro Ala
    1490                1495                1500

Ser Ser Asp Lys Asn Ser Asn Ser Asn His Arg Arg Arg Thr Ala Asp
1505                1510                1515                1520

Ala Glu Ile Lys Met Gln Ser Met Gln Thr Pro Leu Gly Lys Thr Arg
                1525                1530                1535

Ala Arg Ser Ser Gly Pro Thr Gln Val Pro Leu Pro Ser Ser Ser Phe
            1540                1545                1550

Arg Ser Lys Gln Asn Val Lys Phe Ala Ala Ser Val Lys Ser Lys Lys
        1555                1560                1565

Pro Ser Ser Ser Ser Leu Arg Asn Ser Ser Pro Ile Arg Met Ala Lys
    1570                1575                1580

Ile Thr His Val Glu Gly Lys Lys Pro Lys Ala Val Ala Lys Asn His
1585                1590                1595                1600

Ser Ala Gln Leu Ser Ser Lys Thr Ser Arg Ser Leu His Val Arg Val
                1605                1610                1615

Gln Lys Ser Lys Ala Val Leu Gln Ser Lys Ser Thr Leu Ala Ser Lys
            1620                1625                1630

Lys Arg Thr Asp Arg Phe Asn Ile Lys Ser Arg Glu Arg Ser Gly Gly
        1635                1640                1645

Pro Val Thr Arg Ser Leu Gln Leu Ala Ala Ala Ala Asp Leu Ser Glu
    1650                1655                1660

Asn Lys Arg Glu Asp Gly Ser Ala Lys Gln Glu Leu Lys Asp Phe Ser
1665                1670                1675                1680

Tyr Ser Leu Arg Leu Ala Ser Arg Cys Ser Pro Pro Ala Ala Ser Tyr
                1685                1690                1695
```

```
Ile  Thr  Arg  Gln  Tyr  Arg  Lys  Val  Lys  Ala  Pro  Ala  Ala  Ala  Gln  Phe
               1700                1705                1710

Gln  Gly  Pro  Phe  Phe  Lys  Glu
               1715
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:5:

```
Leu  Xaa  Cys  Xaa  Glu
 1                   5
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:6:

```
Glu  Ile  Arg  Cys  Glu  Glu  Lys  Pro  Glu  Asp  Leu
 1                   5                        10
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:7:

```
Lys  Pro  Glu  Asp  Leu  Leu  Glu  Glu  Pro  Gln  Ser
 1                   5                        10
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:8:

```
Glu  Glu  Glu  Glu  Tyr  Met  Pro  Met  Glu
 1                   5
```

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AATCGATGAA GAAGAAGAAT ATATGCCTAT GGAACA                                            36

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TTCCATAGGC ATATATTCTT CTTCTTCATC GATTTG  36

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CCGGAGATCC GGGCTGAAGA AAAGCCA  27

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TTCACACCGG ATCCCCGGCT CTTTCGC  27

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TGGCTCTTCT AATAAGTC  18

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( D ) TOPOLOGY: linear ( i x ) FEATURE:
        ( A ) NAME/KEY: Peptide
        ( B ) LOCATION: 15
        ( D ) OTHER INFORMATION: /note= "Xaa = (I/V)"

( x i ) SEQUENCE DESCRIPTION: SEQ ID NO:14:

Gly Xaa Xaa Xaa Xaa Gly Lys Xaa Xaa Xaa Xaa Xaa Xaa Xaa Xaa
1               5               10                          15

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TCTCCACAGC ACAGCCCT  18

( 2 ) INFORMATION FOR SEQ ID NO:16:

( i ) SEQUENCE CHARACTERISTICS:
        ( A ) LENGTH: 18 base pairs ( B ) TYPE: nucleic acid
        ( C ) STRANDEDNESS: single
        ( D ) TOPOLOGY: linear ( x i ) SEQUENCE DESCRIPTION: SEQ ID NO:16:

GGATAAGGAG GCTGTCTG                                                                                                 18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GTGGTCCAAG AAACATTC                                                                                                 18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCGTGTAAAG CTCTTCAG                                                                                                 18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GATACATTCC ACAGCCTG                                                                                                 18

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:20:

Glu  Asp  Leu  Leu  Glu  Glu
    1                   5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:21:

Glu  Asp  Leu  Leu  Asn  Glu
    1                   5

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
  ( A ) NAME/KEY: Peptide
  ( B ) LOCATION: 8
  ( D ) OTHER INFORMATION: /note= "Xaa = S or T"

( x i ) SEQUENCE DESCRIPTION: SEQ ID NO:22:

Gly Xaa Xaa Xaa Xaa Gly Lys Xaa
1                   5

( 2 ) INFORMATION FOR SEQ ID NO:23:

( i ) SEQUENCE CHARACTERISTICS:
    ( A ) LENGTH: 4 amino acids
    ( B ) TYPE: amino acid
    ( D ) TOPOLOGY: linear ( x i ) SEQUENCE DESCRIPTION: SEQ ID NO:23:

Asp Xaa Xaa Gly
1

( 2 ) INFORMATION FOR SEQ ID NO:24:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
  ( A ) NAME/KEY: Protein
  ( B ) LOCATION: 1
  ( D ) OTHER INFORMATION: /note= "Xaa = N or T"

( i x ) FEATURE:
  ( A ) NAME/KEY: Protein
  ( B ) LOCATION: 2
  ( D ) OTHER INFORMATION: /note= "Xaa = K or Q"

( x i ) SEQUENCE DESCRIPTION: SEQ ID NO:24:

Xaa Xaa Xaa Asp
1

( 2 ) INFORMATION FOR SEQ ID NO:25:

( i ) SEQUENCE CHARACTERISTICS:
    ( A ) LENGTH: 8 amino acids
    ( B ) TYPE: amino acid
    ( D ) TOPOLOGY: linear ( x i ) SEQUENCE DESCRIPTION: SEQ ID NO:25:

Gly Gly Thr Gly Thr Gly Ala Ala
1                   5

( 2 ) INFORMATION FOR SEQ ID NO:26:

( i ) SEQUENCE CHARACTERISTICS:
    ( A ) LENGTH: 6 amino acids
    ( B ) TYPE: amino acid
    ( D ) TOPOLOGY: linear ( x i ) SEQUENCE DESCRIPTION: SEQ ID NO:26:

Asp Leu Gly Ile Leu Thr
1                   5

( 2 ) INFORMATION FOR SEQ ID NO:27:

( i ) SEQUENCE CHARACTERISTICS:
    ( A ) LENGTH: 5 amino acids
    ( B ) TYPE: amino acid
    ( D ) TOPOLOGY: linear ( x i ) SEQUENCE DESCRIPTION: SEQ ID NO:27:

Asp Ser Leu Ile Thr
1                   5

( 2 ) INFORMATION FOR SEQ ID NO:28:

( i ) SEQUENCE CHARACTERISTICS:
    ( A ) LENGTH: 4 amino acids
    ( B ) TYPE: amino acid
    ( D ) TOPOLOGY: linear ( x i ) SEQUENCE DESCRIPTION: SEQ ID NO:28:

Asp Val Arg Thr
1

( 2 ) INFORMATION FOR SEQ ID NO:29:

( i ) SEQUENCE CHARACTERISTICS:
    ( A ) LENGTH: 4 amino acids
    ( B ) TYPE: amino acid
    ( D ) TOPOLOGY: linear ( x i ) SEQUENCE DESCRIPTION: SEQ ID NO:29:

Asp Ala Phe Gly
1

( 2 ) INFORMATION FOR SEQ ID NO:30:

( i ) SEQUENCE CHARACTERISTICS:
    ( A ) LENGTH: 4 amino acids
    ( B ) TYPE: amino acid
    ( D ) TOPOLOGY: linear ( x i ) SEQUENCE DESCRIPTION: SEQ ID NO:30:

Asp Leu Ser Gly
1

( 2 ) INFORMATION FOR SEQ ID NO:31:

( i ) SEQUENCE CHARACTERISTICS:
    ( A ) LENGTH: 4 amino acids
    ( B ) TYPE: amino acid
    ( D ) TOPOLOGY: linear ( x i ) SEQUENCE DESCRIPTION: SEQ ID NO:31:

Thr Ser Leu Asp
1

( 2 ) INFORMATION FOR SEQ ID NO:32:

( i ) SEQUENCE CHARACTERISTICS:
    ( A ) LENGTH: 8 amino acids
    ( B ) TYPE: amino acid
    ( D ) TOPOLOGY: linear ( x i ) SEQUENCE DESCRIPTION: SEQ ID NO:32:

Gly Asp Gly Ala Val Gly Lys Thr
1                   5

( 2 ) INFORMATION FOR SEQ ID NO:33:

( i ) SEQUENCE CHARACTERISTICS:
    ( A ) LENGTH: 4 amino acids
    ( B ) TYPE: amino acid
    ( D ) TOPOLOGY: linear ( x i ) SEQUENCE DESCRIPTION: SEQ ID NO:33:

Tyr Val Pro Thr
1

( 2 ) INFORMATION FOR SEQ ID NO:34:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:34:

Asp Thr Ala Gly
1

( 2 ) INFORMATION FOR SEQ ID NO:35:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:35:

Thr Gln Ile Asp
1

( 2 ) INFORMATION FOR SEQ ID NO:36:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:36:

Gly Val Asn Gly Val Gly Lys Ser
1                   5

( 2 ) INFORMATION FOR SEQ ID NO:37:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:37:

Thr Lys Phe Asp
1

( 2 ) INFORMATION FOR SEQ ID NO:38:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:38:

Gly His Val Asp His Gly Lys Thr
1                   5

( 2 ) INFORMATION FOR SEQ ID NO:39:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:39:

Asp Xaa Xaa Xaa Xaa Xaa Xaa Xaa Xaa Xaa Xaa Thr (2) INFORMATION FOR SEQ ID NO:40:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:40:

```
Asp Cys Pro Gly
1
```

(2) INFORMATION FOR SEQ ID NO:41:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:41:

```
Asn Lys Cys Asp
1
```

(2) INFORMATION FOR SEQ ID NO:42:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:42:

```
Gly Ala Gly Gly Val Gly Lys Ser
1               5
```

(2) INFORMATION FOR SEQ ID NO:43:

(i) SEQUENCE CHARACTERISTICS:
        (A) LENGTH: 3 amino acids
        (B) TYPE: amino acid
        (D) TOPOLOGY: linear (xi) SEQUENCE DESCRIPTION: SEQ ID NO:43:

```
Asp Pro Thr
1
```

(2) INFORMATION FOR SEQ ID NO:44:

(i) SEQUENCE CHARACTERISTICS:
        (A) LENGTH: 29 amino acids
        (B) TYPE: amino acid
        (D) TOPOLOGY: linear (xi) SEQUENCE DESCRIPTION: SEQ ID NO:44:

```
Thr Ala Pro Glu Asp Pro Asn Glu Glu Ala Val Ser Gln Ile Phe Pro
1               5                   10                  15
Asp Ser Val Met Leu Ala Val Gln Glu Gly Ile Asp Leu
            20                  25
```

(2) INFORMATION FOR SEQ ID NO:45:

(i) SEQUENCE CHARACTERISTICS:
        (A) LENGTH: 29 amino acids
        (B) TYPE: amino acid
        (D) TOPOLOGY: linear (xi) SEQUENCE DESCRIPTION: SEQ ID NO:45:

Thr Ala Pro Glu Asp Pro Asn Glu Glu Ala Val Ser Gln Ile Phe Pro
1               5                   10                  15

Asp Ser Val Met Leu Ala Val Gln Glu Gly Ile Asp Leu
                20                  25

(2) INFORMATION FOR SEQ ID NO:46:

(i) SEQUENCE CHARACTERISTICS:
        (A) LENGTH: 29 amino acids
        (B) TYPE: amino acid
        (D) TOPOLOGY: linear (xi) SEQUENCE DESCRIPTION: SEQ ID NO:46:

Asp Gly Pro Glu Asp Pro Asn Glu Gly Ala Val Asn Gly Phe Phe Thr
1               5                   10                  15

Asp Ser Met Leu Leu Ala Ala Asp Glu Gly Leu Asp Ile
                20                  25

(2) INFORMATION FOR SEQ ID NO:47:

(i) SEQUENCE CHARACTERISTICS:
        (A) LENGTH: 29 amino acids
        (B) TYPE: amino acid
        (D) TOPOLOGY: linear (xi) SEQUENCE DESCRIPTION: SEQ ID NO:47:

Ser Ala Gly Glu Asp Asn Asn Glu Gln Ala Val Asn Glu Phe Phe Pro
1               5                   10                  15

Glu Ser Leu Ile Leu Ala Ala Ser Glu Gly Leu Phe Leu
                20                  25

(2) INFORMATION FOR SEQ ID NO:48:

(i) SEQUENCE CHARACTERISTICS:
        (A) LENGTH: 29 amino acids
        (B) TYPE: amino acid
        (D) TOPOLOGY: linear (xi) SEQUENCE DESCRIPTION: SEQ ID NO:48:

Thr Gly Gln Glu Asp Glu Asn Glu Glu Ala Val Asp Gly Val Phe Ser
1               5                   10                  15

Asp Ala Met Leu Leu Ala Ala Glu Glu Gly Ile Glu Met
                20                  25

(2) INFORMATION FOR SEQ ID NO:49:

(i) SEQUENCE CHARACTERISTICS:
        (A) LENGTH: 30 amino acids
        (B) TYPE: amino acid
        (D) TOPOLOGY: linear (xi) SEQUENCE DESCRIPTION: SEQ ID NO:49:

Asp Gly Phe Glu Glu Asp Ala Asn Gln Glu Ala Val Asp Gly Met Phe
1               5                   10                  15

Pro Glu Arg Leu Leu Ser Glu Ala Glu Ser Ala Ala Glu Ser
                20                  25                  30

(2) INFORMATION FOR SEQ ID NO:50:

(i) SEQUENCE CHARACTERISTICS:
        (A) LENGTH: 50 amino acids
        (B) TYPE: amino acid
        (D) TOPOLOGY: linear (xi) SEQUENCE DESCRIPTION: SEQ ID NO:50:

```
Ala Lys Tyr Asp Phe Lys Ala Thr Ala Asp Asp Glu Leu Ser Phe Lys
1               5                       10                      15

Arg Gly Asp Ile Leu Lys Tyr Leu Asn Glu Glu Cys Asp Gln Asn Trp
                20              25                      30

Tyr Lys Ala Glu Leu Asn Gly Lys Asp Gly Phe Ile Pro Lys Asn Tyr
        35                      40                  45

Ile Glu
    50
```

( 2 ) INFORMATION FOR SEQ ID NO:51:

( i ) SEQUENCE CHARACTERISTICS:
        ( A ) LENGTH: 49 amino acids
        ( B ) TYPE: amino acid
        ( D ) TOPOLOGY: linear ( x i ) SEQUENCE DESCRIPTION: SEQ ID NO:51:

```
Ala Leu Phe Asp Phe Asp Pro Gln Glu Asp Gly Glu Leu Gly Phe Arg
1               5                       10                      15

Arg Gly Asp Phe Ile His Val Met Asp Asn Ser Asp Pro Asn Trp Trp
                20              25                      30

Lys Gly Ala Cys His Gly Gln Thr Gly Met Phe Pro Arg Asn Tyr Val
        35                      40                  45

Thr
```

( 2 ) INFORMATION FOR SEQ ID NO:52:

( i ) SEQUENCE CHARACTERISTICS:
        ( A ) LENGTH: 66 amino acids
        ( B ) TYPE: amino acid
        ( D ) TOPOLOGY: linear ( x i ) SEQUENCE DESCRIPTION: SEQ ID NO:52:

```
Ala Leu Tyr Asp Tyr Lys Lys Glu Arg Glu Glu Asp Ile Asp Leu His
1               5                       10                      15

Leu Gly Asp Ile Leu Thr Val Asn Lys Gly Ser Leu Val Ala Leu Gly
                20              25                      30

Phe Ser Asp Gly Gln Glu Ala Arg Pro Glu Glu Ile Gly Trp Leu Asn
        35                      40                  45

Gly Tyr Asn Glu Thr Thr Gly Glu Arg Gly Asp Phe Pro Gly Thr Tyr
        50                      55                  60

Val Glu
65
```

( 2 ) INFORMATION FOR SEQ ID NO:53:

( i ) SEQUENCE CHARACTERISTICS:
        ( A ) LENGTH: 49 amino acids
        ( B ) TYPE: amino acid
        ( D ) TOPOLOGY: linear ( x i ) SEQUENCE DESCRIPTION: SEQ ID NO:53:

```
Ala Leu Tyr Asp Phe Val Ala Ser Gly Asp Asn Thr Leu Ser Ile Thr
1               5                       10                      15

Lys Gly Glu Lys Leu Arg Val Leu Tyr Asn His Asn Gly Glu Trp Cys
                20              25                      30

Glu Ala Gln Thr Lys Asn Gly Gln Gly Trp Val Pro Ser Asn Tyr Ile
        35                      40                  45

Thr
```

( 2 ) INFORMATION FOR SEQ ID NO:54:

( i ) SEQUENCE CHARACTERISTICS:
        ( A ) LENGTH: 51 amino acids
        ( B ) TYPE: amino acid
        ( D ) TOPOLOGY: linear ( x i ) SEQUENCE DESCRIPTION: SEQ ID NO:54:

```
Ala  Leu  Tyr  Asp  Tyr  Glu  Ser  Arg  Thr  Glu  Thr  Asp  Leu  Ala  Phe  Lys
1                   5                        10                       15

Lys  Gly  Glu  Arg  Leu  Gln  Ile  Val  Met  Asn  Thr  Glu  Gly  Asp  Trp  Trp
               20                       25                       30

Leu  Ala  His  Ser  Leu  Thr  Thr  Gly  Gln  Thr  Gly  Tyr  Ile  Pro  Ser  Asn
               35                       40                       45

Tyr  Val  Ala
          50
```

( 2 ) INFORMATION FOR SEQ ID NO:55:

( i ) SEQUENCE CHARACTERISTICS:
        ( A ) LENGTH: 52 amino acids
        ( B ) TYPE: amino acid
        ( D ) TOPOLOGY: linear ( x i ) SEQUENCE DESCRIPTION: SEQ ID NO:55:

```
Ala  Ile  Leu  Pro  Tyr  Thr  Lys  Val  Pro  Asp  Thr  Asp  Glu  Ile  Ser  Phe
1                   5                        10                       15

Leu  Lys  Gly  Asp  Met  Phe  Ile  Val  His  Asn  Glu  Leu  Glu  Asp  Gly  Trp
               20                       25                       30

Met  Trp  Val  Thr  Asn  Leu  Arg  Thr  Asp  Glu  Gln  Gly  Leu  Ile  Val  Glu
               35                       40                       45

Asp  Leu  Val  Glu
          50
```

( 2 ) INFORMATION FOR SEQ ID NO:56:

( i ) SEQUENCE CHARACTERISTICS:
        ( A ) LENGTH: 50 amino acids
        ( B ) TYPE: amino acid
        ( D ) TOPOLOGY: linear ( x i ) SEQUENCE DESCRIPTION: SEQ ID NO:56:

```
Ala  Leu  Phe  Asp  Tyr  Lys  Ala  Gln  Arg  Glu  Asp  Glu  Leu  Thr  Phe  Thr
1                   5                        10                       15

Lys  Ser  Ala  Ile  Ile  Gln  Asn  Val  Glu  Lys  Gln  Glu  Gly  Gly  Trp  Trp
               20                       25                       30

Arg  Gly  Asp  Tyr  Gly  Gly  Lys  Lys  Gln  Leu  Trp  Phe  Pro  Ser  Asn  Tyr
               35                       40                       45

Val  Glu
     50
```

( 2 ) INFORMATION FOR SEQ ID NO:57:

( i ) SEQUENCE CHARACTERISTICS:
        ( A ) LENGTH: 50 amino acids
        ( B ) TYPE: amino acid
        ( D ) TOPOLOGY: linear ( x i ) SEQUENCE DESCRIPTION: SEQ ID NO:57:

```
Ala  Leu  Phe  Asp  Phe  Lys  Gly  Asn  Asp  Asp  Glu  Asp  Leu  Pro  Phe  Lys
1                   5                        10                       15

Lys  Gly  Asp  Ile  Leu  Lys  Ile  Arg  Asp  Lys  Pro  Glu  Glu  Gln  Trp  Trp
               20                       25                       30
```

```
        Asn  Ala  Glu  Asp  Met  Asp  Gly  Lys  Arg  Gly  Met  Ile  Pro  Val  Pro  Tyr
                  35                      40                      45

Val  Glu
             50
```

( 2 ) INFORMATION FOR SEQ ID NO:58:

( i ) SEQUENCE CHARACTERISTICS:
        ( A ) LENGTH: 28 amino acids
        ( B ) TYPE: amino acid
        ( D ) TOPOLOGY: linear ( x i ) SEQUENCE DESCRIPTION: SEQ ID NO:58:

```
        Ala  Pro  Pro  Thr  Pro  Pro  Pro  Leu  Pro  Pro  Pro  Leu  Ile  Pro  Pro  Pro
        1              5                        10                      15

Pro  Pro  Leu  Pro  Pro  Gly  Leu  Gly  Pro  Leu  Pro  Pro
                       20                 25
```

( 2 ) INFORMATION FOR SEQ ID NO:59:

( i ) SEQUENCE CHARACTERISTICS:
        ( A ) LENGTH: 21 amino acids
        ( B ) TYPE: amino acid
        ( D ) TOPOLOGY: linear ( x i ) SEQUENCE DESCRIPTION: SEQ ID NO:59:

```
        Ala  Pro  Thr  Met  Pro  Pro  Pro  Leu  Pro  Pro  Val  Pro  Pro  Gln  Pro  Ala
        1              5                        10                      15

Arg  Arg  Gln  Ser  Arg
                       20
```

( 2 ) INFORMATION FOR SEQ ID NO:60:

( i ) SEQUENCE CHARACTERISTICS:
        ( A ) LENGTH: 40 amino acids
        ( B ) TYPE: amino acid
        ( D ) TOPOLOGY: linear ( x i ) SEQUENCE DESCRIPTION: SEQ ID NO:60:

```
        Pro  Pro  Ala  Tyr  Pro  Pro  Pro  Val  Pro  Val  Pro  Arg  Lys  Pro  Ala
        1              5                        10                      15

Phe  Ser  Asp  Leu  Pro  Arg  Ala  His  Ser  Phe  Thr  Ser  Lys  Ser  Pro  Ser
                       20                      25                      30

Pro  Leu  Leu  Pro  Pro  Pro  Pro  Pro
                       35                 40
```

( 2 ) INFORMATION FOR SEQ ID NO:61:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:61:

```
        Pro  Pro  Ala  Leu  Pro  Pro  Pro  Pro  Arg  Pro  Val  Pro
        1              5                        10
```

( 2 ) INFORMATION FOR SEQ ID NO:62:

( i ) SEQUENCE CHARACTERISTICS:
        ( A ) LENGTH: 84 amino acids
        ( B ) TYPE: amino acid
        ( D ) TOPOLOGY: linear ( x i ) SEQUENCE DESCRIPTION: SEQ ID NO:62:

```
            Cys   Asn  Val   Cys  Ala   Lys  Thr   Phe  Gly   Gln  Leu   Ser  Asn   Leu  Lys   Val
            1                     5                       10                         15

His   Leu  Arg   Val  His   Ser  Gly   Glu  Arg   Pro  Phe   Lys  Cys   Gln  Thr   Cys
                              20                    25                         30

Asn   Lys  Gly   Phe  Thr   Gln  Leu   Ala  His   Leu  Gln   Lys  His   Tyr  Leu   Val
                        35                          40                         45

His   Thr  Gly   Glu  Lys   Pro  His   Glu  Cys   Gln  Val   Cys  His   Lys  Arg   Phe
                  50                           55                    60

Ser   Ser  Thr   Ser  Asn   Leu  Lys   Thr  His   Leu  Arg   Leu  His   Ser  Gly   Glu
            65                          70                          75                          80

Lys   Pro  Tyr   Gln
```

( 2 ) INFORMATION FOR SEQ ID NO:63:

( i ) SEQUENCE CHARACTERISTICS:
        ( A ) LENGTH: 80 amino acids
        ( B ) TYPE: amino acid
        ( D ) TOPOLOGY: linear ( x i ) SEQUENCE DESCRIPTION: SEQ ID NO:63:

```
            Glu   Val  Ile   Gly  Val   Met  Ser   Lys  Glu   Tyr  Ile   Pro  Lys   Gly  Thr   Arg
            1                     5                       10                         15

Phe   Gly  Pro   Leu  Ile   Gly  Glu   Ile  Tyr   Thr  Asn   Asp  Thr   Val  Pro   Lys
                              20                    25                         30

Asn   Ala  Asn   Arg  Lys   Tyr  Phe   Trp  Arg   Ile  Tyr   Ser  Arg   Gly  Glu   Leu
                        35                          40                         45

His   His  Phe   Ile  Asp   Gly  Phe   Asn  Glu   Glu  Lys   Ser  Asn   Trp  Met   Arg
                  50                           55                    60

Tyr   Val  Asn   Pro  Ala   His  Ser   Pro  Arg   Glu  Gln   Asn  Leu   Ala  Ala   Cys
            65                          70                          75                          80
```

( 2 ) INFORMATION FOR SEQ ID NO:64:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO:64:

```
            Gln   Asn  Gly   Met  Asn   Ile  Tyr   Phe  Tyr   Thr  Ile   Lys  Pro   Ile  Pro   Ala
            1                     5                       10                         15

Asn   Gln  Glu   Leu  Leu   Val  Trp   Tyr  Cys   Arg  Asp   Phe  Ala   Glu
                              20                    25                         30
```

( 2 ) INFORMATION FOR SEQ ID NO:65:

( i ) SEQUENCE CHARACTERISTICS:
        ( A ) LENGTH: 23 amino acids
        ( B ) TYPE: amino acid
        ( D ) TOPOLOGY: linear ( x i ) SEQUENCE DESCRIPTION: SEQ ID NO:65:

```
            Val   Glu  Glu   Ala  Asp   Met  Pro   Asn  Glu   Ser  Ser   Ala  Lys   Glu  Pro   Glu
            1                     5                       10                         15

Ile   Arg  Cys   Glu  Glu   Lys  Pro
                              20
```

( 2 ) INFORMATION FOR SEQ ID NO:66:

( i ) SEQUENCE CHARACTERISTICS:
        ( A ) LENGTH: 22 amino acids ( B ) TYPE: amino acid
( D ) TOPOLOGY: linear ( x i ) SEQUENCE DESCRIPTION: SEQ ID NO:66:

```
Leu Gly Pro Val Ser Met Pro Asn Leu Val Pro Glu Val Ile Asp Leu
1               5                   10                  15
Thr Cys His Glu Ala Gly
            20
```

( 2 ) INFORMATION FOR SEQ ID NO:67:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:67:

```
Leu Gly Pro Val Ser Met Pro Asn Leu Val Pro Glu Val Ile Asp Leu
1               5                   10                  15
Thr Cys His Glu Ala Gly
            20
```

( 2 ) INFORMATION FOR SEQ ID NO:68:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO:68:

```
Leu Gly Ala Ala Glu Met Asp Leu Arg Cys Tyr Glu Glu Gly
1               5                   10
```

( 2 ) INFORMATION FOR SEQ ID NO:69:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO:69:

```
Leu His Pro Glu Asp Met Asp Leu Leu Cys Tyr Glu Met Gly
1               5                   10
```

( 2 ) INFORMATION FOR SEQ ID NO:70:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:70:

```
Val Gly Gly Gly Glu Met Pro Glu Leu Gln Pro Glu Glu Glu Asp Leu
1               5                   10                  15
Phe Cys Tyr Glu Asp Gly
            20
```

( 2 ) INFORMATION FOR SEQ ID NO:71:

( i ) SEQUENCE CHARACTERISTICS:
( A ) LENGTH: 18 amino acids
( B ) TYPE: amino acid
( D ) TOPOLOGY: linear ( x i ) SEQUENCE DESCRIPTION: SEQ ID NO:71:

```
Val Gly Glu Glu Leu Leu Pro Val Asp Leu Asp Leu Lys Cys Tyr Glu
```

```
            1               5                        10                       15
```

Asp Gly (2) INFORMATION FOR SEQ ID NO:72:

(i) SEQUENCE CHARACTERISTICS:
        (A) LENGTH: 9 amino acids
        (B) TYPE: amino acid
        (D) TOPOLOGY: linear (x i) SEQUENCE DESCRIPTION: SEQ ID NO:72:

```
Glu Asp Leu Leu Glu Glu Pro Gln Ser
 1               5
```

(2) INFORMATION FOR SEQ ID NO:73:

(i) SEQUENCE CHARACTERISTICS:
        (A) LENGTH: 10 amino acids
        (B) TYPE: amino acid
        (D) TOPOLOGY: linear (x i) SEQUENCE DESCRIPTION: SEQ ID NO:73:

```
Glu Asp Leu Leu Asn Glu Ser Gly Gln Pro
 1               5                   10
```

(2) INFORMATION FOR SEQ ID NO:74:

(i) SEQUENCE CHARACTERISTICS:
        (A) LENGTH: 9 amino acids
        (B) TYPE: amino acid
        (D) TOPOLOGY: linear (x i) SEQUENCE DESCRIPTION: SEQ ID NO:74:

```
Glu Asp Leu Leu Asn Glu Pro Gly Gln
 1               5
```

(2) INFORMATION FOR SEQ ID NO:75:

(i) SEQUENCE CHARACTERISTICS:
        (A) LENGTH: 8 amino acids
        (B) TYPE: amino acid
        (D) TOPOLOGY: linear (x i) SEQUENCE DESCRIPTION: SEQ ID NO:75:

```
Glu Asp Leu Leu Glu Gly Gly Asp
 1               5
```

(2) INFORMATION FOR SEQ ID NO:76:

(i) SEQUENCE CHARACTERISTICS:
        (A) LENGTH: 9 amino acids
        (B) TYPE: amino acid
        (D) TOPOLOGY: linear (x i) SEQUENCE DESCRIPTION: SEQ ID NO:76:

```
Leu Asp Leu Ile Gln Glu Glu Glu Arg
 1               5
```

(2) INFORMATION FOR SEQ ID NO:77:

(i) SEQUENCE CHARACTERISTICS:
        (A) LENGTH: 9 amino acids
        (B) TYPE: amino acid
        (D) TOPOLOGY: linear (x i) SEQUENCE DESCRIPTION: SEQ ID NO:77:

```
His Asp Leu Ile Glu Glu Val Glu Gln
```

1               5

( 2 ) INFORMATION FOR SEQ ID NO:78:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:78:

Glu Asp Leu Leu Glu Glu Asp Pro Thr
1               5

( 2 ) INFORMATION FOR SEQ ID NO:79:

( i ) SEQUENCE CHARACTERISTICS:
( A ) LENGTH: 50 amino acids
( B ) TYPE: amino acid
( D ) TOPOLOGY: linear ( x i ) SEQUENCE DESCRIPTION: SEQ ID NO:79:

Ser Ala Pro Glu Gln Pro Ala Pro Leu Pro Glu Val Gly Asn Gln Asp
1               5                   10                  15

Ala Val Pro Gln Val Ala Ile Pro Leu Pro Ala Cys Glu Pro Gln Pro
            20                  25                  30

Glu Val Asp Gly Lys Gln Glu Val Thr Asp Cys Glu Val Asn Asp Val
        35                  40                  45

Glu Glu
50

( 2 ) INFORMATION FOR SEQ ID NO:80:

( i ) SEQUENCE CHARACTERISTICS:
( A ) LENGTH: 55 amino acids
( B ) TYPE: amino acid
( D ) TOPOLOGY: linear ( x i ) SEQUENCE DESCRIPTION: SEQ ID NO:80:

Ala Leu Arg Asp Phe Gly Lys Pro Asn Asp Gly Lys Ala Ala Trp Thr
1               5                   10                  15

Asp Thr Val Leu Thr Ser Lys Lys Pro Lys Leu Glu Ser Arg Ser Asp
            20                  25                  30

Ser Pro Ala Trp Ser Leu Ser Gly Arg Asp Glu Pro Glu Thr Gly Ser
        35                  40                  45

Pro Pro Cys Phe Asp Glu Tyr
    50              55

( 2 ) INFORMATION FOR SEQ ID NO:81:

( i ) SEQUENCE CHARACTERISTICS:
( A ) LENGTH: 92 amino acids
( B ) TYPE: amino acid
( D ) TOPOLOGY: linear ( x i ) SEQUENCE DESCRIPTION: SEQ ID NO:81:

Leu Pro Pro Leu Leu Thr Pro Thr Glu Pro Ser Ser Pro Pro Pro Cys
1               5                   10                  15

Pro Pro Val Leu Thr Val Ala Thr Pro Pro Pro Leu Leu Pro Thr
            20                  25                  30

Val Pro Leu Ser His Pro Ser Asp Ala Ser Pro Gln Gln Cys Pro
        35                  40                  45

Ser Pro Phe Ser Asn Thr Thr Ala Gln Ser Pro Leu Pro Ile Leu Ser
    50              55                  60

```
            Pro  Thr  Val  Ser  Pro  Ser  Pro  Ser  Pro  Ile  Pro  Pro  Val  Glu  Pro  Leu
             65                 70                      75                           80

Met  Ser  Ala  Ala  Ser  Pro  Gly  Pro  Pro  Thr  Leu  Ser
                                 85                      90
```

( 2 ) INFORMATION FOR SEQ ID NO:82:

( i ) SEQUENCE CHARACTERISTICS:
        ( A ) LENGTH: 86 amino acids
        ( B ) TYPE: amino acid
        ( D ) TOPOLOGY: linear ( x i ) SEQUENCE DESCRIPTION: SEQ ID NO:82:

```
            Cys  Asn  Val  Cys  Glu  Ser  Pro  Phe  Leu  Ser  Ile  Lys  Asp  Leu  Thr  Lys
             1                  5                       10                          15

His  Leu  Ser  Val  His  Ala  Glu  Glu  Trp  Pro  Phe  Lys  Cys  Glu  Phe  Cys
                            20                      25                       30

Val  Gln  Leu  Phe  Lys  Val  Lys  Thr  Asp  Leu  Ser  Glu  His  Arg  Phe  Leu
                       35                           40                       45

Leu  His  Gly  Val  Gly  Asn  Ile  Phe  Val  Cys  Ser  Val  Cys  Lys  Lys  Glu
                  50                      55                       60

Phe  Ala  Phe  Leu  Cys  Asn  Leu  Gln  Gln  His  Gln  Arg  Asp  Leu  His  Pro
             65                 70                      75                           80

Asp  Glu  Val  Cys  Thr  His
                                 85
```

( 2 ) INFORMATION FOR SEQ ID NO:83:

( i ) SEQUENCE CHARACTERISTICS:
        ( A ) LENGTH: 77 amino acids
        ( B ) TYPE: amino acid
        ( D ) TOPOLOGY: linear ( x i ) SEQUENCE DESCRIPTION: SEQ ID NO:83:

```
            Thr  Arg  Ile  Gly  Val  Trp  Ala  Thr  Lys  Pro  Ile  Leu  Lys  Gly  Lys  Lys
             1                  5                       10                          15

Phe  Gly  Pro  Phe  Val  Gly  Asp  Lys  Lys  Arg  Ser  Gln  Val  Arg  Asn
                            20                      25                       30

Asn  Val  Tyr  Met  Trp  Glu  Val  Tyr  Tyr  Pro  Asn  Leu  Gly  Trp  Met  Cys
                       35                           40                       45

Ile  Asp  Ala  Thr  Asp  Pro  Glu  Lys  Gly  Asn  Trp  Leu  Arg  Tyr  Val  Asn
                  50                      55                       60

Trp  Ala  Cys  Ser  Gly  Glu  Glu  Gln  Asn  Leu  Phe  Pro  Leu
             65                 70                      75
```

( 2 ) INFORMATION FOR SEQ ID NO:84:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO:84:

```
            Glu  Ile  Asn  Arg  Ala  Ile  Tyr  Tyr  Lys  Thr  Leu  Lys  Pro  Ile  Ala  Pro
             1                  5                       10                          15

Gly  Glu  Glu  Leu  Leu  Val  Trp  Tyr  Asn  Gly  Glu  Asp  Asn  Pro
                            20                      25                       30
```

( 2 ) INFORMATION FOR SEQ ID NO:85:

( i ) SEQUENCE CHARACTERISTICS:

(A) LENGTH: 8 amino acids
        (B) TYPE: amino acid
        (D) TOPOLOGY: linear (xi) SEQUENCE DESCRIPTION: SEQ ID NO:85:

Gly Lys Pro Asn Asp Gly Lys Ala
    1               5

(2) INFORMATION FOR SEQ ID NO:86:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:86:

Asp Glu Arg Glu Thr
    1               5

(2) INFORMATION FOR SEQ ID NO:87:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:87:

Asp Xaa Xaa Xaa Xaa Xaa Xaa Xaa Xaa Xaa Xaa Xaa Xaa Thr
    1               5                   10

(2) INFORMATION FOR SEQ ID NO:88:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:88:

Asp Xaa Xaa Xaa Xaa Xaa Xaa Xaa Xaa Xaa Xaa Xaa Thr
    1               5                   10

(2) INFORMATION FOR SEQ ID NO:89:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:89:

Asp Ser Glu Gly
    1

(2) INFORMATION FOR SEQ ID NO:90:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:90:

Thr Gln Pro Asp
    1

(2) INFORMATION FOR SEQ ID NO:91:

(i) SEQUENCE CHARACTERISTICS:
        (A) LENGTH: 11 amino acids
        (B) TYPE: amino acid -continued (D) TOPOLOGY: linear (xi) SEQUENCE DESCRIPTION: SEQ ID NO:91:

Glu Ile Arg Cys Asp Glu Lys Pro Glu Asp Leu
1               5                   10

(2) INFORMATION FOR SEQ ID NO:92:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:92:

CCAGAACCAG ACGAGCGATT                                              20

(2) INFORMATION FOR SEQ ID NO:93:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:93:

AGTTCTGGGG ATTTGCATG                                               19